(12) United States Patent
Voege et al.

(10) Patent No.: US 7,617,826 B1
(45) Date of Patent: Nov. 17, 2009

(54) CONSERVER

(75) Inventors: James A Voege, Carmel, IN (US);
Matthew G Thie, Indianapolis, IN (US);
David A Ferrer, Westfield, IN (US)

(73) Assignee: Ameriflo, Inc., Carmel, IN (US)

(*) Notice: Subject to any disclaimer, the term of this patent is extended or adjusted under 35 U.S.C. 154(b) by 0 days.

(21) Appl. No.: 11/725,392

(22) Filed: Mar. 19, 2007

Related U.S. Application Data

(63) Continuation-in-part of application No. 11/724,350, filed on Mar. 15, 2007, which is a continuation-in-part of application No. 11/069,084, filed on Feb. 28, 2005.

(60) Provisional application No. 60/548,058, filed on Feb. 26, 2004, provisional application No. 60/606,288, filed on Sep. 1, 2004, provisional application No. 60/620,890, filed on Oct. 21, 2004, provisional application No. 60/783,243, filed on Mar. 17, 2006, provisional application No. 60/784,216, filed on Mar. 20, 2006.

(51) Int. Cl.
*A61M 16/20* (2006.01)
*A62B 7/00* (2006.01)
*A62B 7/02* (2006.01)

(52) U.S. Cl. .................... 128/204.26; 128/204.18; 128/204.21; 128/205.24; 222/3

(58) Field of Classification Search ............ 128/204.26, 128/204.18, 204.21, 205.24, 913, 200.24, 128/201.21, 201.27, 201.28, 202.27; 222/3
See application file for complete search history.

(56) References Cited

U.S. PATENT DOCUMENTS

| 2,912,979 | A | 11/1959 | Lieber |
| 3,400,712 | A | 9/1968 | Finan |
| 3,400,713 | A | 9/1968 | Finan |
| 3,434,471 | A | 3/1969 | Liston |
| 3,556,095 | A | 1/1971 | Ismach |
| 3,567,175 | A | 3/1971 | Sciuto |
| 3,604,415 | A | 9/1971 | Hoenig |

(Continued)

FOREIGN PATENT DOCUMENTS

| DE | 27 11 664 | 10/1977 |
| DE | 3329954 | 3/1985 |
| DE | 43 12 510 | 10/1993 |
| EP | 0266051 | 5/1988 |
| EP | 0 217 573 | 4/1992 |

(Continued)

OTHER PUBLICATIONS

Auerbach, et al., "A New Oxygen Cannula System Using Intermittent-Demand Nasal Flow," Chest, 74:1, pp. 39-44, Jul. 1978.
Brown, C. C., Reservoir nasal cannula prevents oxygen desaturation in copd patients during eating, American Review of Respiratory Disease 137 (4 Part 2), p. 157, 1988, U.S., (bibliographic information).
Carter, R., Evaluation of the pendant oxygen-conserving nasal cannula during exercise, Chest 89 (6), Jun. 1986, p. 806-10, U.S., (abstract only).

(Continued)

*Primary Examiner*—Justine R Yu
*Assistant Examiner*—Clinton Ostrup
(74) *Attorney, Agent, or Firm*—Baker & Daniels LLP

(57) ABSTRACT

Fluid regulators provide a fluid to a cannula for use by a person. Fluid conservers also a fluid to a cannula for use by a person. A fluid conserver may be operational in a continuous flow mode of operation and an intermittent flow mode of operation. The selection of either the continuous flow mode of operation and the intermittent flow mode of operation may be based on a position of a flow selector. A home fill device may operate with a fluid conserver and may include an oxygen concentrator which provides a source of fluid.

16 Claims, 45 Drawing Sheets

U.S. PATENT DOCUMENTS

| | | |
|---|---|---|
| 3,643,660 A | 2/1972 | Hudson et al. |
| 3,741,208 A | 6/1973 | Jonsson et al. |
| 3,783,891 A | 1/1974 | Christianson |
| 3,802,417 A | 4/1974 | Lang |
| 3,805,780 A | 4/1974 | Cramer et al. |
| 3,807,687 A | 4/1974 | Thompson |
| 3,830,257 A | 8/1974 | Metivier |
| 3,834,382 A | 9/1974 | Lederman et al. |
| 3,905,362 A | 9/1975 | Eyrick et al. |
| 3,910,270 A | 10/1975 | Stewart |
| 3,911,899 A | 10/1975 | Hattes |
| 3,911,948 A | 10/1975 | Collins et al. |
| 3,949,749 A | 4/1976 | Stewart |
| 3,964,476 A | 6/1976 | Palleni |
| 4,003,377 A | 1/1977 | Dahl |
| 4,008,716 A | 2/1977 | Amlong |
| 4,033,343 A | 7/1977 | Jones |
| 4,054,133 A | 10/1977 | Myers |
| 4,057,059 A | 11/1977 | Reid, Jr. et al. |
| 4,062,356 A | 12/1977 | Merrifield |
| 4,064,890 A | 12/1977 | Collins et al. |
| 4,082,093 A | 4/1978 | Fry et al. |
| 4,096,875 A | 6/1978 | Jones et al. |
| 4,098,272 A | 7/1978 | Stewart |
| 4,106,503 A | 8/1978 | Rosenthal et al. |
| 4,120,300 A | 10/1978 | Tiep |
| 4,155,356 A | 5/1979 | Venegas |
| 4,172,468 A | 10/1979 | Ruus |
| 4,206,754 A | 6/1980 | Cox et al. |
| 4,211,221 A | 7/1980 | Schwanbom et al. |
| 4,227,523 A | 10/1980 | Warnow et al. |
| 4,232,668 A | 11/1980 | Strupat |
| 4,241,732 A | 12/1980 | Berndtsson |
| 4,241,896 A | 12/1980 | Voege |
| 4,256,138 A | 3/1981 | Chapman |
| 4,278,110 A | 7/1981 | Price et al. |
| 4,323,064 A | 4/1982 | Hoenig et al. |
| 4,331,455 A | 5/1982 | Sato |
| 4,333,451 A | 6/1982 | Paluch |
| 4,336,590 A | 6/1982 | Jacq et al. |
| 4,363,424 A | 12/1982 | Holben et al. |
| 4,366,947 A | 1/1983 | Voege |
| 4,381,002 A | 4/1983 | Mon |
| 4,409,977 A | 10/1983 | Bisera et al. |
| 4,428,372 A | 1/1984 | Beysel et al. |
| 4,436,090 A | 3/1984 | Darling |
| 4,436,434 A | 3/1984 | Stoll et al. |
| 4,449,990 A | 5/1984 | Tedford, Jr. |
| 4,450,838 A | 5/1984 | Miodownik |
| 4,457,303 A | 7/1984 | Durkan |
| 4,459,982 A | 7/1984 | Fry |
| 4,461,293 A | 7/1984 | Chen |
| 4,471,773 A | 9/1984 | Bunnell et al. |
| 4,477,264 A | 10/1984 | Kratz et al. |
| 4,481,944 A | 11/1984 | Bunnell |
| 4,502,873 A | 3/1985 | Mottram et al. |
| 4,532,923 A | 8/1985 | Flynn |
| 4,538,604 A | 9/1985 | Usry et al. |
| 4,552,571 A | 11/1985 | Dechene |
| 4,561,287 A | 12/1985 | Rowland |
| 4,572,175 A | 2/1986 | Flynn |
| 4,575,042 A | 3/1986 | Grimland et al. |
| 4,576,616 A | 3/1986 | Mottram et al. |
| 4,581,942 A | 4/1986 | Ogura et al. |
| 4,584,996 A | 4/1986 | Blum |
| 4,586,136 A | 4/1986 | Lewis |
| 4,592,349 A | 6/1986 | Bird |
| 4,596,247 A | 6/1986 | Whitwam et al. |
| 4,612,928 A | 9/1986 | Tiep et al. |
| 4,617,924 A | 10/1986 | Heim et al. |
| 4,627,860 A | 12/1986 | Rowland |
| 4,644,947 A | 2/1987 | Whitwam et al. |
| 4,644,958 A | 2/1987 | Brisson et al. |
| 4,648,395 A | 3/1987 | Sato et al. |
| 4,665,911 A | 5/1987 | Williams et al. |
| 4,673,415 A | 6/1987 | Stanford |
| 4,681,099 A | 7/1987 | Sato et al. |
| 4,698,075 A | 10/1987 | Dechene |
| 4,699,173 A | 10/1987 | Rohling |
| 4,706,664 A | 11/1987 | Snook et al. |
| 4,712,557 A | 12/1987 | Harris |
| 4,719,910 A | 1/1988 | Jensen |
| 4,744,356 A | 5/1988 | Greenwood |
| 4,747,402 A | 5/1988 | Reese et al. |
| 4,747,403 A | 5/1988 | Gluck et al. |
| 4,784,130 A | 11/1988 | Kenyon et al. |
| 4,805,612 A | 2/1989 | Jensen |
| 4,821,709 A | 4/1989 | Jensen |
| 4,823,788 A | 4/1989 | Smith et al. |
| 4,827,922 A | 5/1989 | Champain et al. |
| 4,829,998 A | 5/1989 | Jackson |
| 4,832,014 A | 5/1989 | Perkins |
| 4,832,578 A | 5/1989 | Putt |
| 4,838,257 A | 6/1989 | Hatch |
| 4,844,446 A | 7/1989 | Thie et al. |
| 4,932,402 A | 6/1990 | Snook et al. |
| 4,936,327 A | 6/1990 | Baumann |
| 4,938,212 A | 7/1990 | Snook et al. |
| 4,940,162 A | 7/1990 | Thie |
| 4,960,119 A | 10/1990 | Hamlin |
| 4,971,049 A | 11/1990 | Rotariu et al. |
| 4,971,609 A | 11/1990 | Pawlos |
| 4,986,268 A | 1/1991 | Tehrani |
| 5,005,570 A | 4/1991 | Perkins |
| 5,007,420 A | 4/1991 | Bird |
| 5,016,673 A | 5/1991 | Carter et al. |
| 5,020,974 A | 6/1991 | Searle |
| 5,033,940 A | 7/1991 | Baumann |
| 5,048,515 A | 9/1991 | Sanso |
| 5,052,400 A | 10/1991 | Dietz |
| 5,060,514 A | 10/1991 | Ayisworth |
| 5,071,453 A | 12/1991 | Hradek et al. |
| 5,074,298 A * | 12/1991 | Arnoth .................. 128/204.18 |
| 5,074,299 A | 12/1991 | Dietz |
| 5,092,326 A | 3/1992 | Winn et al. |
| 5,099,837 A | 3/1992 | Russel, Sr. et al. |
| 5,116,088 A | 5/1992 | Bird |
| 5,144,945 A | 9/1992 | Nishino et al. |
| 5,165,397 A | 11/1992 | Arp |
| 5,183,037 A | 2/1993 | Dearman |
| 5,195,874 A | 3/1993 | Odagiri |
| 5,199,423 A | 4/1993 | Harral et al. |
| 5,199,424 A | 4/1993 | Sullivan et al. |
| 5,211,171 A | 5/1993 | Choromokos |
| 5,241,955 A | 9/1993 | Dearman et al. |
| 5,245,995 A | 9/1993 | Sullivan et al. |
| 5,259,373 A | 11/1993 | Gruenke et al. |
| 5,315,988 A | 5/1994 | Clarke et al. |
| 5,331,995 A | 7/1994 | Westfall et al. |
| 5,354,361 A | 10/1994 | Coffield |
| 5,360,000 A | 11/1994 | Carter |
| 5,368,022 A | 11/1994 | Wagner |
| 5,370,112 A | 12/1994 | Perkins |
| 5,386,824 A | 2/1995 | Nelepka |
| 5,398,676 A | 3/1995 | Press et al. |
| 5,411,059 A | 5/1995 | Sever et al. |
| 5,413,096 A | 5/1995 | Hart |
| 5,415,161 A | 5/1995 | Ryder |
| 5,438,980 A | 8/1995 | Phillips |
| 5,443,062 A | 8/1995 | Hayes |
| 5,474,595 A | 12/1995 | McCombs |
| 5,478,046 A | 12/1995 | Szabo |
| 5,485,983 A | 1/1996 | Voege et al. |
| 5,495,848 A | 3/1996 | Aylsworth et al. |

| | | | |
|---|---|---|---|
| 5,503,146 A | 4/1996 | Froehlich et al. | |
| 5,522,382 A | 6/1996 | Sullivan et al. | |
| 5,528,976 A | 6/1996 | Ikeda et al. | |
| 5,531,679 A | 7/1996 | Schulman et al. | |
| 5,531,807 A | 7/1996 | McCombs | |
| 5,544,858 A | 8/1996 | Rogers et al. | |
| 5,546,985 A | 8/1996 | Bartholomew | |
| 5,549,106 A | 8/1996 | Gruenke et al. | |
| 5,551,419 A | 9/1996 | Froehlich et al. | |
| 5,558,086 A | 9/1996 | Smith et al. | |
| 5,570,682 A | 11/1996 | Johnson | |
| 5,596,984 A | 1/1997 | O'Mahony et al. | |
| 5,603,315 A | 2/1997 | Sasso, Jr. | |
| 5,632,298 A * | 5/1997 | Artinian | 137/102 |
| 5,651,361 A | 7/1997 | Dearman et al. | |
| 5,666,945 A | 9/1997 | Davenport | |
| 5,685,297 A | 11/1997 | Schuler | |
| 5,701,889 A | 12/1997 | Danon | |
| 5,702,238 A | 12/1997 | Simmons et al. | |
| 5,724,963 A | 3/1998 | Seeley | |
| 5,752,544 A | 5/1998 | Yves | |
| 5,755,224 A | 5/1998 | Good et al. | |
| 5,785,050 A | 7/1998 | Davidson et al. | |
| 5,813,314 A | 9/1998 | Michiyuki et al. | |
| 5,858,062 A | 1/1999 | McCulloh et al. | |
| 5,881,725 A * | 3/1999 | Hoffman et al. | 128/204.26 |
| 5,899,223 A | 5/1999 | Shuman, Jr. | |
| 5,917,135 A | 6/1999 | Michaels et al. | |
| 5,924,419 A | 7/1999 | Kotliar | |
| 5,928,189 A | 7/1999 | Phillips et al. | |
| 5,968,236 A | 10/1999 | Bassine | |
| 5,988,165 A | 11/1999 | Richey, II et al. | |
| 5,997,611 A | 12/1999 | Doong et al. | |
| 6,009,900 A | 1/2000 | Elgert et al. | |
| 6,016,803 A | 1/2000 | Volberg et al. | |
| 6,053,056 A | 4/2000 | Zaiser et al. | |
| 6,079,313 A | 6/2000 | Wolcott et al. | |
| 6,082,359 A | 7/2000 | Preston | |
| 6,082,396 A | 7/2000 | Davidson | |
| 6,089,259 A | 7/2000 | Shuman, Jr. | |
| 6,116,242 A * | 9/2000 | Frye et al. | 128/205.24 |
| 6,137,417 A | 10/2000 | McDermott | |
| 6,152,134 A | 11/2000 | Webber et al. | |
| 6,155,258 A | 12/2000 | Voege | |
| 6,158,457 A | 12/2000 | Byrd et al. | |
| 6,189,531 B1 | 2/2001 | Tatarek | |
| 6,240,943 B1 | 6/2001 | Smith | |
| 6,273,130 B1 | 8/2001 | Cossins | |
| 6,286,543 B1 | 9/2001 | Davidson | |
| 6,302,107 B1 | 10/2001 | Richey, II et al. | |
| 6,321,779 B1 | 11/2001 | Miller et al. | |
| 6,325,097 B1 | 12/2001 | Gallant et al. | |
| 6,354,564 B1 | 3/2002 | Van Scyoc et al. | |
| 6,364,161 B1 | 4/2002 | Pryor | |
| 6,382,589 B1 | 5/2002 | Edstrom, Sr. et al. | |
| 6,386,235 B1 | 5/2002 | McCulloh et al. | |
| 6,393,802 B1 | 5/2002 | Bowser et al. | |
| 6,394,088 B1 * | 5/2002 | Frye et al. | 128/204.26 |
| 6,401,714 B1 | 6/2002 | Giorgini | |
| 6,401,740 B2 | 6/2002 | Zaiser | |
| 6,446,630 B1 | 9/2002 | Todd, Jr. | |
| 6,467,325 B1 | 10/2002 | Zaiser | |
| 6,478,857 B2 | 11/2002 | Czabala | |
| 6,484,720 B1 | 11/2002 | Marquard, II et al. | |
| 6,484,721 B1 | 11/2002 | Bliss | |
| 6,510,747 B1 | 1/2003 | Zaiser | |
| 6,532,958 B1 | 3/2003 | Buan et al. | |
| 6,568,391 B1 | 5/2003 | Tatarek et al. | |
| 6,575,430 B1 | 6/2003 | Smith, III | |
| 6,581,592 B1 | 6/2003 | Bathe et al. | |
| 6,612,307 B2 * | 9/2003 | Byrd | 128/204.26 |
| 6,647,982 B1 | 11/2003 | Zaiser et al. | |
| 6,691,702 B2 | 2/2004 | Appel et al. | |
| 6,712,087 B2 | 3/2004 | Hill et al. | |
| 6,749,405 B2 | 6/2004 | Bassine | |
| 6,752,152 B2 * | 6/2004 | Gale et al. | 128/204.26 |
| 6,764,534 B2 | 7/2004 | McCombs et al. | |
| 6,772,762 B2 | 8/2004 | Piesinger | |
| 6,792,846 B2 | 9/2004 | Barrett | |
| 6,805,122 B2 | 10/2004 | Richey, II et al. | |
| 6,827,084 B2 | 12/2004 | Grubb, Jr. | |
| 6,837,245 B2 | 1/2005 | Matheny et al. | |
| 6,889,710 B2 | 5/2005 | Wagner | |
| 6,889,726 B2 | 5/2005 | Richey, II et al. | |
| 6,923,180 B2 | 8/2005 | Richey, II et al. | |
| 6,949,133 B2 | 9/2005 | McCombs et al. | |
| 6,986,350 B2 | 1/2006 | Zaiser et al. | |
| 7,066,985 B2 * | 6/2006 | Deane et al. | 95/96 |
| 7,073,773 B2 | 7/2006 | Nuttall et al. | |
| 7,204,249 B1 | 4/2007 | Richey, II et al. | |
| 7,294,170 B2 | 11/2007 | Richey, II et al. | |
| 7,448,594 B2 | 11/2008 | Voege et al. | |
| 2002/0073998 A1 | 6/2002 | Byrd | |
| 2002/0144683 A1 | 10/2002 | Gurnee et al. | |
| 2003/0026710 A1 | 2/2003 | Nishikawa et al. | |
| 2003/0075179 A1 | 4/2003 | Gale et al. | |
| 2003/0150455 A1 | 8/2003 | Bliss et al. | |
| 2005/0045040 A1 | 3/2005 | McCombs | |
| 2005/0103341 A1 | 5/2005 | Deane et al. | |
| 2005/0161043 A1 | 7/2005 | Whitley et al. | |
| 2005/0178387 A1 | 8/2005 | Gurnee et al. | |

FOREIGN PATENT DOCUMENTS

| | | |
|---|---|---|
| EP | 0 283 141 | 9/1995 |
| EP | 1 028 770 | 8/2000 |
| GB | 497113 | 12/1938 |
| GB | 2 170 409 A | 8/1986 |
| JP | 01-274771 | 11/1989 |
| JP | 3-90164 | 4/1991 |
| JP | 5-92038 | 4/1993 |
| JP | 6-197967 | 7/1994 |
| JP | 6-205833 | 7/1994 |
| JP | 6-315533 | 11/1994 |
| JP | 8-19615 | 1/1996 |
| JP | 8-173539 | 7/1996 |
| JP | 00-176018 | 6/2000 |
| JP | 00-192878 | 7/2000 |
| JP | 2000192878 | 7/2000 |
| JP | 01-182653 | 7/2001 |
| WO | 87/02590 | 5/1987 |
| WO | 87/06142 | 10/1987 |
| WO | WO 95/23624 | 9/1995 |
| WO | WO 96/40336 | 12/1996 |
| WO | WO 97/06844 | 2/1997 |
| WO | 98/19282 | 5/1998 |
| WO | WO 99/22795 | 5/1999 |
| WO | WO 01/45433 | 6/2001 |
| WO | 02/29164 | 4/2002 |

OTHER PUBLICATIONS

Claiborne, R. A., Evaluation of the use of an oxygen conservation device in long-term oxygen therapy, American Review of Respiratory Disease 136 (5), p. 1095-8, U.S., (abstract only).

Esco2rt Pulse—Conserving Regulator literature, The Respiratory Group, 2002, 2 pgs.

Evans, T.W., An oxygen conservation device in patients with corpulmonale—an unsustained effect, Thorax, V42, N3, p. 216, 1987, England, (bibliographic information).

Fitzgerald, D. J., Variance of oxygen with nasal cannula and transtracheal delivery systems, American Review Of Respiratory Disease, V147, N4, Apr. 1993, p. A976, (bibliographic information).

Gould, G. A., Comparison of two oxygen conserving nasal prong systems and the effects of nose and mouth breathing, Thorax 41 (10), Oct. 1986, p. 808-9, England, (bibliographic information).

Gould, G.A., Clinical assessment of oxygen conserving devices in chronic bronchitis and emphysema, Thorax 40 (11), Nov. 1985, p. 820-4, England, (abstract only).

Haber, H., Comparison of an oxygen-conserving module 'Oxytron' and the reservoir cannula 'Oxymizer Pendant' with continuous oxygen administration via nasal prong in hypoxemic patients, Wiener Klinische Wochenschrift 102, May 25, 1990.

Hayhurst. M. D., A new low-flow oxygen-conserving cannula, South African Medical Journal 71 (4), Feb. 21, 1987, p. 251-2, South Africa, (abstract only).

Hoffman, L. A., Nasal cannula and transtracheal oxygen delivery. A comparison of patient response after 6 months of each technique, American Review of Respiratory Disease 145 (4 Pt 1), Apr. 1992, p. 827-521, U.S., (abstract only).

Hoffman, L. A., Novel strategies for delivering oxygen: reservoir cannula, demand flow, and transtracheal oxygen administration, Respiratory Care, Apr. 1994, 39 (4), p. 363-77, discussion 386-9, U.S., (abstract only).

Inovo Oxygen Regulators, www.life-assist.com/inovo.html, Apr. 20, 2004, 4 pgs.

Ishihara, T., Oxygen-conserving delivery system, Nihon Kyobu Shikkan Gakkai zasshi, 30 Suppl., Dec. 1992, p. 156-63, Japan, (abstract only).

Kerby, G. R., Clinical efficacy and cost benefit of pulse flow oxygen in hospitalized patients, Chest 97 (2), Feb. 1990, p. 369-72, U.S., (abstract only).

Krause-Michel, B., Improvement of compliance in long-term oxygen therapy by eyeglasses with integrated single nasal cannula for oxygen supply, Atemwegs-und Lungenkrankheiten 21 (10), p. 516-517, 1995, Germany, (abstract only).

Leger, P., Oxygen-conserving devices for delivery of long-term oxygen therapy, Agressologie- Revue Internationale De Physio-Biologie Et De Pharmacologie Appliquees Aux Effets De L'agression 29 (8), Sept. 1988, p. 603-6, France, (bibliographic information).

Leger, P., Simultaneous use of a pulsed dose demand valve with a transtracheal catheter an optimal oxygen saving for long-term oxygen therapy, American Review of Respiratory Disease 133 (4 Suppl), 1986, p. A350, U.S., (bibliographic information).

Lin Cai Yuan, Clinical evaluation of pulse-dose and continuous-flow oxygen delivery, Respiratory Care, 1995, 40/8 p. 811-814, U.S., (abstract only).

Momoeda, K., Oropharyngeal oxygen concentration using twin nasal oxygen cannulae with compression—a comparison with conventional devices, Anesthesiology (Hagerstown)85 (3A), p. A447, 1996, (bibliographic information).

Monasterio, C., The evaluation of the oxygen-conserving valve during exertion, Medicina Clinica 98 (4), p. 128-30, Feb. 1, 1992, Spain, (abstract only).

Moore-Gillon, J., Oxygen-conserving delivery devices, Respiratory Medicine 83 (4), Jul. 1989, p. 263-4, England, (bibliographic information).

Moore-Gillon, J.C., An oxygen conserving nasal cannula, Thorax 40 (11), Nov. 1985, p. 817-9, England, (abstract only).

Pesce, L., Usefulness of a new oxygen conserving delivery device in 10 patients affected by respiratory failure, Giornale Italiano delle Malattie del Torace 40 (6), 1986, p. 427-429, Italy, (abstract only).

Precision Medical—Chrome Body Series Flowmeters, © 2002 Precision Medical, Inc., 1 pg.

Precision Medical—Dial Flowmeters, © 2002 Precision Medical, Inc., 1 pg.

Precision Medical—Easy Dial Regulators, © 2002 Precision Medical, Inc., 1 pg.

Precision Medical—Easy Gauge Regulators, © 2002 Precision Medical, Inc., 1 pg.

Precision Medical—Easy Meter Regulators, © 2002 Precision Medical, Inc., 1 pg.

Precision Medical—Easy Pulse Oxygen Conserver Specifications, © 2002 Precision Medical, Inc., 1 pg.

Precision Medical—Easy Pulse Oxygen Conserving Regulator, © 2002 Precision Medical, Inc., 1 pg.

Precision Medical—Easy Regulators, © 2002 Precision Medical, Inc., 1 pg.

Precision Medical—Pediatric Flowmeters, © 2002 Precision Medical, Inc., 1 pg.

Precision Medical—Select Flowmeters, © 2002 Precision Medical, Inc., 1 pg.

Romberger, D. J., Comparison of continuous and pulse flow oxygen in hospital patients, American Review of Respiratory Disease 137 (4 Part 2), p. 158, 1988, U.S., (bibliographic information).

Rousseau, M., Oxygen delivery via nasal cannula how much oxygen are we actually delivering, Anesthesiology (Hagerstown) 71 (3A), 1989, p. A354, (bibliographic information).

Sabre Medical Elite Datasheet, Nov. 30, 2004, 1 pg.

Sabre Medical Elite description, http://www.gceuk.com/saber/domicillary_products/elite.html, Oct. 24, 2005, 1 pg.

Sabre Medical Elite QF Datasheet, Nov. 30, 2004, 1 pg.

Sabre Medical Integra Datasheet, Nov. 30, 2004, 1 pg.

Sabre Medical Portaflow description, http://www.gceuk.com/saber/domicillary_products/portaflow.html, Oct. 24, 2005, 1 pg.

Sabre Medical, Medical Gas Regulators, Nov. 30, 2004, 2 pages.

Senn, S., Efficacy of a pulsed oxygen delivery device during exercise in patients with chronic respiratory disease, Chest 96 (3), Sep. 1989, p. 467-72, ISSN 0012-3692, U.S., (abstract only).

Shigeoka, J.W., The current status of oxygen-conserving devices, Respiratory Care 30/10, 1985, 833-836, U.S., (bibliographic information).

Soffer, M., Conservation of oxygen supply using a reservoir nasal cannula in hypoxemic patients at rest and during exercise, Chest 88 (5), Nov. 1985, p. 663-8, U.S., (abstract only).

Strezelecki, L. R., Comparison of demand oxygen controlled and continuous flow oxygen in an intubated model, Chest 94 (1 Suppl), p. 91S, 1988, U.S., (bibliographic information).

Taube, J.C., Criteria for an adaptive fractional inspired oxygen controller, Computer-Based Medical Systems (Cat. No. 88CH2606-2), IEEE Comput. Soc. Press, Washington, DC, 1988, p. 129-32, (abstract only).

Tehrani, F. T., A feedback controller for supplemental oxygen treatment of newborn infants: a simulation study, Medical Engineering & Physics, Jul. 1994, 16 (4), p. 329-33, England, (abstract only).

Tiep, B., Oxygen conservation and oxygen-conserving devices in chronic lung disease. A review, Chest 92 (2), Aug. 1987, p. 263-72, U.S., (abstract only).

Tiep, B., Oxygen conserving devices in obstructive and restrictive disease, Atemwegs-und Lungenkrankheiten 18/Suppl. 2, p. S142-S149, 1992, Germany, (bibliographic information).

Tiep, B., Portable oxygen therapy with oxygen conserving devices and methodologies, IRCCS and Istituto di Clinica Tisiologica e Malattie Apparato Respiratorio, Univer, Jan. 1995, 50, p. 51-7, Italy, (abstract only).

Tiep, B.L., A new oxygen saving nasal cannula, American Review of Respiratory Disease 127 (4 Part 2), 1983, p. 86, U.S., (bibliographic information).

Tiep, B.L., A new pendant storage oxygen-conserving nasal cannula, Chest 87 (3), Mar. 1985, p. 381-3, U.S., (abstract only).

Tiep, B.L., Evaluation of a low-flow oxygen-conserving nasal cannula, American Review of Respiratory Disease 130 (3), Sep. 1984, p. 500-2, U.S., (abstract only).

Torregroza, M., Oxygen application with the pulse air oxygen delivery system compact station, European Respiratory Journal Supplement 9 (23), 1996, p. 443S, Stockholm, Sweden, (bibliographic information).

Tremper, J. C., Reliability of the oxymatic electronic oxygen conserver, American Review of Respiratory Disease 135 (4 Part 2), 1987, p. A194, U.S., (bibliographic information).

U.S. Statutory Invention Registration No. H1282, published Feb. 1, 1994, to Joyce et al., 10 pgs.

Vernay Laboratories—Umbrella Check Valves, www.vernay.com/products/umbrella.htm, Dec. 23, 2003, 5 pgs.

Vernay® Umbrella Check Valves brochure, Vernay Laboratories, Inc., May 9, 2003, 4 pgs.

Vilsvik, J., Oxygen-conserving nasal cannula: Oxymizer pendant, Tidsskrift for den Norske Laegeforening 112 (29), p. 3659-3662, 1992, Norway, (abstract only).

Vernay Laboratories, Inc.—A custom molded rubber products manufacturer with worldwide locations, www.vernay.com/products/diaphram.htm, Dec. 23, 2003, 3 pgs.

Yaeger, E. S., Oxygen therapy using pulse and continuous flow with a transtracheal catheter and a nasal cannula, Chest, Sep. 1994, 106 (3), p. 854-60, U.S., (abstract only).

Zwischenberger, J. B., Total respiratory support with single cannula venovenous ECMO: double lumen continuous flow vs. single lumen tidal flow, Transactions—American Society for Artificial Internal Organs 31, 1985, p. 610-5, U.S., (bibliographic information).

Chad Therapeutics, "The Total $O_2$® Delivery System," at least as early as Mar. 19, 2007, 1 pg.

Invacare® Oxygen Products brochure, 2005, 20 pgs.

Invacare® Venture HomeFill II M6 Cylinder Assembly product description, 2006, 2 pgs.

Invacare® Venture HomeFill II M9 Cylinder Assembly product description, 2006, 2 pgs.

Invacare® Venture HomeFill II Oxygen Compressor, Product ID: IOH200 product description, 2006, 2 pgs.

Invacare® Venture HomeFill II Ambulatory Package With Patient Convenience Pack, Product ID: IOH200PC product description, 2006, 2 pgs.

Invacare® Venture HomeFill II Ambulatory Package With Patient Convenience Pack, Product ID: IOH200PC4 product description, 2006, 2 pgs.

Invacare® Venture HomeFill II Ambulatory Package With Patient Convenience Pack, Product ID: IOH200PC9 product description, 2006, 2 pgs.

Invacare® HomeFill™ II Convenience Pack advertising, 2004, 2 pgs.

Invacare® Patient Convenience Pack—Cylinder, Product ID: HF2PCL4 product description, 2006, 2 pgs.

Invacare® Patient Convenience Pack—Cylinder, Product ID: HF2PCL6 product description, 2006, 2 pgs.

Invacare® Patient Convenience Pack—Cylinder, Product ID: HF2PC9 product description, 2006, 2 pgs.

Invacare® HomeFill™ II Compressor Operator's Manual, 2006, 40 pgs.

Invacare® HomeFill™ II Oxygen Conserving Cylinder Operator's Manual, 2005, 24 pgs.

Sunrise Medical, 535 Personal Oxygen Station brochure, 2006, 28 pgs., Sunrise Medical, Inc., Somerset, PA.

Sunrise Medical, DeVilbiss ifill™ Personal Oxygen Station, "What you want is what you get," brochure, Mar. 20, 2006, 2 pgs., Sunrise Medical, Inc., Longmont, CO.

Sunrise Medical, DeVilbiss® Oxygen Therapy brochure, 2005, 12 pgs., Sunrise Medical, Inc., Longmont, CO.

Sunrise Medical, DeVilbiss ifill™ Oxygen Cylinder brochure, 2006, 28 pgs., Sunrise Medical, Inc., Somerset, PA.

* cited by examiner

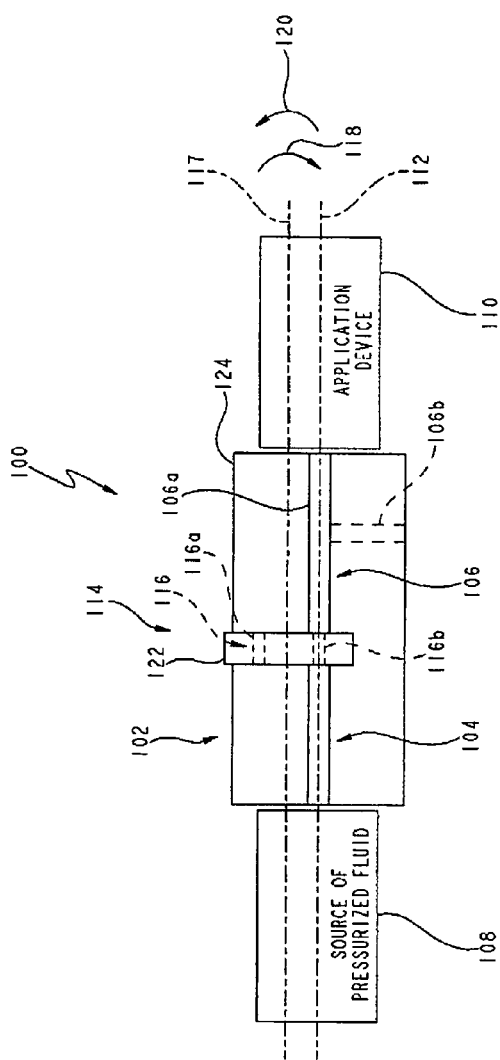
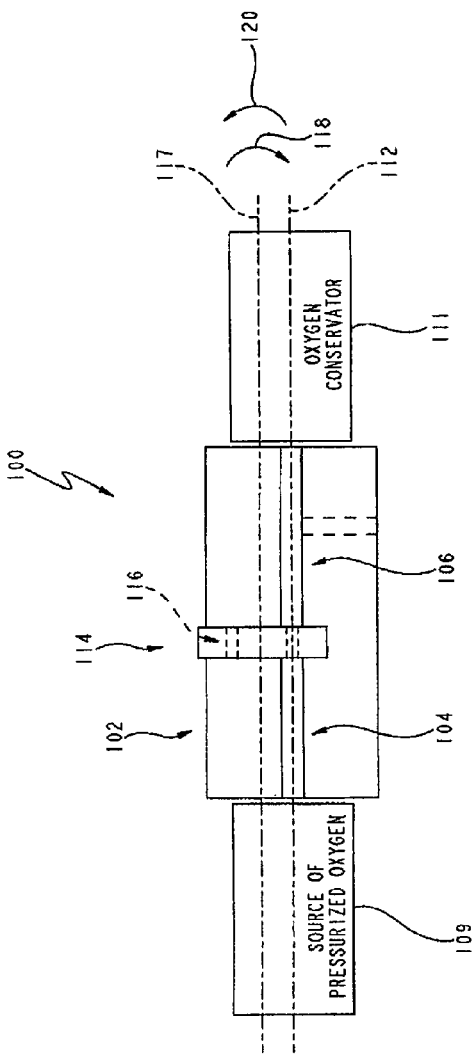

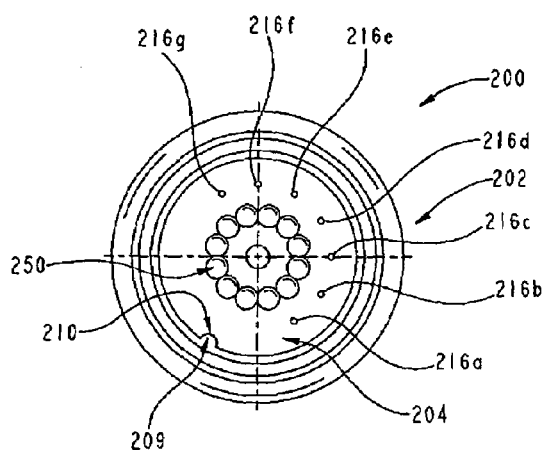
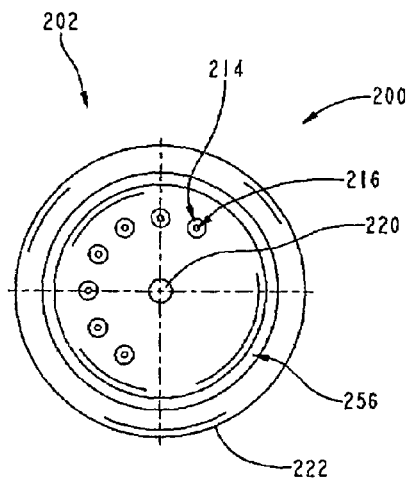
FIG. 3A
FIG. 3B
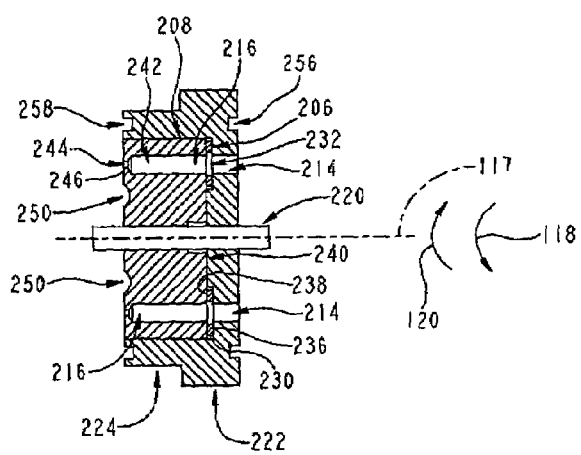
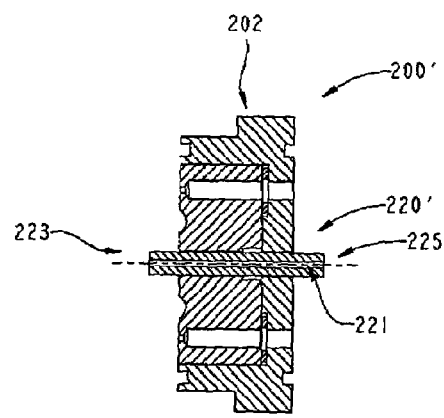
FIG. 4A
FIG. 4B

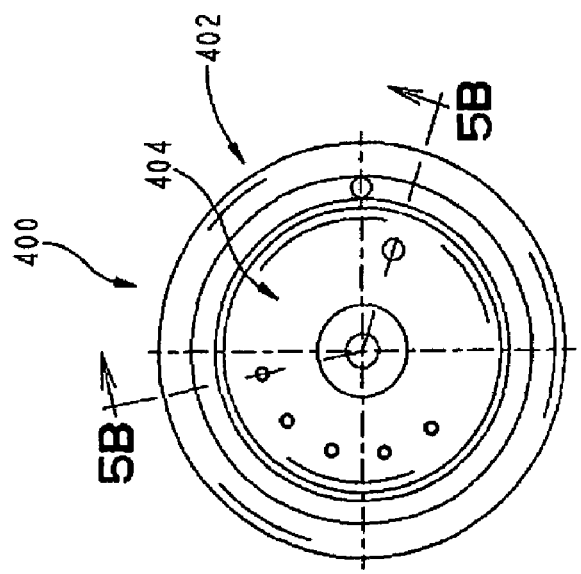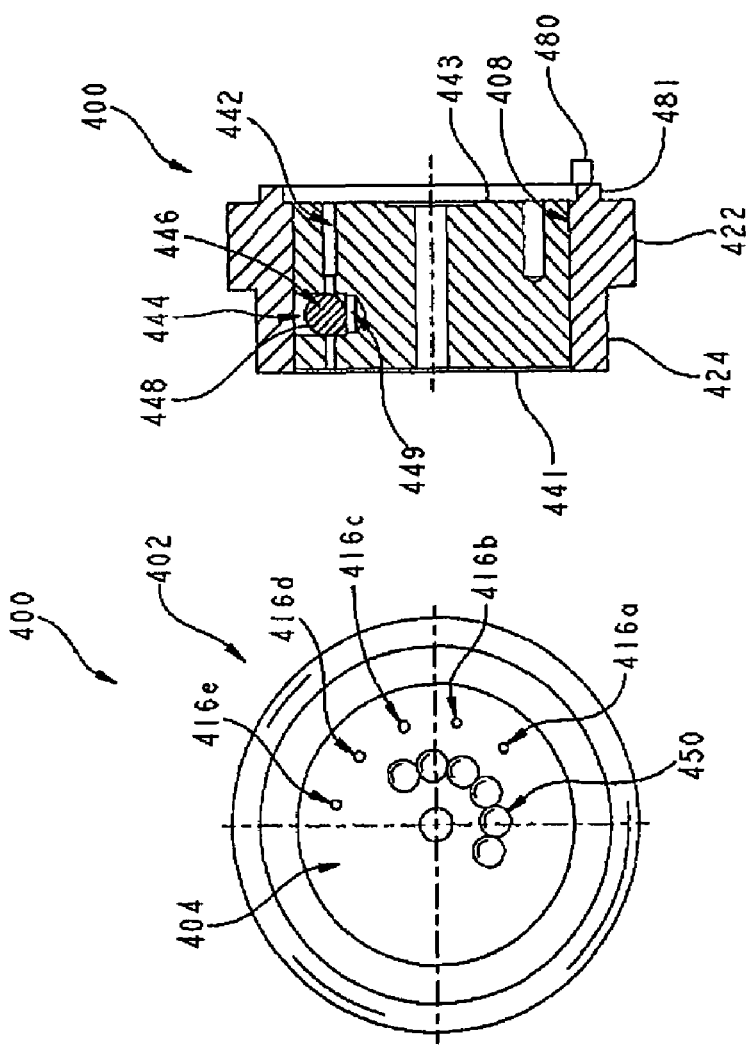
FIG. 5C
FIG. 5B
FIG. 5A

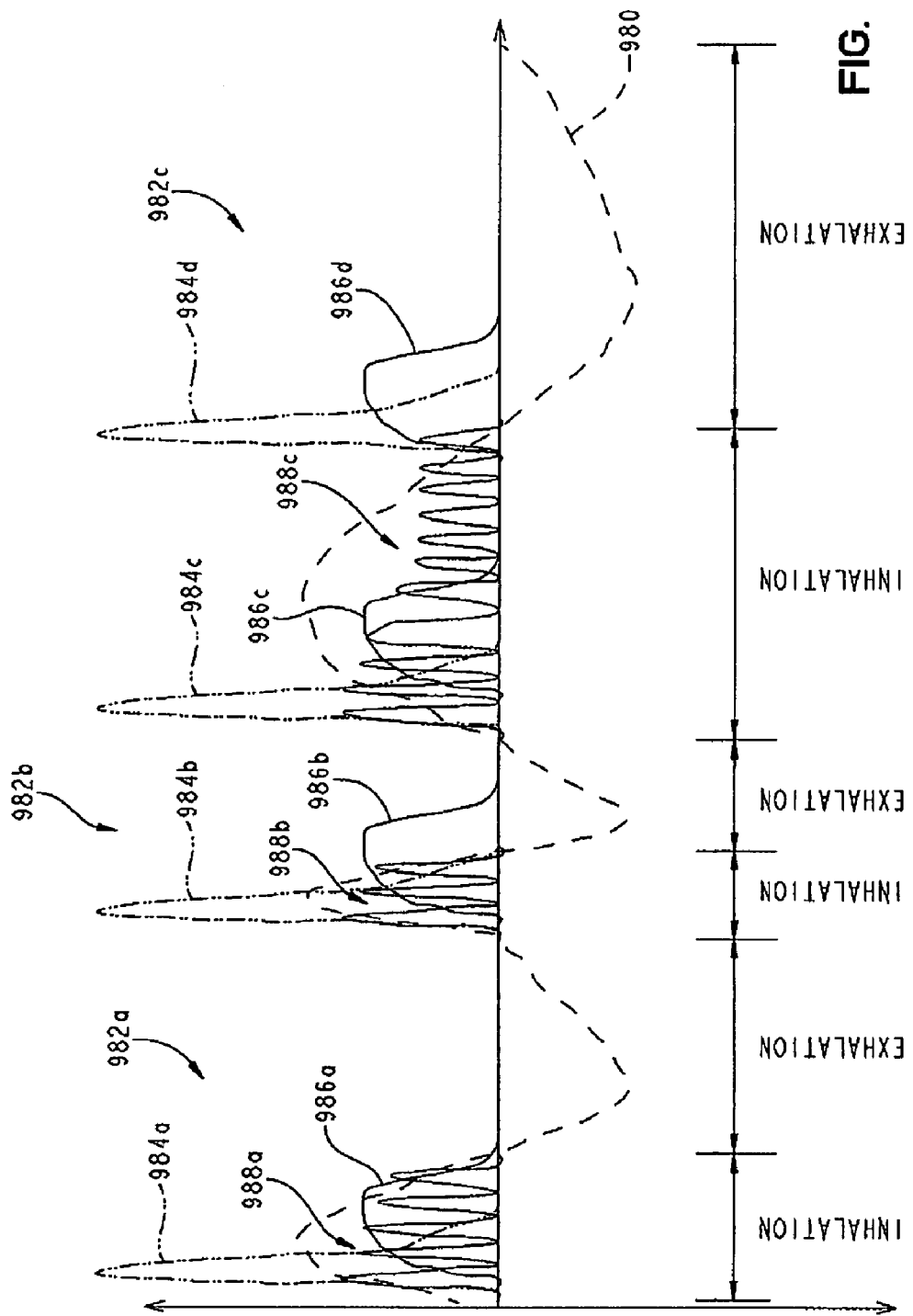

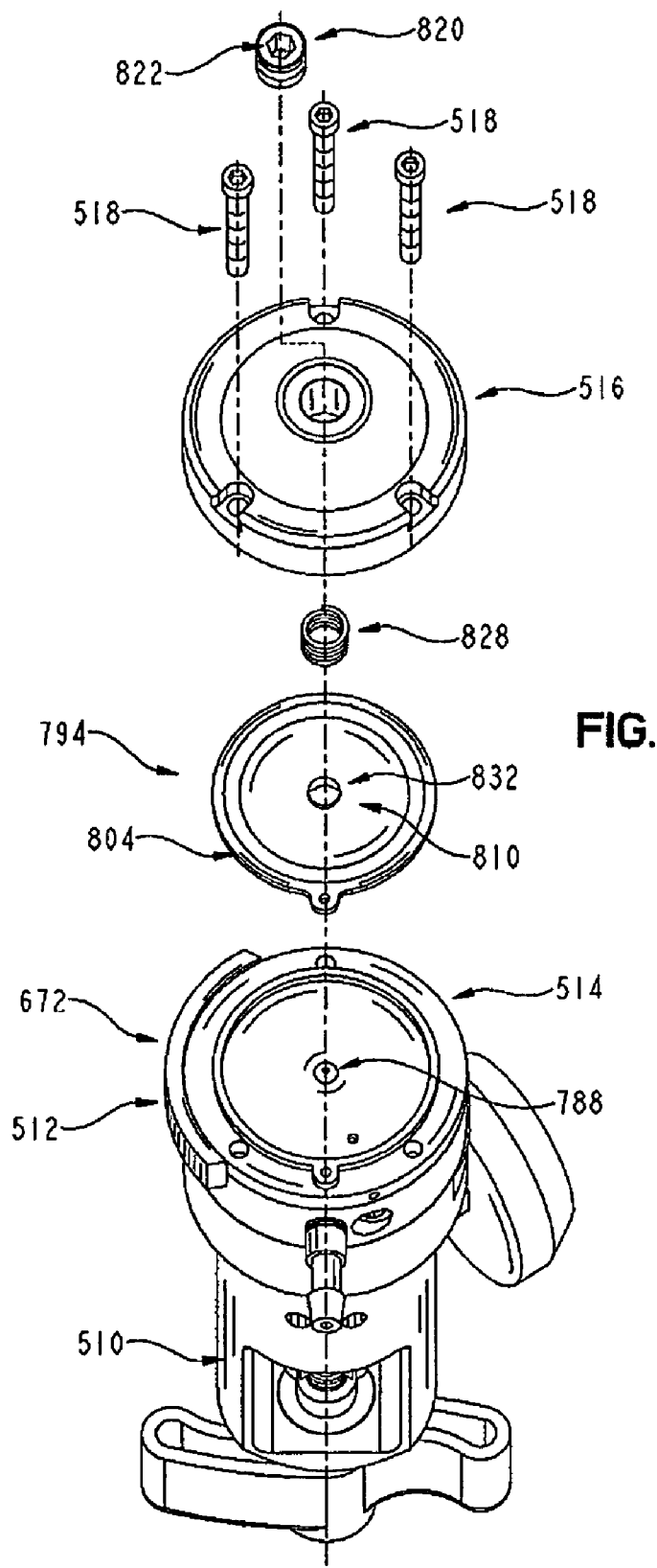

CONSERVER

RELATED APPLICATIONS

This application claims the benefit of U.S. Provisional Patent Application Ser. No. 60/784,216, filed Mar. 20, 2006, titled "MULTI-STAGE COMPRESSOR AND OXYGEN CONCENTRATOR" and U.S. Provisional Patent Application Ser. No. 60/783,243, filed Mar. 17, 2006, titled "ELECTRONIC CONSERVER" and is a continuation-in-part of U.S. patent application Ser. No. 11/724,350, filed Mar. 15, 2007, titled "METHOD AND APPARATUS FOR REGULATING FLUID FLOW OR CONSERVING FLUID FLOW", which claims the benefit of U.S. Provisional Patent Application Ser. No. 60/782,736, filed Mar. 15, 2006, titled METHOD AND APPARATUS FOR REGULATING FLUID FLOW OR CONSERVING FLUID FLOW and is a continuation-in-part of U.S. patent application Ser. No. 11/069,084, filed Feb. 28, 2005 which claims the benefit of U.S. Provisional Patent Application Ser. No. 60/548,058, filed Feb. 26, 2004, titled FLOW REGULATOR; U.S. Provisional Patent Application Ser. No. 60/606,288, filed Sep. 1, 2004, titled METHOD AND APPARATUS FOR REGULATING FLUID FLOW OR CONSERVING FLUID FLOW; and U.S. Provisional Patent Application Ser. No. 60/620,890, titled FLUID REGULATOR, filed Oct. 21, 2004, the disclosures each of which are expressly incorporated by reference herein.

BACKGROUND AND SUMMARY OF THE INVENTION

The present disclosure relates to devices for supplying medical gas, such as oxygen, including devices for attachment to portable tanks of medical gas, regulating the flow of the medical gas, providing a calibrated flow of the fluid in at least either a continuous mode of operation or in an intermittent mode of operation, devices for filling portable tanks of medical gas, and fluid compressors.

Patients with lung diseases frequently need oxygen delivered to their lungs as part of their therapy. In certain known therapies, a continuous flow of oxygen is supplied to a patient. However, a continuous flow is not required at all times, such as when the patient is exhaling. It is also known to provide oxygen conserving devices that supply oxygen to the patient in an intermittent fashion.

It is known to provide patients with a conserving device attached to a portable storage tank of oxygen to increase patient mobility. These devices may be further connected to an oxygen concentrator device or fill device. Exemplary oxygen concentrator or fill devices include those described in U.S. Pat. No. 5,988,165; U.S. Pat. No. 6,152,134; U.S. Pat. No. 6,302,107; U.S. Pat. No. 6,889,726; U.S. Pat. No. 6,805,122; U.S. Pat. No. 6,923,180; the disclosures each of which are expressly incorporated by reference herein. Further exemplary oxygen concentrator devices or fill devices include the DeVilbiss iFill brand personal oxygen station available from Sunrise Medical located at 100 DeVilbiss Drive, Somerset, Pa. 15501, the Total O2 brand delivery system available from Chad Therapeutics, Inc. located at 21622 Plummer Street, Chatsworth, Calif. 91311, and the HomeFill II oxygen filling system available from Invacare Corporation located in Elyria, Ohio.

In an exemplary embodiment of the present disclosure, a pneumatic conserver is provided.

In a further exemplary embodiment of the present disclosure, a conserver which receives a fluid from a source of pressurized fluid and provides fluid to a patient through a single lumen cannula is provided. The conserver comprising: a body having a fluid input, a fluid output adapted to be coupled to a cannula, and a fluid passage configured to connect the input to the output; a pressure reduction section disposed within the body and in fluid communication with the fluid passage, at least one user input supported by the body; and a controller positioned downstream of the pressure reduction section. The pressure reduction section receiving fluid from the fluid inlet of the body at a first pressure and providing fluid to a portion of the fluid passage positioned downstream of the pressure reduction section. The controller having a first configuration to provide a continuous flow of fluid to the fluid outlet of the body in a continuous mode and to provide an intermittent flow of fluid to the fluid outlet of the body in an intermittent mode, the intermittent mode and the continuous mode being selectable by the at least one user input. The conserver further comprising a coupler coupled to the body. The coupler having a fluid conduit in fluid communication with the fluid inlet of the body. The coupler being adapted to couple to a source of pressurized fluid, wherein the coupler is made from a first material selected from the group of a brass based material, a copper based material, and a titanium based material and the body is made from a second material selected from the group of an aluminum based material, a composite based material, and a polymeric based material.

Additional, features of the invention will become apparent to those skilled in the art upon consideration of the following detailed description of illustrative embodiments exemplifying the best mode of carrying out the invention as presently perceived.

BRIEF DESCRIPTION OF THE DRAWINGS

FIG. 1 is a sectional view of an exemplary flow regulator coupled to a source of pressurized fluid and an application device, the flow regulator having a flow selector.

FIG. 2 is a sectional view of the flow regulator of FIG. 1 coupled to a source of pressurized fluid, illustratively a source of pressurized oxygen, and a fluid conserver, illustratively an oxygen conserver.

FIG. 3A is a back view of an exemplary flow selector including a flow restrictor and a knob.

FIG. 3B is a front view of the flow restrictor and knob of the flow selector of FIG. 3A.

FIG. 4A is a sectional view of the exemplary flow selector of FIG. 3A and an associated axle.

FIG. 4B is a sectional view of the flow selector of FIG. 3A and an exemplary associated axle having a central passage.

FIG. 5A is a back view of another exemplary flow selector showing an outer knob portion and an inner flow restrictor having a plurality of flow passages, each one of the fluid passages being configured to provide a calibrated amount of fluid flow and showing a plurality of depressions for receiving a detent member (such as the detent member of FIG. 19) and a central passage for receiving an axle (such as the axle of FIG. 19).

FIG. 5B is a sectional view of the flow selector of FIG. 5A showing a first one of a plurality of flow calibrators positioned within openings in a side wall of the outer knob portion.

FIG. 5C is a front view of the flow selector of FIG. 5A.

FIG. 15A is a comparison of the fluid pulses of three commercial conservers.

FIG. 29 is an exploded isometric view of the third body portion of FIG. 27, the diaphragm assembly of FIG. 28, and the assembly of FIG. 26.

DETAILED DESCRIPTION

Figure 5D:
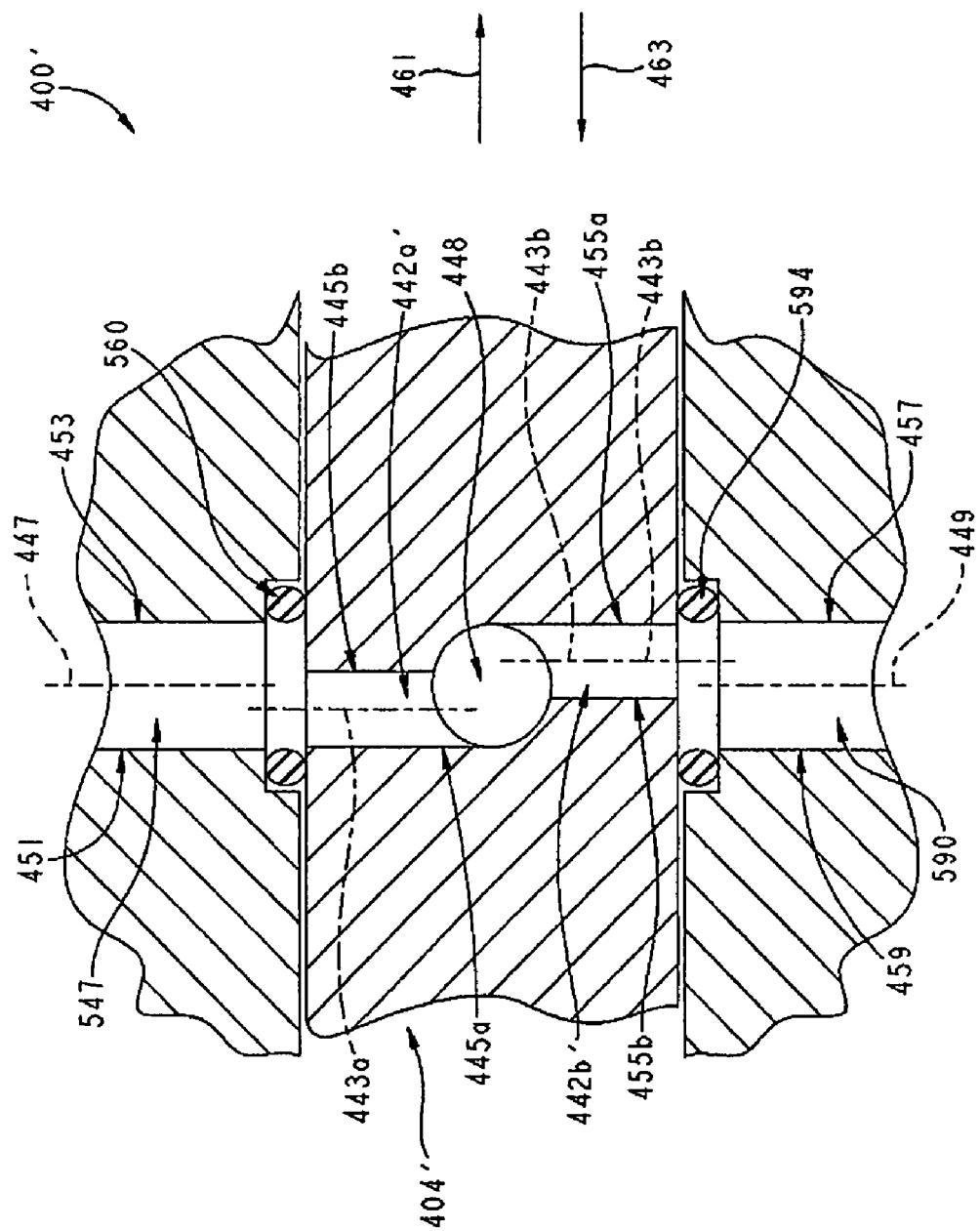
FIG. 5D is a diagrammatic representation of a second exemplary configuration of the fluid passages of the inner flow selector, the fluid passages having a first portion offset from a second portion.

Referring to FIG. 1, a flow regulator 100 is shown. Flow regulator 100 includes a body 102 having a fluid inlet passage 104 and a fluid outlet passage 106. Fluid inlet 104 may be coupled to a source of pressurized fluid 108. Fluid outlet 106 may provide a continuous flow of fluid or may be coupled to an application device 110. Example application devices include fluid conserver devices, fluid regulators, flow control valves, and tubing to transport the fluid. In one embodiment, application device 110 is at least partially contained within body 102. In another embodiment, application device 110 is not contained within body 102.

FIG. 2 illustrates flow regulator 100 of FIG. 1 having fluid inlet passage 104 coupled to a source of pressurized oxygen 109 and fluid outlet passage 106 coupled to an oxygen fluid conserver application device 111. In one embodiment, oxygen conserver 111 is a pneumatic oxygen conserver. An exemplary pneumatic oxygen conserver and variations thereof are shown in FIGS. 10-14 and 16-34. In another embodiment, oxygen conserver 111 is an electronic oxygen conserver.

Referring to FIG. 1, body 102 is shown as a revolved cylinder having a central axis 112. In alternative embodiments, body 102 is another revolved section, includes other revolved sections, is a non-revolved section such as rectangular or square, or a combination of revolved sections and/or non-revolved sections. In one embodiment, body 102 is a one piece housing. In another embodiment, body 102 includes at least two sections which are assembled together.

Fluid inlet passage 104 and fluid outlet passage 106 are shown as being generally cylindrical passageways which are coaxial with central axis 112. In alternative embodiments, fluid inlet passage 104 and/or fluid outlet passage 106 may have other transverse sectional shapes and may be comprised of more complex passageways. For example, fluid outlet passage 106 may comprise a first portion 106a which is coaxial with central axis 112 and a second portion 106b which is perpendicular to central axis 112, first portion 106a and second portion 106b intersecting to form fluid outlet passage 106. Further, fluid inlet passage 104 and fluid outlet passage 106 may have additional components intersecting with the respective one of fluid inlet passage 104 and fluid outlet passage 106. For example, a pressure reduction section, such as pressure reduction section 170 shown in FIG. 7, to reduce the pressure of the fluid received from source 108 or a fluid pressure gauge, such as gauge 334 shown in FIG. 6A, may be interposed in fluid inlet passage 104.

Flow regulator 100 further includes a flow selector 114. Flow selector 114 is coupled to body 102 and includes at least one fluid passage or opening 116 sized to permit a known or calibrated flow rate of fluid to pass from fluid inlet passage 104 to fluid outlet passage 106. Fluid passage 116 provides the known or calibrated flow rate of fluid by restricting the amount of fluid that passes from fluid inlet passage to fluid outlet passage.

As shown in FIG. 1, flow selector 114 is rotatably coupled to body 102 and is rotatable about an axis 117 in directions 118, 120. Axis 117 is generally parallel with central axis 112 and offset from central axis 112. In the illustrated embodiment, flow selector 114 includes a plurality of openings 116, openings 116a and 116b being shown. Preferably openings 116a and 116b are sized to permit different known or calibrated flow rates of fluid to pass from fluid inlet passage 104 to fluid outlet passage 106 such that by rotating flow selector 114 in one of directions 118, 120 the operator may select a first known or calibrated flow rate from a plurality of known or calibrated flow rates.

In one embodiment, a surface 122 of flow selector 114 is accessible from the exterior of body 102. Preferably, surface 122 is raised relative to a surface 124 of body 102 such that a user can easily locate flow selector 114 and impart a rotation to flow selector 114 in one of directions 118, 120. Even though surface 122 of flow selector 114 is raised relative to surface 124 of body 102, flow selector 114 is substantially within an envelope of body 102 defined by surface 124. In alternative embodiments, surface 122 is generally flush with surface 124 (touching the envelope of body 102) or recessed relative to surface 124 (within the envelope of body 102). In one embodiment, surface 122 is textured, such as a knurled surface, to aid in gripping.

In one embodiment, flow selector 114 includes a detent (not shown) that aids the user in aligning one of the plurality of openings 116 with fluid inlet passage 104 and fluid outlet passage 106. The detent biases the flow selector 114 to a rotational position corresponding to the alignment of one of the plurality of openings 116 with fluid inlet passage 104 and fluid outlet passage 106

Referring to FIGS. 3 and 4, an exemplary flow selector 200 is shown. Flow selector 200 includes a knob 202, a flow restrictor 204, and a seal 206 (see FIG. 4A) positioned between knob 202 and flow restrictor 204. Knob 202 includes a recess 208 sized to receive flow restrictor 204. Recess 208 includes a key member 209 (see FIG. 3A) which is received by key slot 210 (see FIG. 3A) of flow restrictor 204. Key member 209 and key slot 210 cooperate to align flow restrictor 204 relative to knob 202 such that fluid passages 214 in knob 202 are aligned with fluid passages 216 in flow restrictor 204.

It should be appreciated that knob 202 and flow restrictor 204 may be made as an integral component thereby obviating the need for seal 206. However, by having flow restrictor 204 and knob 202 be separate components, different flow restrictors 204 may be used with knob 202 to provide greater flexibility in the range of flow rates flow selector 200 is configured to generate.

In one embodiment, flow restrictor 204 is press fit into recess 208 of knob 202. In another embodiment, flow restrictor 204 is coupled to knob 202 by a coupler (not shown). In still another embodiment, flow restrictor 204 and knob 202 are each press fit onto an axle 220. If flow restrictor 204 and knob 202 are press fit onto axle 220, axle 220 is rotatably coupled to body 102 such that axle 220 and flow selector 200 are rotatable about axis 117 in directions 118, 120. In another embodiment, flow selector 200 is rotatable relative to axle 220 and axle 220 is fixably coupled to body 102.

Referring to FIG. 4A, knob 202 includes a first radial extent defined generally by first outer surface 222 and a second radial extent defined generally by second outer surface 224. First outer surface 222 is configured to be gripped by a user such that the user is able to impart a rotation of flow selector 200 about axis 117 in one of directions 118, 120. In one embodiment, first outer surface 222 is textured, such as knurled, to facilitate the gripping of surface 222 by a user.

In one embodiment, knob 202 including surface 222 is made from aluminum. In other examples, knob 202 including surface 222 is made from brass or other suitable materials. In another embodiment, knob 202 is made from a first material, such as aluminum, brass, or a thermoplastic material, and surface 222 is made of a different second material, the second material aiding in the gripping of surface 222. In one example, knob 202 is made of thermoplastic material, such as ABS, and surface 222 is made from a rubber material. Surface 222 is created by molding the base of knob 202 out of ABS and coupling the rubber material to the ABS material. In one example, the ABS knob is an insert in a mold and the rubber material is molded over the ABS knob.

Second outer surface 224 has a smaller diameter than first outer surface 222. Second outer surface 224 is configured to include indicia (not shown) indicating which pair of passages 214 and respective passage 216 are aligned with fluid inlet 104 and fluid outlet 106 and therefore to indicate the selected flow rate. In one example, indicia are molded onto surface 224. In a further example, the indicia are embossed. In another example, the indicia are recessed. In yet another example, the indicia are painted or otherwise applied to surface 224, such as with one or more stickers.

It should be appreciated that any suitable indicia may be used, such as lines, numbers, or letters. In one example, body 102 includes indicia on surface 124, such as a line or a plurality of numbers. The user of flow regulator 100 aligns the appropriate indicia of flow selector 200 with the indicia on body 102 to select the respective flow rate. In one example, body 102 includes a line as an indicia and flow selector 200 includes a plurality of numbers, each number corresponding to a respective flow rate, such that by aligning a number on flow selector 200 with the line on body 102 results in the corresponding passages 214 and 216 being aligned with fluid inlet 104 and fluid outlet 106. In another example, body 102 includes a plurality of numbers as an indicia and flow selector 200 includes a line, such that by aligning the line of flow selector 200 with a number on body 102 results in the corresponding passages 214 and 216 being aligned with fluid inlet 104 and fluid outlet 106. In still a further example, body 102 includes a window, such as window 380 shown in FIG. 11 and flow selector 200 includes a plurality of numbers, such as number 2 shown in FIG. 11, such that aligning a number of flow selector 200 with the window on body 102 results in the corresponding passages 214 and 216 being aligned with fluid inlet 104 and fluid outlet 106.

Referring to FIG. 4A, knob 202 further includes a seat 230 sized to receive seal 206. Seal 206 is inserted into recess 208 of knob 202 such that a first side 236 of seal 206 contacts step 230 of knob 202. Next, flow restrictor 204 is inserted into recess 208 such that a first end 240 of flow restrictor 204 contact a second side 238 of seal 206.

Seal 206 includes a plurality openings 232 each located to correspond to one of passages 214 of knob 202 and the respective one of passages 216 of flow restrictor 204. It should be noted that openings 232 do not overlap, but are separated by a land (not shown). As such, seal 206 prevents fluid escaping from a respective pair of passages 214, 216 to another one of passages 214, 216.

Referring to FIGS. 3A, 3B, and 4A, an exemplary embodiment of flow restrictor 204 is shown. In one embodiment, flow restrictor 204 is made from brass. The illustrated embodiment of flow resistor 204 includes seven fluid passages, 216a-g, each one corresponding to a respective flow rate. In one embodiment, the passages 216 are arranged in order of increasing flow rates. For example, passage 216a corresponds to a flow rate of 0.5 liters of fluid per minute (lpm), passage 216b corresponds to a flow rate of 1.0 lpm, passage 216c corresponds to a flow rate of 2.0 lpm, passage 216d corresponds to a flow rate of 3.0 lpm, passage 216e corresponds to a flow rate of 4.0 lpm, passage 216f corresponds to a flow rate of 5.0 lpm, and passage 216g corresponds to a flow rate of 6.0 lpm.

Referring to FIG. 4A, each passage 216 includes a first portion 242 and a second portion 244 including an orifice 246. Each orifice 246 is sized to correspond to the flow rate of the respective passage 216. In the illustrated embodiment, first portion 242 has a larger radial extent than second portion 244. In another embodiment, first portion 242 and second portion 244 have the same radial extent.

Figure 19:
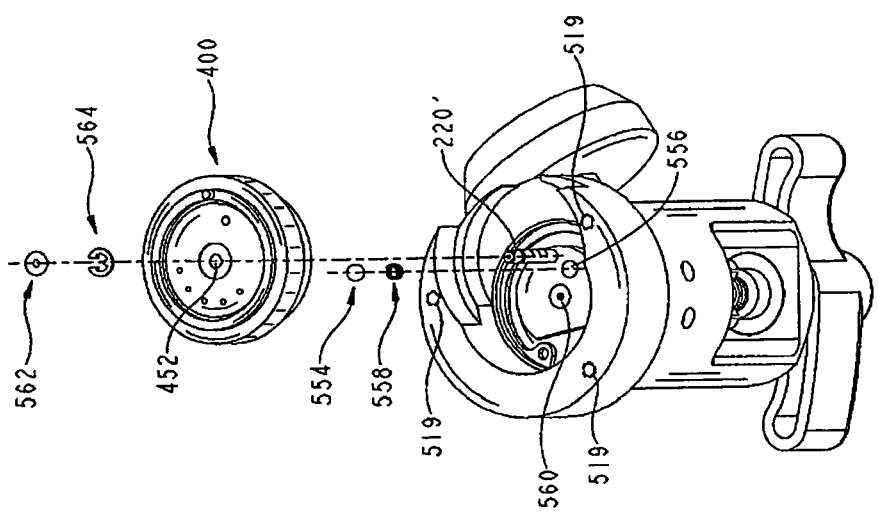
FIG. 19 is an exploded isometric view of the body portion of the flow regulator of FIG. 17 with the pressure reduction assembly of FIG. 16 assembled thereto and a detent, a biasing member, the flow selector of FIG. 5A, a retainer for the flow selector and associated seal.

Referring to FIGS. 3A and 4A, flow restrictor 204 includes a plurality of indexes or recesses 250 which cooperate with a detent, such as ball 554 in FIG. 19. Indexes 250 are positioned such that each one corresponds to the alignment of a respective combination of passage 214 and passage 216 with fluid inlet passage 104 and fluid outlet passage 106. In another embodiment, indexes 250 are bumps which cooperate with depressions on body 102.

Figure 6A:
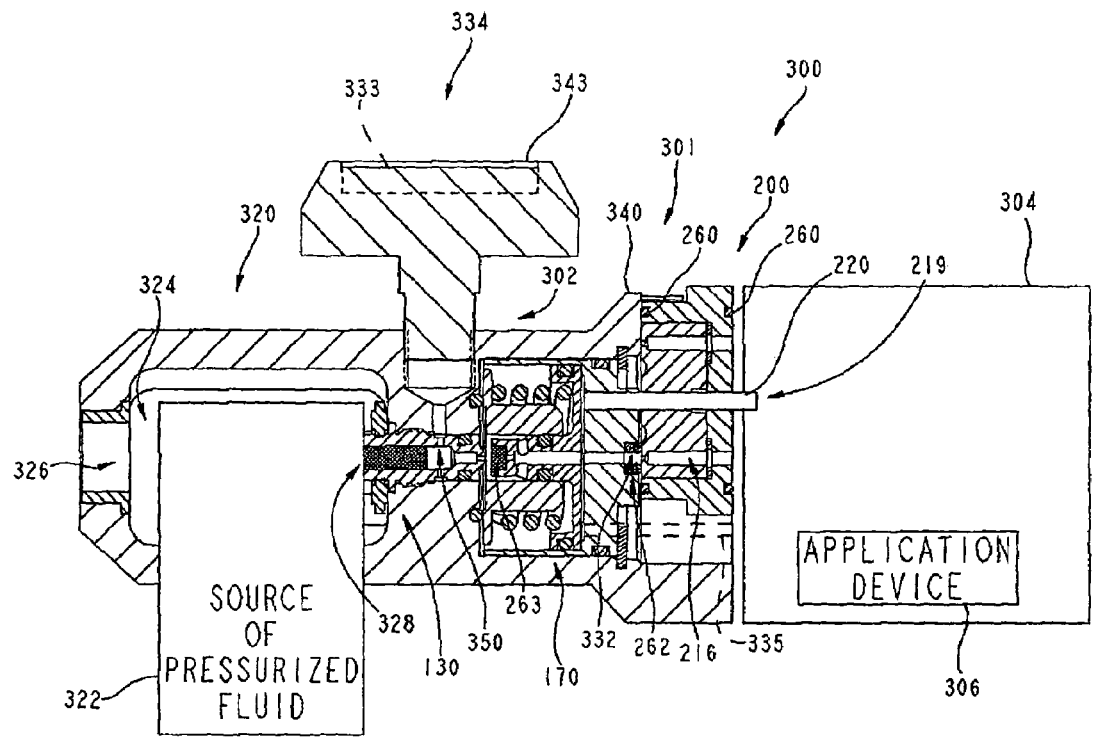
FIG. 6A is a sectional view of an exemplary flow regulator incorporating the flow selector of FIG. 3A and an exemplary fluid inlet retainer and pressure reduction section, the flow regulator being coupled to a source of pressurized fluid and an application device.

Referring to FIG. 4A, knob 202 further includes a recess 256 and a recess 258, each sized to receive a seal 260 (see FIG. 6A). Seal 260 generally seals the region between knob 202 and body 102 to prevent dust or other particles from entering flow regulator 100. In one embodiment, seal 260 is made from a polymeric material, such as Teflon or Kel-F. Additional seals may be provided to provide a fluid tight seal between fluid inlet passage 104 and flow selector 200 and fluid outlet passage 106 and flow selector 200. For example, o-ring seals 262 are shown in FIG. 6A positioned between fluid inlet passage 104 and flow selector 200.

Referring to FIG. 4B, an alternative axle 220' is shown assembled with knob 202 resulting in flow selector 200'. Axle 220' differs from axle 220 of FIG. 3A in that axle 220' includes a central passage 221 for transporting fluid. Therefore, a second fluid inlet passage (not shown) may be coupled to a first end 223 of axle 220' and a second fluid outlet passage (not shown) may be coupled to a second end 225 of 220' to provide a second flow of fluid through central passage 221 which bypasses flow passages 216 in flow restrictor 204. As such, the combination of flow selector 200 and axle 220' permits a metered or restricted flow of fluid based the calibration of respective passages 214 and 216 through flow selector 200 and a second flow of fluid through central passage 221 of axle 220' which bypasses flow passages 214 and 216. Example uses for the second flow of fluid include providing a continuous flow line to the patient, such as for a fluid conserver, and/or to provide a fluid supply for the operation of an application device, such as providing pressure to one side of a diaphragm of a pneumatic fluid conserver application device.

Referring to FIGS. 5A-5C another exemplary embodiment of a flow selector 400 is shown. Flow selector 400 is generally similar to flow selector 200 and includes a knob 402 and a flow restrictor 404. Knob 402 includes an opening 408 sized to receive flow restrictor 404. Opening 408 may include a key member (not shown) which is received by key slot (not shown) of flow restrictor 404. Key member (not shown) and key slot (not shown) cooperate to align flow restrictor 404 relative to knob 402 such that indicia on knob 402 are aligned with flow restrictor 404.

Unlike knob 202, knob 402 does not include a plurality of fluid passages. As such, a seal is not required between knob 402 and flow restrictor 404. It should be appreciated that knob 402 and flow restrictor 404 may be made as an integral component. However, by having flow restrictor 404 and knob 402 be separate components, different flow restrictors 404 may be used with knob 402 to provide greater flexibility in the range of flow rates flow selector 400 is configured to generate.

In one embodiment, flow restrictor 404 is press fit into opening 408 of knob 402. In another embodiment, flow restrictor 404 is coupled to knob 402 by a coupler (not shown). In still another embodiment, flow restrictor 404 is press fit onto an axle, such as axle 220 or axle 220' and knob 402 is press fit onto flow restrictor 404. If flow restrictor 404 and knob 402 are press fit onto an axle, such as axle 220 or axle 220', then axle 220 or 220' is rotatably coupled to body 102 such that axle 220 or 220' and flow selector 400 are rotatable about axis 117 in directions 118, 120. In another embodiment, flow selector 400 is rotatable relative to axle 220 or axle 220' and axle 220 or axle 220' is fixably coupled to body 102.

Knob 402 similar to knob 202 includes a first radial extent defined generally by first outer surface 422 and a second radial extent defined generally by second outer surface 424. First outer surface 422 is configured to be gripped by a user such that the user is able to impart a rotation of flow selector 400 such as about axis 117 in one of directions 118, 120 when flow selector 400 is used with body portion 102. In one embodiment, first outer surface 422 is textured, such as knurled, to facilitate the gripping of surface 422 by a user.

In one embodiment, knob 402 including surface 422 is made from aluminum. In other examples, knob 402 including surface 422 is made from brass or other suitable materials. In another embodiment, knob 402 is made from a first material, such as aluminum, brass, or a thermoplastic material, and surface 422 is made of a different second material, the second material aiding in the gripping of surface 422. In one example, knob 402 is made of thermoplastic material, such as ABS, and surface 422 is made from a rubber material. Surface 422 is created by molding the base of knob 402 out of ABS and coupling the rubber material to the ABS material. In one example, the ABS knob is an insert in a mold and the rubber material is molded over the ABS knob.

Second outer surface 424 has a smaller diameter than first radial surface 422. Second outer surface 424 is configured to include indicia, such as indicia 509 in FIG. 11, indicating which of passages 416 of flow restrictor 404 are aligned with fluid inlet 104 and fluid outlet 106 and therefore to indicate the selected flow rate. In one example, indicia are molded onto surface 424. In another example, the indicia are embossed. In yet another example, the indicia are recessed. In a further example, the indicia are painted or otherwise applied to surface 424, such as with one or more stickers.

It should be appreciated that any suitable indicia may be used, such as lines, numbers, or letters. In one example, body 102 includes indicia on surface 124, such as a line or a plurality of numbers. The user of flow regulator 100 aligns the appropriate indicia of flow selector 400 with the indicia on body 102 to select the respective flow rate. In one example, body 102 includes a line as an indicia and flow selector 400 includes a plurality of numbers, each number corresponding to a respective flow rate, such that by aligning a number of flow selector 400 with the line on body 102 results in the corresponding passage 414 being aligned with fluid inlet 104 and fluid outlet 106. In another example, body 102 includes a plurality of numbers as an indicia and flow selector 400 includes a line, such that by aligning the line of flow selector 400 with a number on body 102 results in the corresponding passage 416 being aligned with fluid inlet 104 and fluid outlet 106. In still a further example, body 102 includes a window, such as window 380 shown in FIG. 11 and flow selector 400 includes a plurality of numbers, such as number 2 shown in FIG. 24, such that aligning a number of flow selector 400 with the window on body 102 results in the corresponding passage 416 of flow restrictor 404 being aligned with fluid inlet 104 and fluid outlet 106.

Referring to FIGS. 5A, 5B, and 5C, an exemplary embodiment of flow restrictor 404 is shown. In one embodiment, flow restrictor 404 is made from brass. The illustrated embodiment of flow resistor 404 includes five fluid passages, 416a-e in FIGS. 5A-C, each one corresponding to a respective flow rate. In another embodiment, flow restrictor 404 includes six fluid passages 416. As stated above in connection with flow restrictor 204, multiple fluid passages 416 are configured to provide different flow rates. In one embodiment, fluid passages 416 are arranged in increasing order of flow rates. For example, passage 416a corresponds to a flow rate of 0.5 lpm, passage 416b corresponds to a flow rate of 1.0 lpm, passage 416c corresponds to a flow rate of 2.0 lpm, passage 416d corresponds to a flow rate of 3.0 lpm, and passage 416e corresponds to a flow rate of 4.0 lpm.

In one embodiment, flow restrictor 404 includes orifices sized to correspond to the flow rate of the respective passage 416 (similar to flow restrictor 204). Referring to FIG. 5B, in the illustrated embodiment, each passage 416 of flow restrictor 404 includes a first portion 442 and a second portion 444. First portion 442 permits the flow of fluid when aligned with fluid inlet 104 and fluid outlet 106 to pass from a first side 441 of flow restrictor 404 to a second side 443 of flow restrictor 404.

Second portion 444 intersects with first portion 442 and is shown perpendicular to first portion 442. In other examples, second portion 444 forms an acute angle with first portion 442. Second portion 444 is sized to receive an occluder or flow calibrator 446. Occluder 446 is configured to at least partially intersect with first portion 442 and to reduce a cross-sectional area of first portion 442. By reducing the cross-sectional area of first portion 442, occluder or flow calibrator 446 controls the corresponding flow rate of respective passage 416 for fluid flowing from first side 441 to second side 443.

In the illustrated embodiment, occluder 446 is a spherical occluder or ball 448. Ball 448 is press fit into second portion 444 with a tool (not shown). The tool advances ball 448 into second portion 444 and ultimately into first portion 442 to a position wherein the resultant cross-sectional area of first portion 442 corresponds to the desired flow rate for the respective passage 416. It should be noted that passage 416 includes a recess 449 configured to receive a portion of ball 448 when ball 448 is further advanced by the tool. Ball 448 and second portion 444 generally form a tight seal so that fluid does not pass by ball 448 and through second portion 444. Other types of occluders may be used, such as needle valves inserted in second portion 444.

In one exemplary method, flow restrictor 404 is positioned in a fixture (not shown) and aligned with a fluid inlet and a fluid outlet such that a flow of fluid is passing through passage 416. The flow rate of passage 416 being monitored by a detector as is well know in the art. The tool then slowly advances ball 448 in second portion 444 until the monitored flow rate drops to the corresponding desired or calibrated flow rate for passage 416 indicating that the correct cross-sectional area of first portion 442 has been achieved.

In one embodiment ball 448 is inserted from one of sides 441, 443 of flow restrictor 404 to at least partially occlude the flow of passage 416. U.S. Pat. No. 4,366,947 to Voege ("Voege") and U.S. Provisional Patent Application Ser. No. 60/620,890, filed Oct. 21, 2004, titled "A FLUID REGULATOR", ("'890 application"), both provide at least one exemplary embodiment of occluding flow by the insertion of a ball type occluder into a passage from an axial face of a flow restrictor. Both Voege and the '890 application are expressly incorporated by reference herein. It should be noted that the occlusion methods shown in both Voege and in the '890 application introduces a bend into the fluid flow path through flow restrictor 404 such that flow passage 416 is non-linear.

Referring to FIG. 5A, flow restrictor 404 includes a plurality of indexes or recesses 450 which cooperate with a detent, such as ball 554 in FIG. 19. Indexes 450 are positioned such that each one corresponds to the alignment of a respective fluid passage 416 with fluid inlet passage 104 and fluid outlet passage 106. In another embodiment, indexes 450 are bumps which cooperate with depressions on body 102.

Referring to FIG. 5D, a diagrammatic representation of a modified flow restrictor 404' is shown. Flow restrictor 404' is generally the same as flow restrictor 404 except that first portion 442' of flow restrictor 404' includes a first section 442a' and a second section 442b' offset from first section 442a'. In flow restrictor 404, first portion 442 is generally positioned along a single axis, not along two axes. In flow restrictor 404', first section 442a' and second section 442b' are positioned along two separate axes 443a, 443b, respectively. During normal operation, one of fluid passage 104 (see FIG. 1) or 547 and fluid passage 106 (see FIG. 1) or 590 is in fluid communication with section 442a' and the other of fluid passage 104 or 547 and fluid passage 106 or 590 is in fluid communication with section 442b' during normal operation. However, as shown in FIG. 5D axis 443a of fluid section 442a' is not aligned with an axis 447 of fluid passage 547 and axis 443b of fluid section 442b' is not aligned with axis 449 of fluid passage 590. In the illustrated embodiment, axis 447 and axis 449 are aligned.

The relationship of first section 442a', second section 442b', fluid passage 547, and fluid passage 590 is such that one of the first section 442a' and second section 442b' is shut off from its respective fluid passage of fluid passages 547, 590 prior to the other of first section 442a' and second section 442b' during the rotation of flow restrictor 404'. A first side 445a of fluid section 442a' is generally positioned proximate a first side 451 of fluid passage 547 while a second side 445b of fluid section 442a' is generally positioned further offset from second side 453 of fluid passage 547 than first side 445a is from first side 451. A first side 455a of fluid section 442b' is generally positioned proximate a first side 457 of fluid passage 590 while a second side 455b of fluid section 442b' is generally positioned further offset from a second side 459 of fluid passage 590 than first side 455a is from first side 457.

Referring to FIG. 5D, a clockwise rotation of flow restrictor 404', generally denoted by direction 461, results in fluid section 442b' being shut off from fluid passage 590 prior to fluid section 442a' being shut off from fluid passage 547. A counterclockwise rotation of flow restrictor 404', generally denoted by direction 463, results in fluid section 442a' being shut off from fluid passage 547 prior to fluid section 442b' being shut off from fluid passage 590.

When axle 220' is used with flow selector 400 or 400' a second fluid inlet passage 548 (shown in FIG. 14) may be coupled to a first end 223 of axle 220' and a second fluid outlet passage 618 (shown in FIG. 14) may be coupled to a second end 225 of 220' to provide a second flow of fluid through central passage 221. As such, the combination of flow selector 400 or 400' and axle 220' permits a metered or calibrated flow of fluid through flow selector 400 or 400' and a second flow of fluid through central passage 221 of axle 220'. Example uses for the second flow of fluid include providing a continuous flow line to the patient, such as for a fluid conserver application device, and/or to provide a fluid supply for the operation of an application device, such as providing pressure to one side of a diaphragm of a pneumatic fluid conserver application device.

Figure 6B:
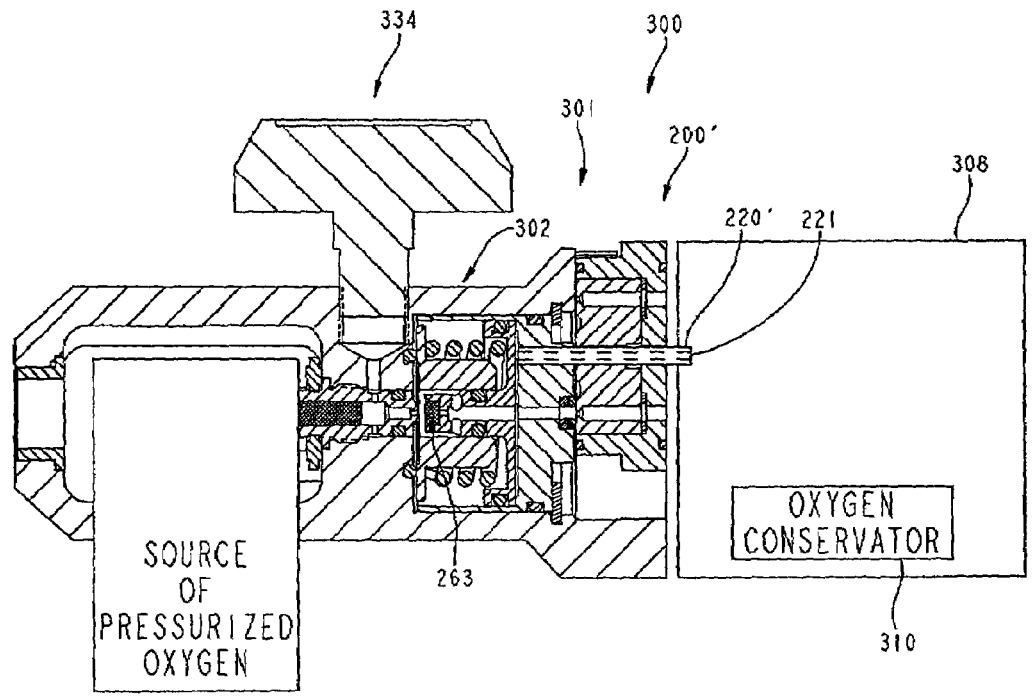
FIG. 6B is a sectional view of the flow regulator of FIG. 6A coupled to an oxygen conserver.

Referring to FIG. 6A, a flow regulator 300 including a body 301 and flow selector 200 is shown. It should be understood that one of flow selector 200'; 400, 400' can be used in place of flow selector 200. Flow selector 200 is rotatably coupled to a first portion 302 of body 301. Illustratively, flow selector 200 is coupled to body portion 302 through axle 220 and the internal components of flow regulator 300, such as a pressure reduction section 170. A second portion 304 of body 301 is coupled to the first portion 302 of body 301. In one example, a second portion 304 includes an application device 306. In another example, as shown in FIG. 6B a second portion 308 of body 301 includes an oxygen conserver application device 310. In the illustrated embodiment, first portion 302 is coupled to a first end 217 of axle 220 and respective second portion 304, 308 is coupled to a second end 219 of axle 220. In another embodiment axle 220 is coupled to only one of first portion 302 and respective second portion 304, 308.

Figure 6C:
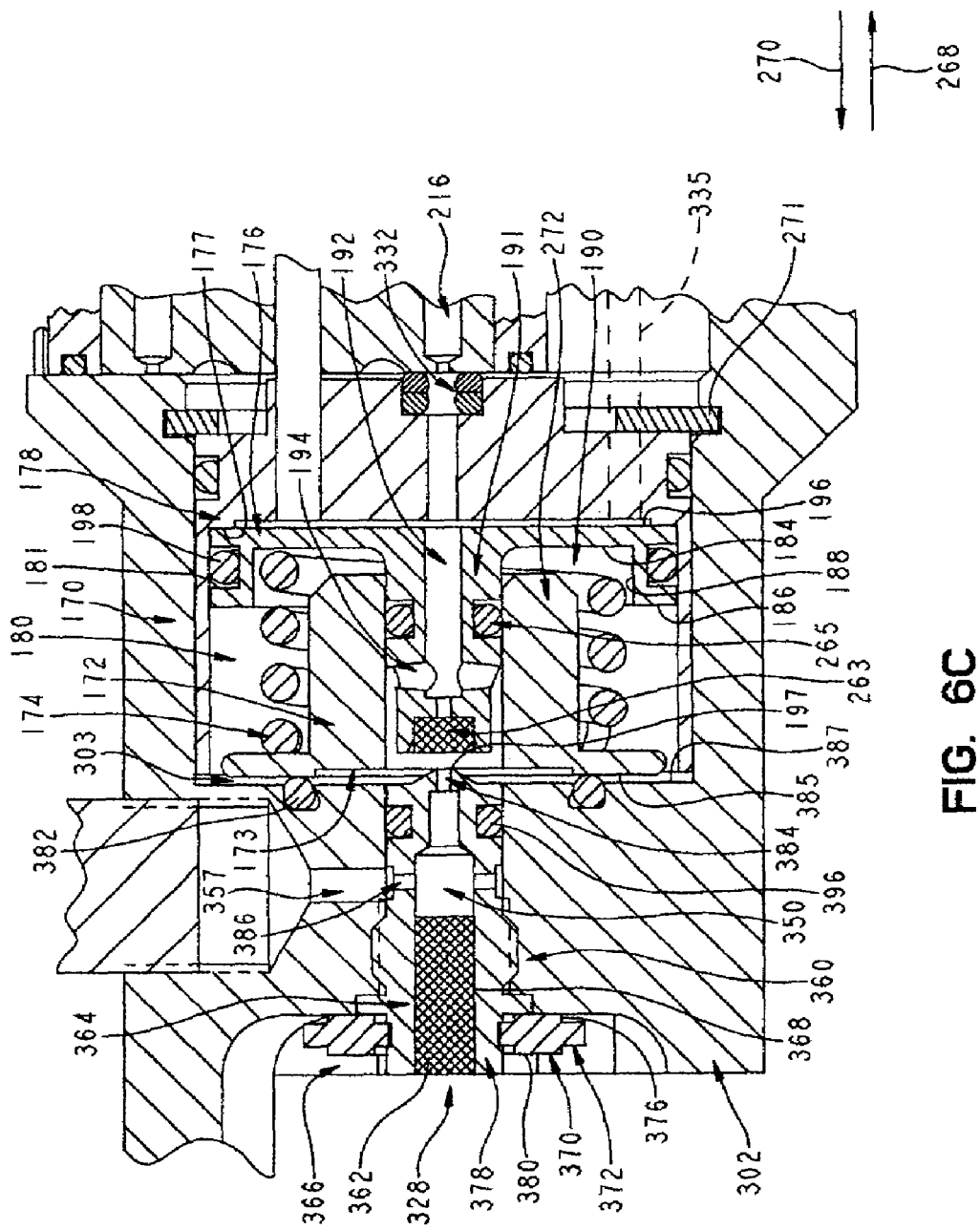
FIG. 6C is an enlarged view of the exemplary fluid inlet retainer and pressure reduction section of FIG. 6A.

It should be noted that FIGS. 6A-6C are provided to better illustrate the operation of flow regulator 300 and that FIGS. 6A-6C are not intended to be a single cross-section through flow regulator 300 but rather to illustrate various features of the various components of flow regulator 300.

As shown generally in FIGS. 6A, 6B, flow selector 200 is generally positioned within body 302 with a portion of knob 202 being raised above an outer surface 340 of body 302. As such, knob 202 is able to be gripped by a user to adjust the combination of passages 214, 216 which are in communication with fluid inlet 332. However, flow selector 200 does not appreciably enlarge the envelope of flow regulator 300. As such, in one example flow selector 200 is rotatable about an axis offset from the central axis of body 302 but is still substantially within the envelope of flow regulator 300. In another example, flow selector 200 is rotatable about an axis offset from the central axis of body 302 and is completely within or just touching the envelope of flow regulator 300. It should be understood that one of flow selector 200'; 400, 400' can be used in place of flow selector 200.

Figure 9:
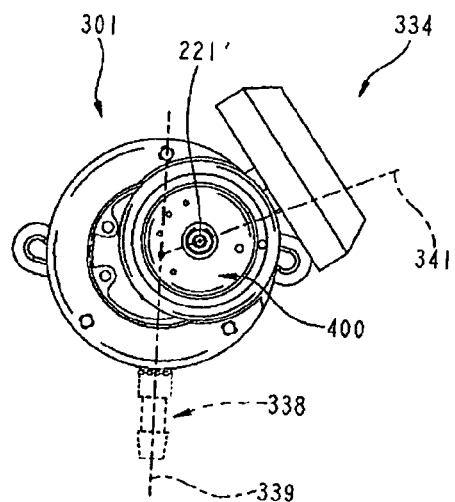
FIG. 9 is an end view of the flow regulator of FIG. 6A including the flow selector of FIG. 5A and an axle with a central fluid passage.
Figure 11:
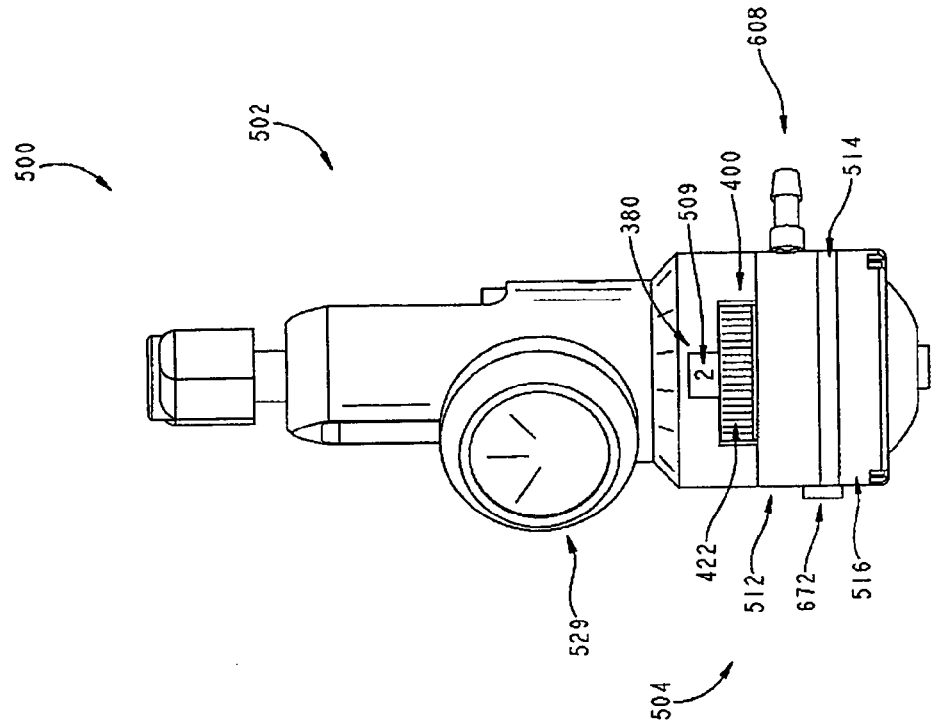
FIG. 11 is a side isometric view of the conserving device of FIG. 10 showing a thumb wheel for selecting a predetermined flow rate and a pressure gauge.

Referring to FIG. 9, using an axis 339 of nipple 338 as a reference, an axis 341 intersecting with fluid inlet passage 332 and axle 220 is generally 67° from axis 339. Such orientation is preferred. In another embodiment, axis 341 is generally at another angle from axis 339. Flow selector 400 is illustrated in FIG. 9. However, it should be understood that one of flow selectors 200, 200', 400' can be used in place of flow selector 400.

Returning to FIG. 6A, body 302 illustratively includes a yoke 320 configured to couple a source of pressurized fluid 322 to flow regulator 300. In an exemplary embodiment, yoke 320 includes an opening 324 sized to receive a post valve (not shown) and a threaded aperture 326 sized to threadably receive a retainer (not shown). As is known in the art, the retainer urges a fluid outlet of the post valve into engagement with a fluid inlet 328 of flow regulator 300 such that fluid is communicated to flow regulator 300 from the source of pressurized fluid.

Fluid from the source of pressurized fluid 322 enters fluid inlet 328 and is communicated to pressure reduction section 170 which is configured to provide a lower pressure, such as about 5 psi, about 15 psi, about 20 psi, about 22 psi, about 27 psi, about 50 psi, about 60 psi, and the range of about 5 psi to about 60 psi, to a fluid inlet passage 332. This lower pressure is established as a fixed reduced pressure by the particular configuration of the components of pressure reduction section 170 selected for the desired lower pressure output. Fluid in fluid inlet passage 332 is communicated to one of the combination passages 214, 216 through flow selector 200 to provide a metered or calibrated fluid flow to a fluid outlet passage (not shown). Fluid from fluid inlet passage 328 is also provided to a fluid pressure gauge 334 to provide a reading of the pressure in the source of pressurized fluid 322.

Fluid inlet 328 includes a fluid conduit 350 through a fluid inlet retainer 360. Referring to FIG. 6C, fluid inlet retainer 360 includes at least one filter 362, a filter retainer 364, and a seal ring 366. Filter retainer 364 is threadably received within a central opening in body portion 302. Filter retainer 364 includes fluid conduit 350 which has an enlarged portion 368 for receiving one or more filters 362. Filters 362 remove impurities from the fluid, such as from oxygen. In one example, filters 362 are designed to filter particles which are about 0.66 microns or larger.

In one embodiment, two filters are positioned within enlarged portion 368. In another embodiment, three filters are positioned within enlarged portion 368. Exemplary filters include sintered bronze filters having a length of about 0.188 inches and a diameter of about 0.130 inches or filters made from other materials which will not ignite in the presence of oxygen flowing there through at relatively high pressures, such as about 500 to about 3000 psi. In one example filter retainer 364 is made from brass. In alternative embodiment, filter retainer 364 is made from other materials which will not ignite in the presence of oxygen flowing there through at relatively high pressures.

Seal ring 366 includes a seal 370 and a support 372. In one example, seal 370 is made of a flouroelastomer, Viton®, having a durometer of about 75 and support 372 is made of brass. Seal 370 is received within a central opening in support 372 and axially extends outward beyond the axial surfaces of support 372. Seal ring 366 is positioned over filter retainer 364 such that a first portion 376 of seal 370 contacts one of body 302 or filter inlet retainer 364 and such that a top portion 378 of filter inlet retainer 364 extends axially beyond a second portion 380 of seal 370.

First portion 376 of seal 370 provides a seal between one of body 302 and filter retainer 364 and support 372 when the source of pressurized fluid is coupled to flow regulator 300. Second portion 380 of seal 370 provides a seal between support 372 and the source of pressurized fluid when the source of pressurized fluid is coupled to flow regulator 300. As such, when the source of pressurized fluid is coupled to flow regulator 300, seal ring 366 prevents or at least minimizes the passage of fluid from the source of pressurized fluid to anywhere (such as atmosphere) other than fluid conduit 350 of fluid inlet retainer 360.

Fluid conduit 350 is generally shown as a central longitudinal conduit and includes a fluid outlet 384 (see FIG. 6A). The diameter of fluid outlet 384 is generally reduced relative to the diameter of enlarged portion 368 which receives filter 362. In one example, a diameter of fluid outlet 384 is about 0.029 inches. Fluid which passes through filters 362 passes through fluid outlet 384 and is presented to pressure reduction section 170.

Referring to FIG. 6C, fluid inlet retainer 360 further includes at least one radial fluid conduit 386 which is in fluid communication with fluid conduit 350. When fluid inlet retainer 360 is coupled to body portion 102 radial fluid conduit 386 is in fluid communication with a radial passageway 357 in body portion 302. Passageway 357 is in fluid communication with a recess in body portion 302 which is designed to threadably receive pressure gauge 334. Referring to FIG. 6A, pressure gauge 334 includes a face 333 visible through a window 343 which includes indicia to provide an operator with an indication of the pressure of the fluid in the source of pressurized fluid. In one example, the window is made of Lexan. Gauge 334 includes a protective outer member. In one example, the protective outer member is made of rubber.

Returning to FIG. 6C, fluid from radial fluid conduit 384 is prevented from passing to atmosphere adjacent fluid inlet 328 due to seal 370 of seal ring 366 and is prevented from entering cavity 303 in body portion 302 due to seal 396 received by a groove on filter retainer 364 and positioned between filter retainer 364 and the channel in body portion 302 which receives filter retainer 364.

Figure 7:
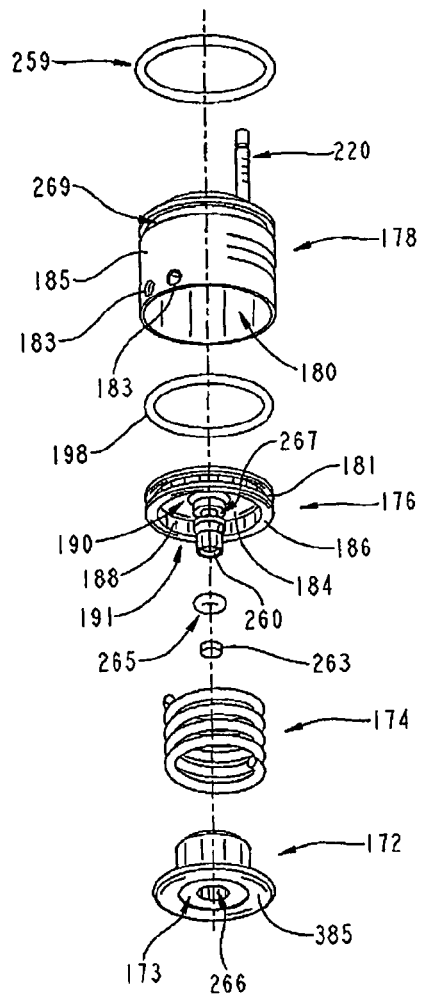
FIG. 7 is an isometric unassembled view of a vent mechanism, a biasing member, a piston, and a housing of the pressure reduction section of FIG. 6A.
Figure 8:
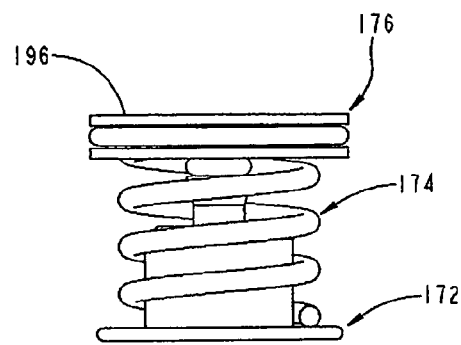
FIG. 8 is an isometric assembled view of the vent mechanism, biasing member, and piston of the pressure reduction section of FIG. 6A.

Referring to FIGS. 6A, 7 and 8, pressure reduction section 170 is shown. Pressure reduction section 170 includes a vent mechanism 172, a biasing member 174, a piston 176, and a housing 178. Pressure reduction section 170 is configured to receive a high pressure of fluid, such as greater than 500 psi, and to provide a lower pressure, such as about 5 psi, about 15 psi, about 20 psi, about 22 psi, about 27 psi, about 50 psi, about 60 psi, and the range of about 5 psi to about 60 psi, to one or more fluid inlet passages. This lower pressure is established as a fixed reduced pressure by the particular configuration of the components of pressure reduction section 170 selected for the desired lower pressure output. In one embodiment, housing 178 is coupled to an axle, such as axle 220', to support a flow selector/flow restrictor, such as flow selector 400, the axle either being solid or containing a fluid conduit which is in fluid communication with the interior of the housing.

As shown in FIG. 8, when assembled biasing member 174 is positioned between vent mechanism 172 and piston 176. Vent mechanism 172, biasing member 174, and piston 176 are each generally received within a cavity 180 (see FIGS. 6C and 7) of housing 178. When assembled, vent mechanism 172 is positioned adjacent fluid outlet 384 of fluid inlet retainer 360. A seal 382 (see FIG. 6C) is positioned between a first surface 184 (see FIG. 6C) of vent mechanism 172 and an axial surface 386 (see FIG. 6C) of body portion 302. Seal 382 is retained in a groove in body portion 302. In a preferred example, the groove is a half dove-tailed groove (see FIG. 6C). Referring to FIG. 7, piston 176 includes a seat surface 184 for receiving biasing member 174. Seat surface 184 is offset from axial surface 186 and is bounded by radial surface 188 thereby forming a recess 190. Recess 190 assists in the retention of biasing member 174 and reduces the overall length of the combination of vent mechanism 172, biasing member 174, and piston 176 (resulting in a reduction of the length of pressure reduction section 170 and hence of flow regulator 300). In one embodiment, the depth of recess 190 from axial surface 186 is about 74% of the distance from axial surface 186 to back surface 196 (see FIG. 8) of piston 176. In one example, the depth of recess 190 is about 0.125 inches and the separation between axial surface 186 and back surface 196 is about 0.169 inches. In one embodiment, piston 176 is made of brass.

In one embodiment, biasing member 174 is a compression spring. In one example, the spring is made of stainless steel with a load height of about 0.425 inches and a solid height of about 0.38 inches. The spring has a load of about 31.3 pounds.

Referring to FIG. 6C, piston 176 includes a stem 191 which includes a central fluid conduit 192 and a transverse fluid conduit 194. As explained in more detail below, fluid enters piston 176 through transverse fluid conduit 194, flows through fluid conduit 192, and exits piston 176 proximate to back surface 196 of piston 176. Stem 191 is received in a central passageway 266 (see FIG. 7) in vent mechanism 172. The height of vent mechanism 172 is chosen such that passageway 266 serves as a guide for piston 176 and to permit the proper travel of piston 176 in directions 268 and 270 shown in FIG. 6C. To this end recess 190 receives an end 272 of vent mechanism 172 as piston 176 travels in direction 270. Therefore, the inclusion of recess 190 in piston 176 permits the length of vent mechanism 172 to be longer and provide a more stable guide for piston 176, while maintaining the overall reduced length of regulator 300 as discussed above. In one embodiment, end 272 moves completely into recess 190 to contact bottom surface 184 of recess 190.

Piston 176 includes a radial groove 181 which receives a seal 198. Seal 198 provides a seal between piston 176 and housing 178 such that fluid is prevented from reaching back surface 196 of piston 176 except through fluid conduit 192. A recess 260 is formed in the end of stem 191 to receive a seal 263 (see FIG. 7). Seal 263 is positioned such that it can contact a seat surface 197 (see FIG. 6C) of fluid inlet retainer 130. In one example, seal 262 is a made of a glass filled Teflon, such as 15% glass filled Teflon. Piston 176 further includes a recess 267 to receive a seal 265. Seal 265 seals between piston 176 and base 172.

Pressure reduction section 170 is held in place relative to body portion 102 by a retainer 271. Retainer 271 is shown as a clip that is received in a groove of cavity 303 of body 302. In an alternative embodiment, pressure reduction section 170 is threadably received in cavity 303, is press fit into cavity 303, or secured by other suitable methods.

The operation of pressure reduction section 170 is described with reference to FIG. 6C. In the absence of any fluid flow biasing member 174 of pressure reduction section 170 biases piston 176 in direction 268 relative to vent mechanism or base 172 such that back surface 196 of piston 176 is positioned adjacent a seat surface 177 in housing 178 and such that vent mechanism 172 is in contact with seal 382. Flow regulator 300 is coupled to a source of pressurized fluid 322 such that high pressure fluid enters fluid inlet retainer 360 from source of pressurized fluid 322. The fluid then passes through filters 362, and exits fluid inlet retainer 360 through fluid outlet 384. This fluid passes through transverse conduit 194 of piston 176 and down central conduit 192 of piston 176. The fluid, assuming it is at a high enough pressure, builds up on the back side of piston 176 (adjacent back surface 196) causing piston 176 to move generally in direction 270. If flow selector 200 is set such that fluid is not permitted to pass through flow selector 200 (none of fluid passages 216 are aligned with fluid outlet 332 in housing 178), then piston 176 continues to move in direction 210 against the bias of biasing member 174 due to the pressure buildup on the backside of piston 176. As piston 176 moves in direction 270, seal 262 of piston 176 moves closer to seat surface 197 of fluid inlet retainer 130. Assuming pressure continues to build (flow selector 200 is not moved to permit fluid to exit through fluid outlet 332) seal 262 contacts seat surface 197 and fluid flow is prevented from exiting fluid inlet retainer 360.

As flow selector 200 is moved to a flow setting, fluid is permitted to flow through fluid conduit 332 in housing 178, through the corresponding fluid conduit 214 of flow selector 200, and to application device 310. Flow selector 200 is moved to a flow setting by a user imparting a rotation to flow selector 200. As stated above, a detent cooperates with indexes 250 to provide an indication to the user of when a fluid channel 216 is aligned with fluid outlet 332.

As fluid flows through flow selector 200, the pressure on the backside of piston 176 is reduced and piston 176 moves in direction 268 due to biasing member 174 such that seal 262 of piston 176 is spaced apart from seat surface 197. This movement once again permits fluid to exit fluid retainer 360 and to flow through piston 176. As time goes on and as long as the flow selector 200 is moved to a flow setting, a cyclic pattern is established wherein the pressure on the backside of piston 176 builds resulting in piston moving in direction 270 and thereby reducing the amount of fluid which flows to the backside of piston 176 followed by the pressure on the backside of piston 176 decreasing resulting in piston 176 moving in direction 268 and thereby increasing the amount of fluid which flows to the backside of piston 176.

Vent mechanism 172 also provides a safety feature to prevent a buildup of pressure in the interior of housing 178. Vent mechanism 172 includes a recess 173 (see FIG. 7) which is in fluid communication with fluid outlet 384. As pressure builds up in recess 173 (potentially due to an obstruction of the fluid passage 192 in piston 176), vent mechanism 172 can move in direction 268 against the bias of biasing member 174. Such movement brings recess 173 into fluid communication with region 180 in housing 178. As shown in FIG. 7, housing 178 includes a vent opening 183 in wall 185. Vent opening 183 is aligned with corresponding vent openings (not shown) in body 302 and cooperate with the vent openings in body 302 to bring region 180 in fluid communication with the air surrounding flow regulator 300. As such, an excessive pressure buildup may be vented to atmosphere. In one embodiment housing 178 and body 302 each include two vent openings.

Housing 185 further includes a recess 269 sized to receive a seal 259. Seal 259 seals between housing 185 and the interior cavity of body 302.

Referring to FIG. 6A, a second fluid passage 335 receiving fluid from pressure reduction section 170 may be included in flow regulator 300 to provide a second flow of fluid. Example uses for the second flow of fluid include providing a continuous flow line to the patient for a fluid conserver application device or a fluid supply for providing pressure to one side of a diaphragm of a pneumatic fluid conserver application device. As shown in FIG. 6A, passage 335 is located below flow selector 200. In another embodiment, in FIG. 6B, instead of second fluid passage 335 passing below flow selector 200, flow selector 200 uses axle 220' such that the second flow of fluid passes through the channel 221 of axle 220' and hence through flow selector 200 without passing through one of passages 216.

Figure 10:
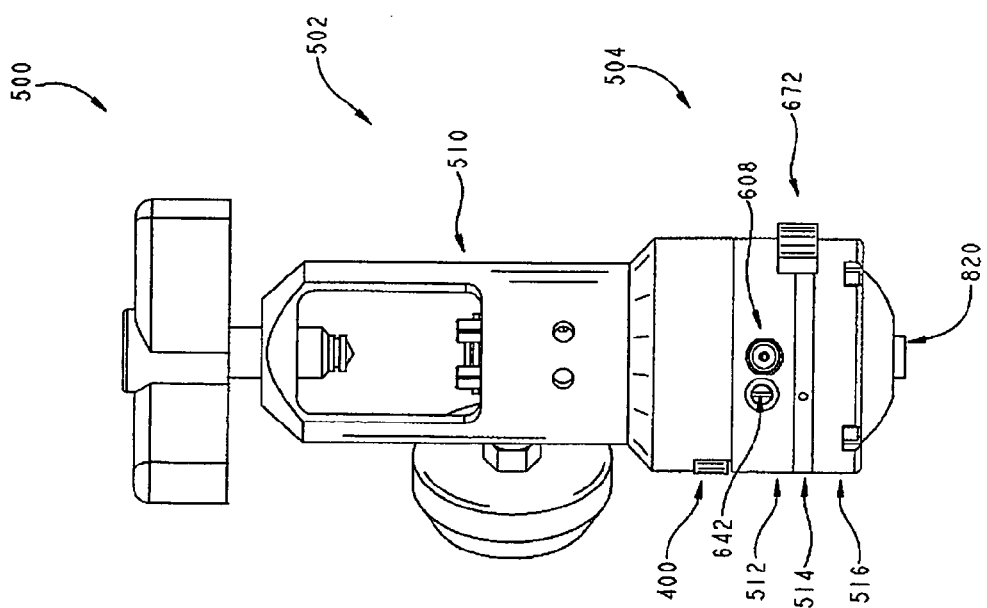
FIG. 10 is an isometric view of an exemplary conserving device including an exemplary flow regulator or regulating portion coupled with an exemplary fluid conserver application device or conserving portion, the flow regulator including a body portion and the fluid conserver application device including a first body portion, a second body portion, and a third body portion.

Referring to FIG. 10, an exemplary fluid conserver device 500 is shown. Conserver 500 includes a flow regulator portion 502 and a conserver portion 504. Flow regulator 502 is generally similar to flow regulator portion 300. Conserver portion 504 is configured for use with a single lumen cannula 503 (see FIG. 13). However, as explained herein, conserver portion 504 may also be configured for use with a dual lumen cannula (not shown).

Conserver 500 is configured to provide at least one metered or calibrated flow of fluid to the single lumen cannula in a continuous mode of operation and/or an intermittent mode of operation. In the continuous mode of operation, conserver 500 provides a continuous flow of fluid to a patient through the single lumen cannula. In the intermittent mode of operation, conserver 500 provides pulses of fluid to a patient through the single lumen cannula. As explained herein conserver 500 can also be configured for use with a dual lumen cannula and be configured to provide at least one metered or calibrated flow of fluid to the dual lumen cannula in a continuous mode of operation and/or an intermittent mode of operation. Both configurations of conserver 500 (single lumen and dual lumen) preferably are capable of providing one or more metered or calibrated flows to the respective cannula in a continuous mode of operation and/or intermittent mode of operation.

In one embodiment, the timing of the pulses and/or the duration of the pulses are triggered by the breathing cycle of the patient. In another embodiment, the timing of the pulses and/or the duration of the pulses are controlled by a pneumatic controller which uses the pneumatic characteristics of conserver 500 to move a valve or piston. In still a further embodiment, the timing of the pulses and/or the duration of the pulses are controlled by an electronic controller which activates an electrically or pneumatically activated valve or piston. The electronic controller is either integrated with the application device or separate from the application device. In still another embodiment the timing of the pulses and the duration of the pulses are controlled by a combination of one or more of the patient's breathing cycle, a pneumatic controller, and an electrical controller.

Flow regulator 502 is generally similar to flow regulator 300 described herein. It should be understood that the discussion above related to flow regulator 300 is generally applicable to flow regulator 502.

Figure 16:
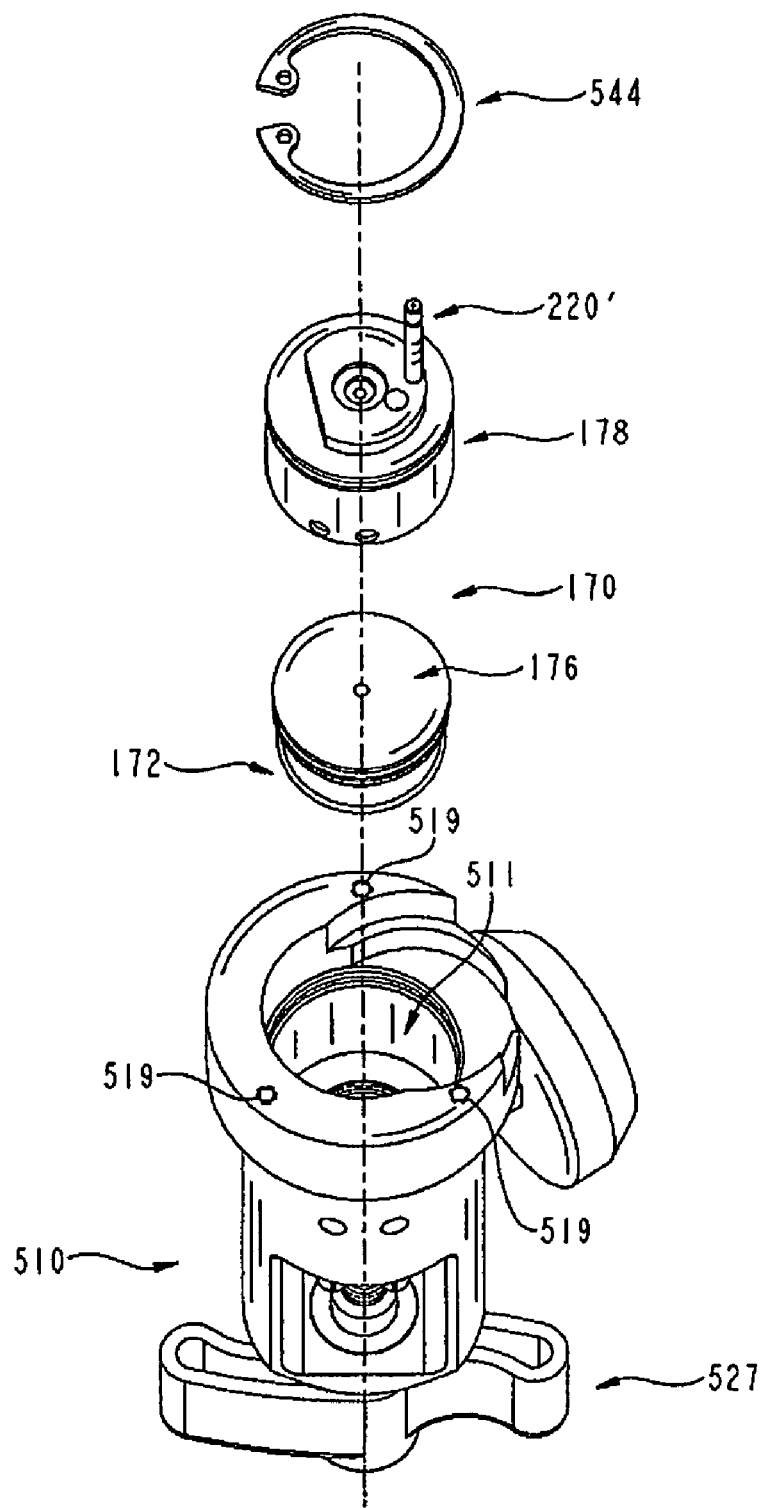
FIG. 16 is an isometric view of the body portion of the flow regulator of FIG. 10, showing an internal cavity and showing an exemplary pressure reduction assembly which is to be placed in the internal cavity of the first body portion of the flow regulator of FIG. 10, the pressure reduction assembly being held in the internal cavity with a retainer.
Figure 17C:
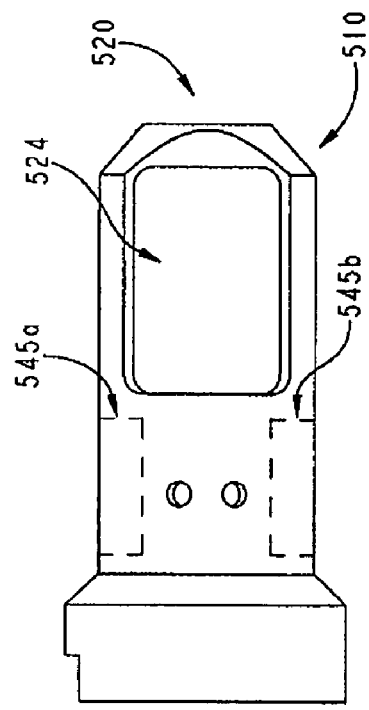
FIG. 17C is a third exemplary side view of the body portion of the flow regulator of FIG. 10.
Figure 17D:
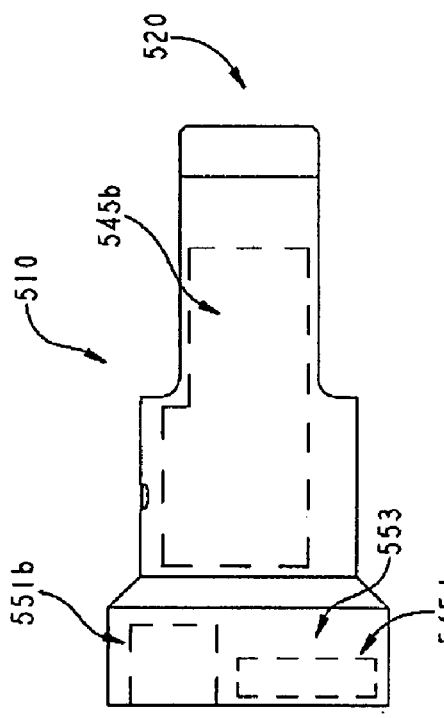
FIG. 17D is a fourth exemplary side view of the body portion of the flow regulator of FIG. 10.
Figure 17A:
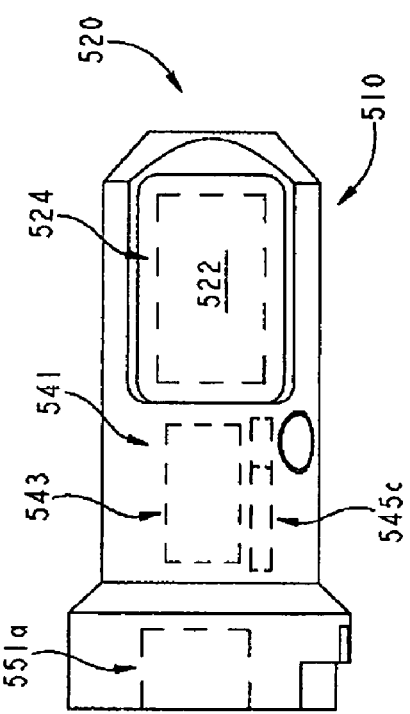
FIG. 17A is a first exemplary side view of the body portion of the flow regulator of FIG. 10.
Figure 17B:
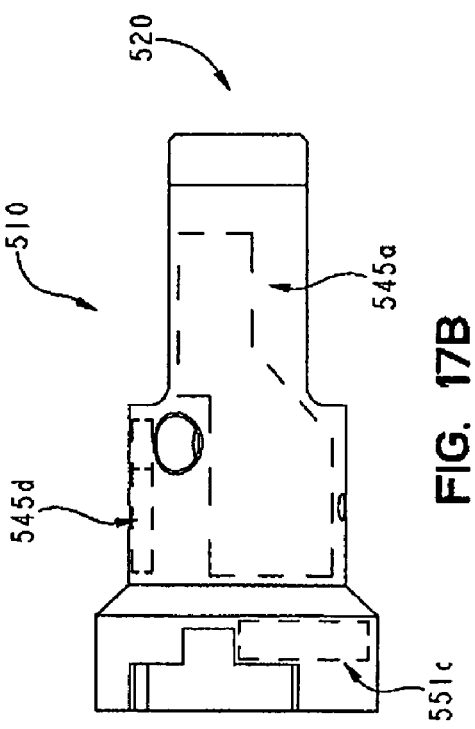
FIG. 17B is a second exemplary side view of the body portion of the flow regulator of FIG. 10.

Referring to FIG. 16, flow regulator 502 includes a main body 510 having an internal cavity 511 sized to receive pressure reduction section 170 and a flow selector 400 (see FIG. 19). Pressure reduction section 170 receives fluid from a fluid inlet retainer 531 (see FIG. 13) and is configured to provide a lower pressure, such as about 5 psi, about 15 psi, about 20 psi, about 22 psi, about 27 psi, about 50 psi, about 60 psi, and the range of about 5 psi to about 60 psi, to a fluid inlet passage 332. This lower pressure is established as a fixed reduced pressure by the particular configuration of the components of pressure reduction section 170 selected for the desired lower pressure output. Fluid inlet retainer 531 is generally similar to fluid inlet retainer 360.

Returning to FIG. 10, conserver portion 504 includes a first body portion 512, a second body portion 514 and a third body portion 516. Body portion 510 of flow regulator portion 502 and body portions 512, 514, 516 of conserver portion 504 are assembled, such as by stacking, to provide conserver 500. As explained in more detail below, couplers 518 (see FIG. 12) are received in corresponding openings in body portions 512, 514, 516 of conserver 504 and are threaded into openings 519 (see FIG. 16) of body portion 510 of flow regulator 502. In the illustrated embodiment, body portions 510, 512, 514, 516 are configured such that there is only a single orientation that corresponds to a proper assembly of body portions 510, 512, 514, 516.

In an illustrated embodiment, the single orientation is defined by the spacing of the respective openings in 510, 512, 514, 516 which receive couplers 518. Referring to FIG. 16, the respective openings whose location corresponds to the locations of couplers 518 are spaced around the body portions 510, 512, 514, 516 such that only a single orientation of body portions 510, 512, 514, 516 will result in allowing couplers 518 to pass through the respective openings and to couple the respective body portions 510, 512, 514, 516 together. In an alternative embodiment, the various body portions include key features and respective key recesses to orient the respective body portions relative to each other. In another alternative embodiment the various body portions include mounting components which couple the respective body portions together. The assembly of conserver 500 is explained in more detail with respect to FIGS. 16-29.

Figure 13:
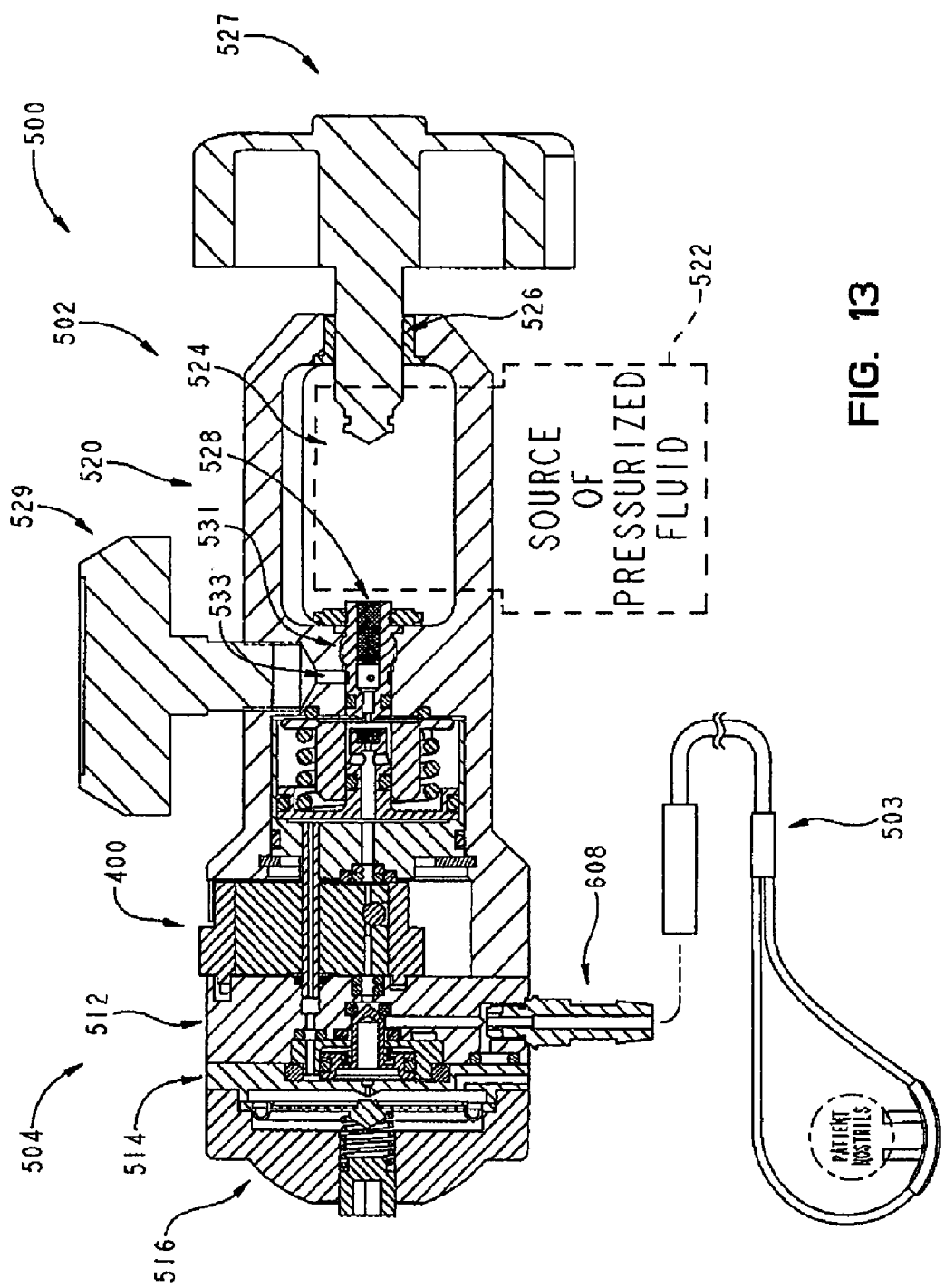
FIG. 13 is a sectional view of the conserving device of FIG. 10 illustrating the various components of the conserving device of FIG. 10.

Referring to FIG. 13, body 510 includes a yoke 520 configured to couple a source of pressurized fluid 522 to conserver 500. Yoke 520 includes an opening 524 sized to receive a post valve and a threaded aperture 526 sized to threadably receive a retainer 527. As is known in the art, retainer 527 urges a fluid outlet of the post valve into engagement with a fluid inlet 528 of flow regulator 502 such that fluid is communicated to flow regulator 502 from the source of pressurized fluid 522. Fluid from fluid passage 528 is provided to a fluid pressure gauge 529 through fluid passage 533 to provide a reading of the pressure in the source of pressurized fluid 522.

Referring to FIGS. 17A-D, body 510 includes several regions for the inclusion and/or placement of instructions or other indicia 541. In the illustrated embodiment, company identification information is located in region 543, instructional or informational text is located in regions 545*a-d*. Further, indicia 541 may include alignment indicia in regions 551*a-c* to assist in communicating to a user the selected flow rate of flow selector 400 and/or the mode of operation of conserver 500.

Referring to FIGS. 7 and 16, pressure reduction section 170 includes a vent mechanism 172, a biasing member 174, a piston 176, and a housing 178. Pressure reduction section 170 is configured to provide a lower pressure, such as about 5 psi, about 15 psi, about 20 psi, about 22 psi, about 27 psi, about 50 psi, about 60 psi, and the range of about 5 psi to about 60 psi, to one or more fluid inlet passages. This lower pressure is established as a fixed reduced pressure by the particular configuration of the components of pressure reduction section 170 selected for the desired lower pressure output.

As illustrated in FIG. 8, biasing member 174 is positioned between vent mechanism 172 and piston 176. Vent mechanism 172, biasing member 174, and piston 176 are each generally received within a cavity 180 (see FIG. 7) of housing 178. When assembled, vent mechanism 172 is positioned adjacent seal 542 (see FIG. 14) and pressure reduction section 170 is held in place by a retainer 544 (see FIG. 16). Retainer 544 is shown as a clip that is received in a groove of cavity 511 of body 510. In an alternative embodiment, flow reduction member 530 is threadably received in cavity 511, is press fit into cavity 511, or secured by other suitable methods.

As explained in more detail below with reference to FIG. 14, pressure reduction section 170 includes a first fluid passage 546 through an opening in piston 176 a second fluid passage 548 formed in the space between piston 176 and an interior surface 550 of housing 178 and a third fluid passage 547 generally aligned with first fluid passage 546. Fluid from fluid passage 547 is communicated to one of the fluid passages 416 through flow selector 400 to provide a metered or calibrated fluid flow to a fluid outlet passage as discussed in more detail below.

Referring to FIG. 16, housing 178 is coupled to an axle, such as axle 220'. Axle 220' is press fit into an opening of housing 178. In alternative embodiments, axle 220' is threadably received by an opening in housing 178, secured to housing 178 with an adhesive or by a mechanical joint, such as a weld, is integrally formed with housing 178, or is rotatably coupled to housing 178. As explained above, axle 220' has a fluid passage 221 formed therein. Fluid passage 221 in one embodiment is a calibrated fluid passage such that a known fluid flow rate is associated with fluid passage 221. In alternative embodiments, a solid axle is used.

Figure 14:
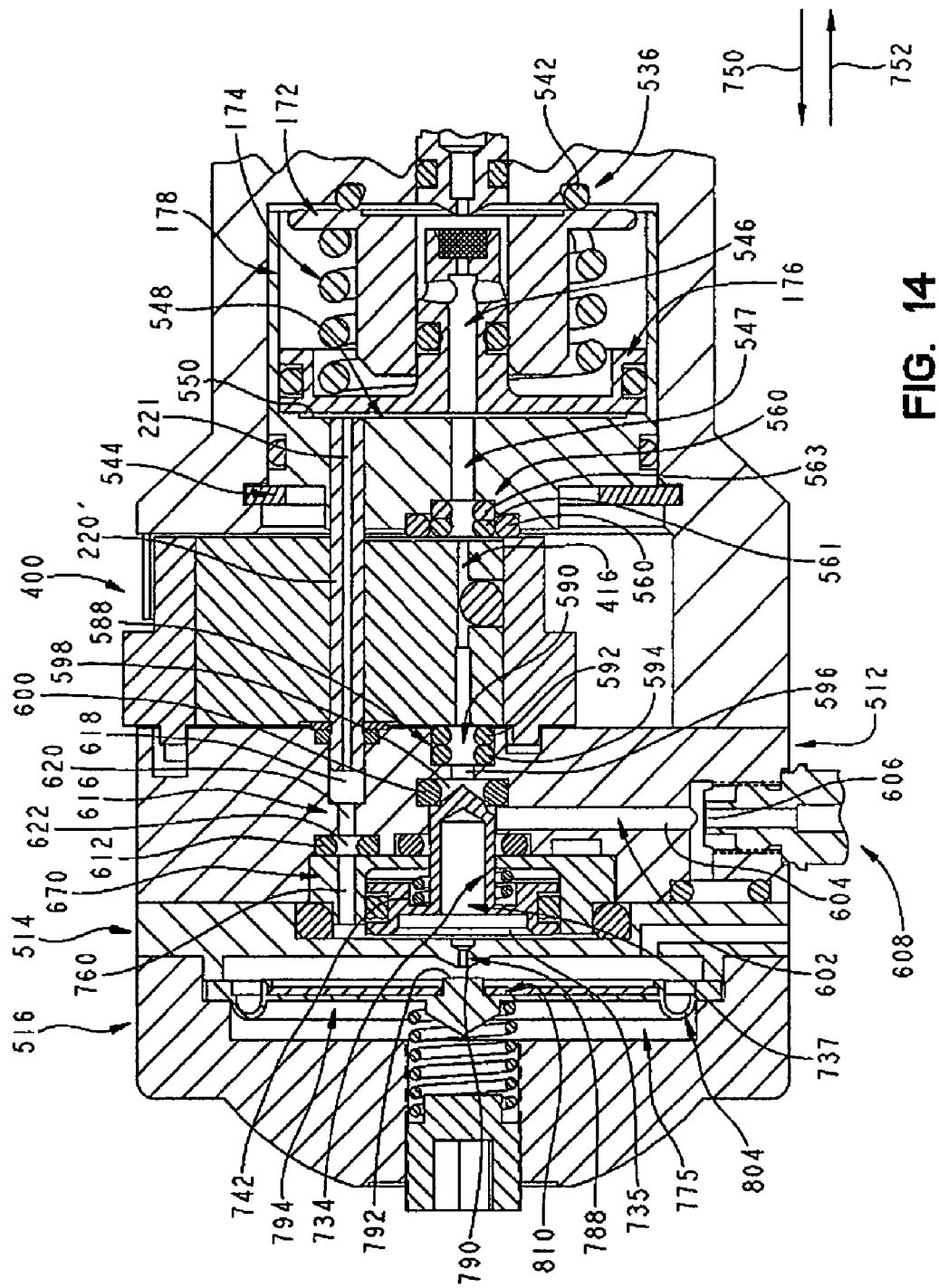
FIG. 14 is a detail view of the sectional view of FIG. 13.

Referring to FIG. 14, fluid passage 221 is in fluid communication with fluid passage 548 of pressure reduction section 170. As explained in more detail below, in one embodiment, fluid passing through fluid passage 548 and fluid passage 221 is used to control the operation of a demand piston 734.

Figure 20:
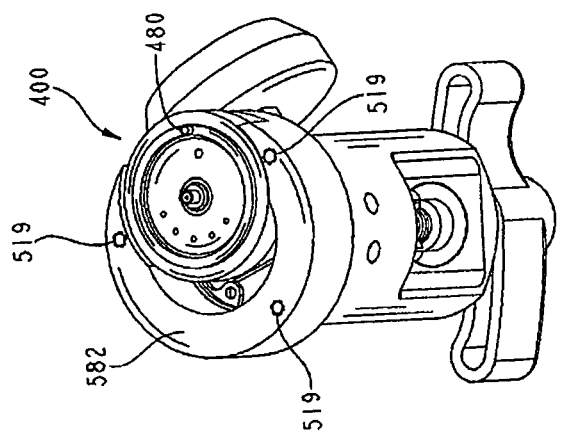
FIG. 20 is an isometric view of the body portion of the flow regulator of FIG. 10 having the pressure reduction assembly of FIG. 16 and the flow selector of FIG. 5A assembled.

Referring to FIGS. 14, 19, and 20, flow selector 400 is rotatably coupled to axle 220. A central channel 452 (see FIG. 19) of flow selector 400 receives axle 220'. In an alternative embodiment, axle 220' is fixably coupled to flow selector 400 and is rotatably coupled to pressure reduction section 170.

As discussed above, flow selector 400 includes a plurality of recesses 450 sized to receive a detent 554 (see FIG. 19). Recesses 450 cooperate with detent 554 to align respective flow passages 416 in flow selector 400 with flow passage 547 in pressure reduction section 170 and to provide a positive indication to the user of such alignment. Referring to FIG. 19, detent 554 is a spherical ball which is at least partially received in a recess 556 of housing 178 of pressure reduction section 170. Detent 554 is sized to cooperate with recesses 450 in flow selection 400.

A biasing member 558, illustratively a spring, is also received in recess 556 of housing 178 and biases detent 554 into recess 450 of flow selector 400. Additional exemplary detents include a bump on the surface of housing 178 or a plastic insert having a bump. In alternative embodiments, detent 554 is received in a recess of flow selector 400 and housing 178 includes a plurality of recesses each one corresponding to the alignment of a fluid passage 416 in flow selector 400 with fluid passage 547 in pressure reduction section 170.

Once detent 554 and biasing member 558 are positioned in recess 556, flow selector 400 is positioned over axle 220' such that one of recesses 450 of flow selector 400 is cooperating with detent 554 and such that a back surface 441 (see FIG. 5B) of flow selector 400 is in contact with seal 560 (see FIG. 19) which prevents or minimizes the escape of fluid as the fluid passes from fluid passage 547 in pressure reduction section 170 into fluid passage 416 of flow selector 400. In the illustrated embodiment of FIG. 14, seal 560 and two additional seals 561, 563 assist to prevent or minimize the escape of fluid as fluid passes from fluid passage 547 in pressure reduction section 170 into fluid passage 416. Seals 560, 561, and 563 cooperate to act as a silencer or muffler as flow sector 400 is rotated during the selection of the appropriate fluid passages 416.

Referring to FIG. 19, flow selector 400 is axially held in place by a retainer 564 such that back surface 441 (see FIG. 5B) of flow selector 400 remains in contact with seal 560 and such that one of recesses 450 is cooperating with detent 554. Retainer 564 is received in a circumferential channel in axle 220'. A seal 562 is positioned over retainer 564. In an alternative embodiment, flow selector 400 is held in place by conserver 504, a nut threadably received by axle 220' or other suitable securing means that axially secure flow selector 400 while still permitting flow selector 400 to be rotatable relative to axle 220'.

Flow selector 400 is shown assembled with body 510 and pressure reduction section 170 in FIG. 20. It should be noted that radial surface 422 is accessible from the exterior of body portion 510 and that a user can input a rotation to flow selector 400.

Figure 21A:
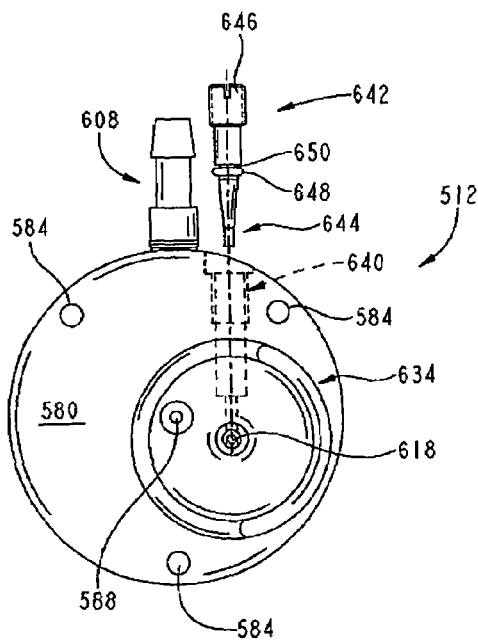
FIG. 21A is a bottom view of a first body portion of the fluid conserver application device generally showing a nipple adapted for connection to a single lumen cannula and a needle valve exploded therefrom, the needle valve being positionable with a recess of the first body portion.
Figure 21B:
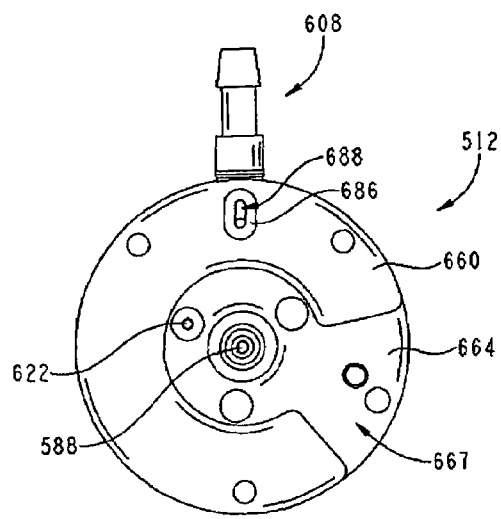
FIG. 21B is a top view of the first body portion of FIG. 21A.
Figure 22:
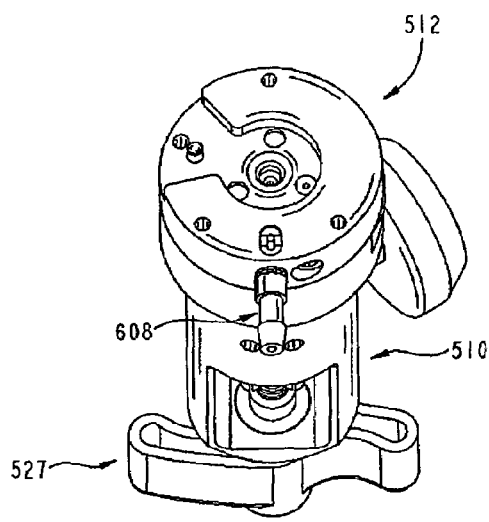
FIG. 22 is a generally isometric view of the first body portion of the fluid conserver application device assembled onto the assembly of FIG. 20.

Referring to FIGS. 21A and 21B first body portion 512 of conserver portion 504 is shown. Referring to FIG. 21A, a lower surface 580 of first body portion 512 is shown. Lower surface 580 mates with an upper surface 582 (see FIG. 20) of body portion 510. First body portion 512 includes a plurality of openings 584 each sized to receive respective couplers 518 which are then threadably received in openings 586 of body portion 510.

First body portion 512 includes a central fluid passage 588 configured to align with the respective one of fluid passages 416 in flow selector 400 which is currently aligned with fluid passage 547 in flow regulator portion 502. As best shown in FIG. 14, central fluid passage 588 includes a first portion 590 sized to receive seals 592, 594, a second portion 596, and a third portion 598 sized to receive seal 600. Seals 592, 594 seal the transition from fluid passage 416 in flow selector 400 to fluid passage 588 in first body portion 512. As explained in more detail below, seal 600 seals the transition from fluid passage 588 and a fluid passage 602 in first body portion 512 and provides a seat for demand piston 734.

Referring to FIG. 14, fluid passage 602 includes a first portion 604 which intersects with third portion 598 of fluid passage 588 and a second portion 606 sized to be threadably coupled to a nipple 608. Nipple 608 is configured to couple to single lumen cannula 503 (see FIG. 13) as is well known in the art. A seal (not shown) is provided to seal the connection between fluid passage 602 and nipple 608.

It should be noted that FIGS. 13, 14, and 14A-D are provided to better illustrate the operation of conserver 500 and that FIGS. 13, 14, and 14A-D are not intended to be a single cross-section through conserver 500 but rather to illustrate various features of the various components of conserver 500.

First body portion 512 further includes fluid passage 616 having a first portion 618 sized to receive axle 220', a second portion 620, and a third portion 622. First portion 618 is sized to receive an end of axle 220' and is in fluid communication with channel 221 of axle 220'. Further, first portion 618 includes a recess sized to receive seal 562 which seals the connection between axle 220' and first body portion 512. Third portion 622 is sized to receive a seal 612 which is sized to seal the connection between fluid passage 616 and first mode selector member 670.

Figure 12A:
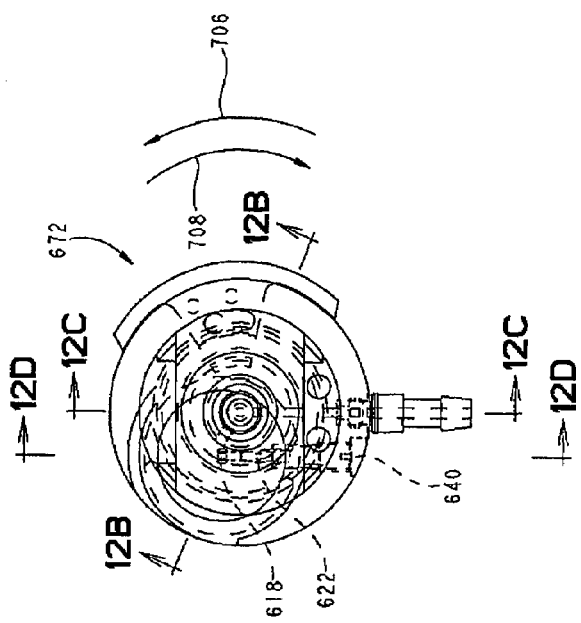
FIG. 12A is a top view of the assembly of FIG. 12 with various features shown.
Figure 12B:
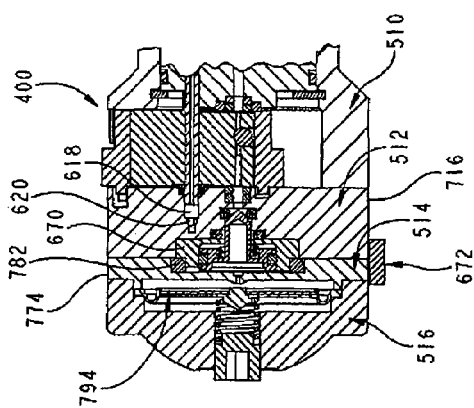
FIG. 12B is a cross section of FIG. 12A taken along lines 12B-12B in FIG. 12A.
Figure 12:
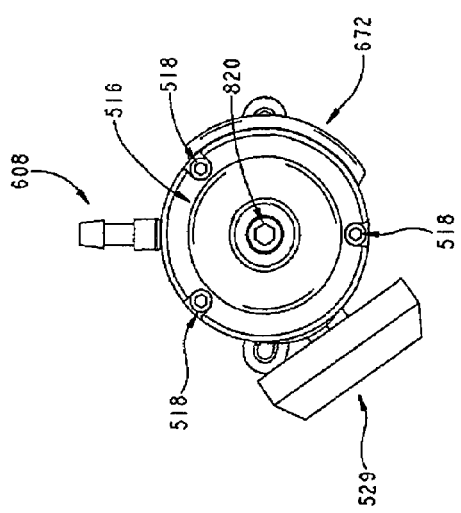
FIG. 12 is a top view of the conserving device of FIG. 10.
Figure 12D:
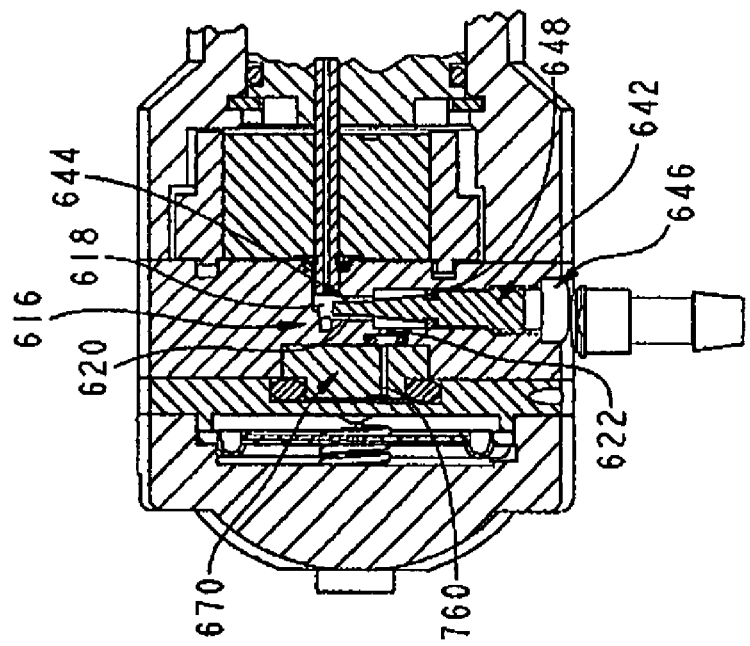
FIG. 12D is a cross section of FIG. 12A taken along lines 12D-12D in FIG. 12A.

As explained herein, the flow characteristics of fluid passage 616 are adjustable with a needle valve 642 (see FIG. 21A and 12D). As illustrated in FIG. 14 the three portions 618, 620, 622 of fluid passage 616 are arranged in a linear relationship. In a preferred embodiment shown in FIGS. 12A and 12D, portions 618 and 622 are longitudinal passages formed part way through first body portion 512 and are not aligned. Portions 618 and 622 are connected by transverse portion 620 which is explained herein interacts with needle valve 642.

Referring to FIGS. 12 and 12D, first body portion 512 further includes a opening 640 sized to receive a needle valve 642. As shown in FIG. 12D, opening 640 intersects with fluid passage 616 such that a tip 644 of needle valve 642 is positionable within a portion of passage 616. Needle valve 642 is threadably received by opening 640 and includes a tool engagement portion 646 for engagement by a tool. In the illustrated embodiment, tool engagement portion 646 is configured to be engaged by a flat screwdriver which can be used to advance needle valve 642 into and out of opening 640. A seal 648 is positioned on a seat 650 (see FIG. 21A) of needle valve 642 and cooperates with opening 640 to prevent the passage of fluid from the tip side 644 of needle valve 642 to the tool engagement side 646 of needle valve 642.

By adjusting the position of tip 644 within fluid passage 616, the cross-sectional area of second portion 620 of fluid passage 616 may be adjusted. As such, needle valve 642 is used to adjust the rate at which fluid passes from first portion 618 of fluid passage 616 to third portion 622 of fluid passage 616. The cross-sectional area effects the sensitivity of conserver 504 as explained in more detail below.

Returning to FIG. 21A, first body portion 512 further includes an alignment feature 634 configured to mate with an alignment feature of flow selector 400 (such as pin 480 shown in FIG. 20). In the illustrated embodiment, alignment feature 634 is a groove sized to receive pin 480. Pin 480 is received in a recess (not shown) of flow selector 400. Alignment feature 634 has two depths (see FIG. 12B), a first depth to accommodate a ridge 481 of flow selector 400 and a second depth to accommodate pin 480. The portion of alignment feature 634 which is configured to accommodate ridge 481 is generally circular while the portion of alignment feature 634 configured to accommodate pin 480 is generally a sector of a circle. The sector of alignment feature 634 and pin 480 cooperate to limit the rotation of flow selector 400.

Figure 23A:
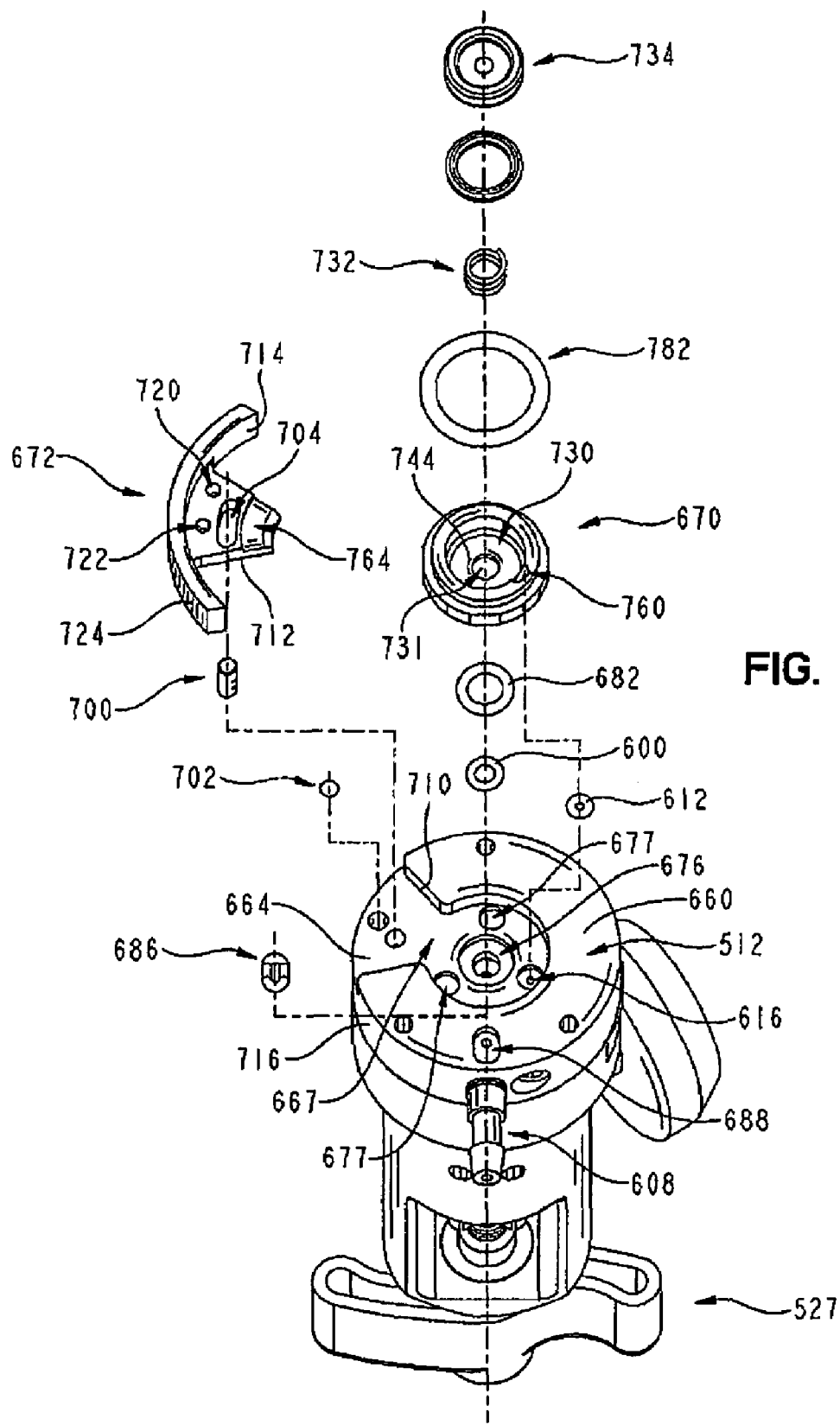
FIG. 23A is an exploded assembly view of the second body portion of FIG. 22, showing a first mode selector member, a second mode selector member, a demand piston and a biasing member, the demand piston generally used in the controlling of the delivery of pulses of fluid from the fluid conserver application device to a cannula and hence to the patient.

Referring to FIG. 23A, first body portion 512 is shown assembled to flow regulator portion 502. As shown in FIG. 21B, first portion 512 includes a first rear axial surface 660 which as explained below is positioned adjacent a surface 778 (see FIG. 25A) of second body portion 514 and a second rear axial surface 664 recessed from first axial surface 660. As explained in more detail below, recess 667 (see FIGS. 21B and 23A) formed by second axial surface 664 and is sized to receive first mode selector member 670 and second mode selector member 672. As explained in more detail herein, first mode selector 670 and second mode selector 672 cooperate to configure conserver portion 504 for use in one of an intermittent mode of operation or a continuous mode of operation.

As shown in FIG. 14, seal 600 is positioned adjacent to fluid passage 588 and seal 612 positioned adjacent to fluid passage 616. Returning to FIG. 23A, a recess 676 which is coaxially aligned with fluid passage 588 is formed or otherwise created in second rear axial surface 664. Recess 676 is sized to receive a portion of demand piston 734 and to provide a seat for seal 600. A seal 682 is also received in recess 676. Seal 682 along with seal 612 seals the connection between first body portion 512 and first selector member 670.

In the illustrated embodiment, two addition recesses 677 are formed or others tested in second axial surface 664. Recesses 667 are sized to receive two additional seals similar to seal 612. These two additional seals and seal 612 provide three points of contact with a bottom surface 671 (see FIG. 32) of first selector member 670.

Figure 12C:
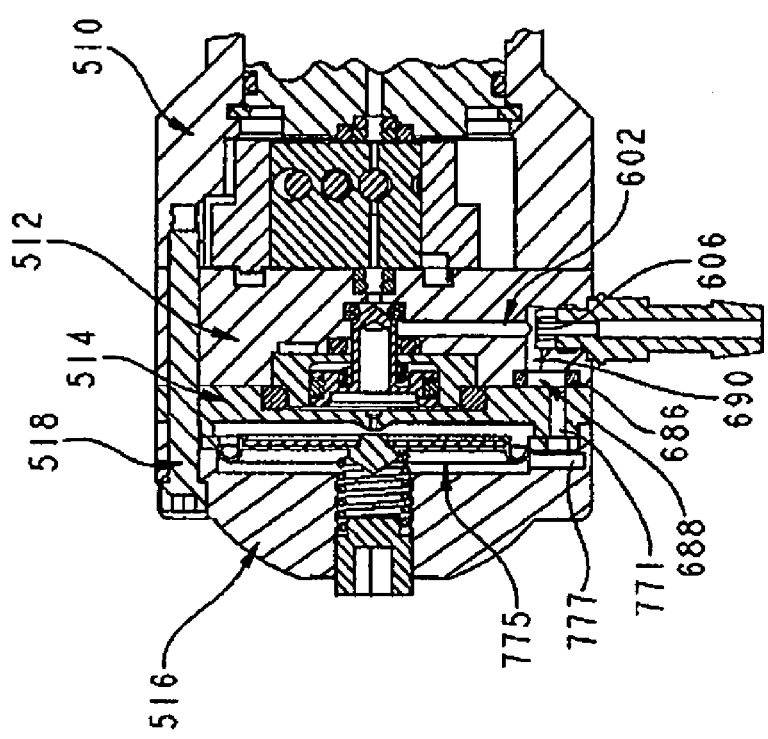
FIG. 12C is a cross section of FIG. 12A taken along lines 12C-12C in FIG. 12A.

A seal 686 is also shown positioned with a recess 688 of first rear axial surface 660 of first body portion 512. As best shown in FIG. 12C, a fluid passage 690 connects recess 688 with second portion 606 of fluid passage 602. Seal 686 seals the connection between second body portion 514 and first body portion 512 around fluid passage 690. As explained in more detail below, fluid passage 690 is utilized with third body portion 516 configured for use with a single lumen cannula to bring fluid passage 602 and a cavity 775 into fluid communication.

Referring back to FIG. 23A, an alignment member 700 is shown along with a detent 702. Alignment member 700 is received in an elongated arcuate slot 704 of second mode selector 672. The movement of second mode selector 672 in directions 706, 708 (see FIGS. 12A-24) is limited by one of contact between alignment member 700 and an edge of slot 704 or contact between a wall 710 of recess 667 and a side wall 712 of second mode selector 672. The pivoting of second mode selector 672 about alignment member 700 is minimized by the generally concentric arrangement of surface 714 of second mode selector 672 and outer surface 716 of first body portion 512 and/or outer surface 774 of second body portion 514 (see FIG. 12B) and the interaction between first mode selector 670 and second mode selector 672.

Second mode selector member 672 further includes two opening 720, 722 each of which are concentrically aligned with detent 702 relative to passage 588. Openings 720, 722 correspond to two preferred positions of second mode selector 672. As explained in more detail herein, opening 720 corresponds to the selection of a continuous mode of operation of conserver device 500 and opening 722 corresponds to the selection of an intermittent mode of operation of conserver device 500. Second mode selector 672 further includes a textured portion 724 configured to aid the transfer of force from a user's hand to second mode selector 672.

First mode selector 670 includes a recess 730 having a central opening 731. Recess 730 is sized to receive a biasing member 732 and demand piston 734. Biasing member 732 and demand piston 734 are assembled as shown in FIG. 23B and then received by recess 730 as shown in FIG. 24.

Figure 23B:
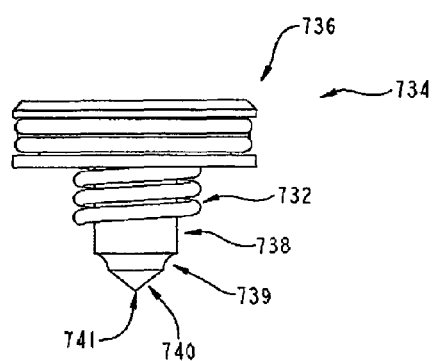
FIG. 23B is a side view of the demand piston and biasing member of FIG. 23A.
Figure 24:
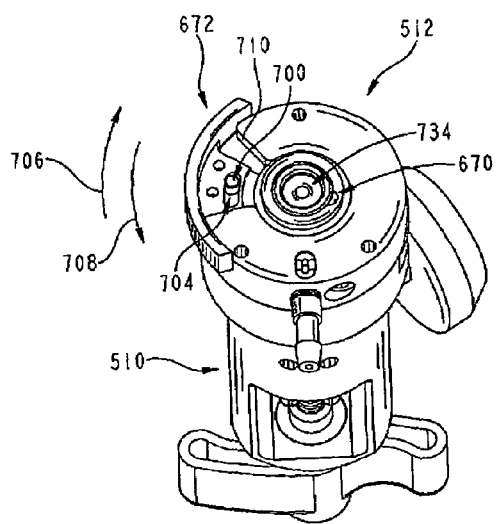
FIG. 24 is an assembled view illustrating the first mode selector member, the second mode selector member, the demand piston, and the biasing member assembled to the assembly of FIG. 22.

Referring to FIG. 23B, demand piston 734 includes a first portion 736 and a second portion 738. Second portion 738 includes a reduced end portion 740 having a seat surface 739 configured to mate with seal 600 as shown in FIG. 14B. in the illustrated embodiment, seat surface 739 is spaced apart from a tip or end 741 of second portion 738. First portion 736 includes a recess sized to receive biasing member 732 which is compressed between a surface 742 (see FIG. 14) of demand piston 734 and a surface 744 (see FIG. 23A) of first mode selector member 670.

Returning to FIG. 14, biasing member 732 generally biases demand piston 734 in direction 750 such that flow passage 588 is in fluid communication with fluid passage 602. However, biasing member 732 is compressible to permit the movement of demand piston 734 in direction 752 such that reduced portion 740 of demand piston 734 is sealed against seal 600. When reduced portion 740 is sealed against seal 600, fluid passage 588 is no longer in fluid communication with fluid passage 602. As such, by controlling the positioning of demand piston 734 relative to seal 600, the passage of fluid from fluid passage 588 to fluid passage 602 and hence to the patient through cannula 503 which is attached to nipple 608 can be controlled.

Referring to FIG. 12D, first mode selector member 670 includes a fluid passage 760. Fluid passage 760, as shown in FIGS. 12D and 14, is positioned to align with fluid passage 616 at least in one orientation of first mode selector member 670. As explained in more detail herein, fluid passage 760 aligns with fluid passage 616 when conserver 504 is configured to operate in an intermittent mode of operation and fluid passage 760 is not aligned with fluid passage 616 when conserver 504 is configured to operate in a continuous mode of operation.

Referring to FIG. 23A, first mode selector member 670 includes a recess 762 (see FIG. 32) which is configured to receive a tab 764 of second mode selector member 672. The reception of tab 674 in recess 762 effectively couples first mode selector member 670 to second mode selector member 672 such that a rotation of second mode selector 672 in one of directions 706, 708 will result in a corresponding rotation of first mode selector 670. Therefore, by moving second mode selector 672, a user is able to cause the rotation of first mode selector 670 and thus select either a continuous mode of operation for conserver 504 or an intermittent mode of operation for conserver 504 (based on the alignment or non-alignment of fluid passage 760 with fluid passage 616). It should be noted that the selection of the mode of operation is independent of the selection of a fluid flow rate with flow selector 400. However, the selection of the mode of operation can be constrained based on the selection of a fluid flow rate with flow selector 400 as explained herein.

Figure 25A:
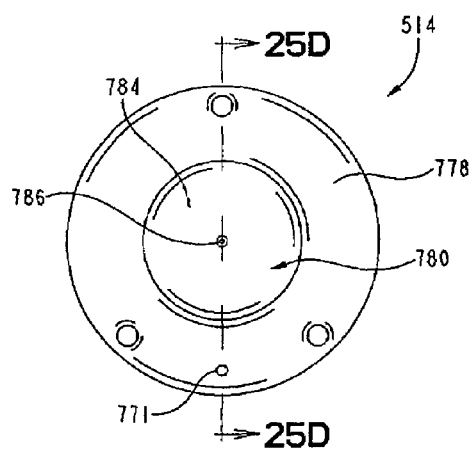
FIG. 25A is a front view of an exemplary second body portion of the fluid conserver application device.
Figure 25B:
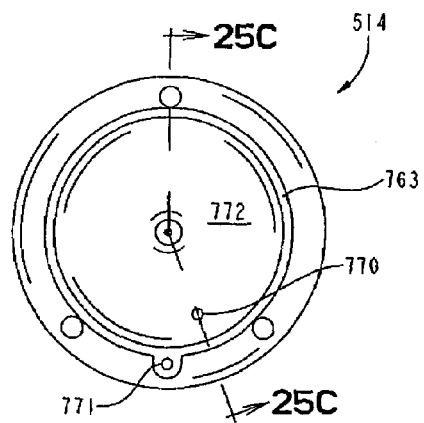
FIG. 25B is a back view of the second body portion of FIG. 25A.
Figure 25C:
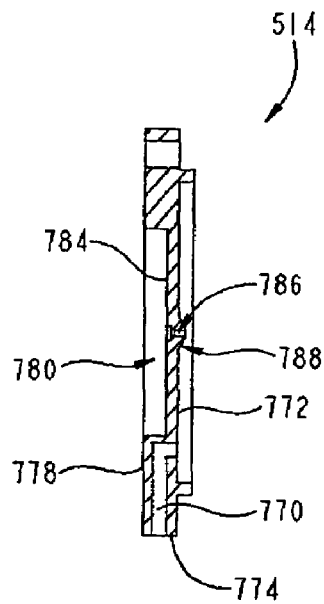
FIG. 25C is a sectional view of the second body portion generally taken along lines 25C-25C in FIG. 25B.

Referring to FIGS. 25A and D, second body portion 514 includes a vent fluid passage 770 which connects a front surface 772 of second body portion 514 and a radial surface 774 of second body portion 514. A rear surface 778 of second body portion 514 includes a recess 780 sized to receive first mode selector member 670 and a seal 782 (see FIG. 12B) which seals the connection between second body portion 514 and first mode selector member 670. Further, a surface 784 of recess 780 includes a fluid channel 786 which connects surface 784 to the front side of second body portion 514.

Figure 25D:
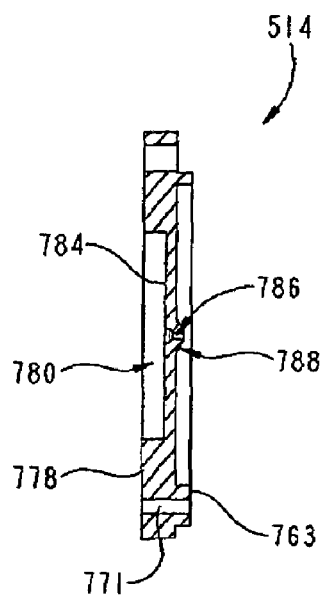
FIG. 25D is a sectional view of the second body portion of FIG. 25A generally taken along lines 25D-25D in FIG. 25B.
Figure 26:
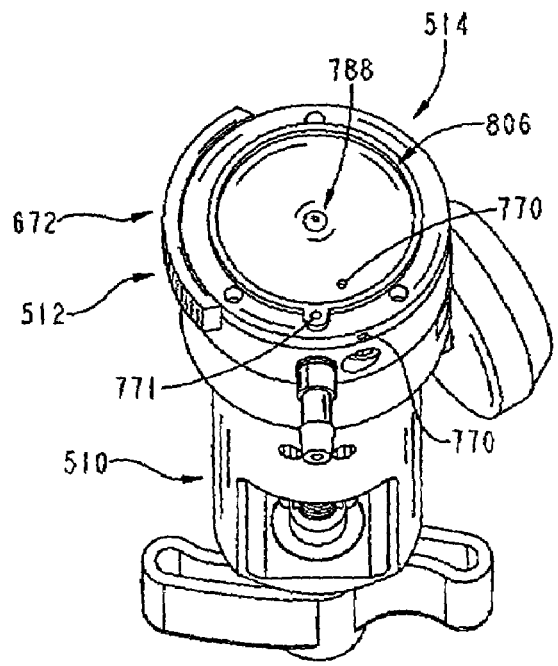
FIG. 26 is an isometric view showing the second body portion of the fluid conserver application device assembled with the assembly of FIG. 24.

Referring to FIG. 25D, fluid channel 786 intersects the front side of second body portion 514 in a raised portion 788 of second body portion 514. Raised portion 788 includes a seat surface 790 (see FIG. 14) which as explained in more detail below provides a seat for a pad 792 (see FIG. 14) of a diaphragm 794 (see FIG. 14).

Figure 28:
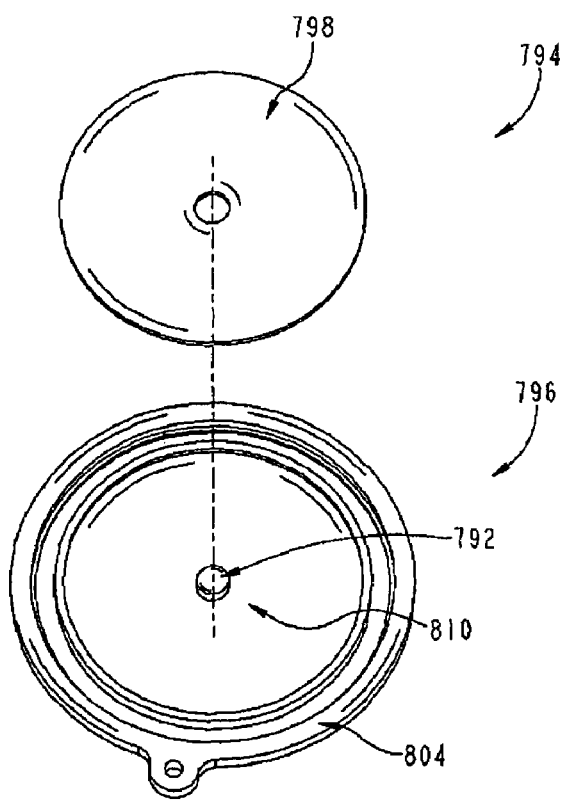
FIG. 28 is an exploded isometric view of a diaphragm assembly including a diaphragm and a support.

Referring to FIG. 28, diaphragm 794 illustratively includes a flexible portion 796 and a support 798. Flexible portion 796 permits the movement of diaphragm 794. Support 798 provides some rigidity to diaphragm 794 in order to provide better control over the movement of diaphragm 794. In one embodiment, support 798 is coupled to flexible portion 796 with adhesive. In another embodiment, the support includes a plurality of apertures which are sized to receive a corresponding plurality of buttons formed on the diaphragm. The buttons each include a lip or ridge that retains the button and thus the diaphragm relative to the support. In a further embodiment, the flexible portion is molded over the support.

An outer portion 804 of diaphragm 794 is fixably held by second body portion 514 and third body portion 516. Outer portion 804 is supported by seat 806 (see FIG. 26) of second body portion 514 and held in place due to both seat 806 of second body portion 514 and a seat 808 (see FIG. 27A) of third body portion 516. While outer portion 804 is held by second body portion 514 and third body portion 516, a central portion 810 of diaphragm 794 is able to move in directions 750, 752 (see FIG. 14) relative to outer portion 804 due to the flexible nature of diaphragm 794.

Figure 27:
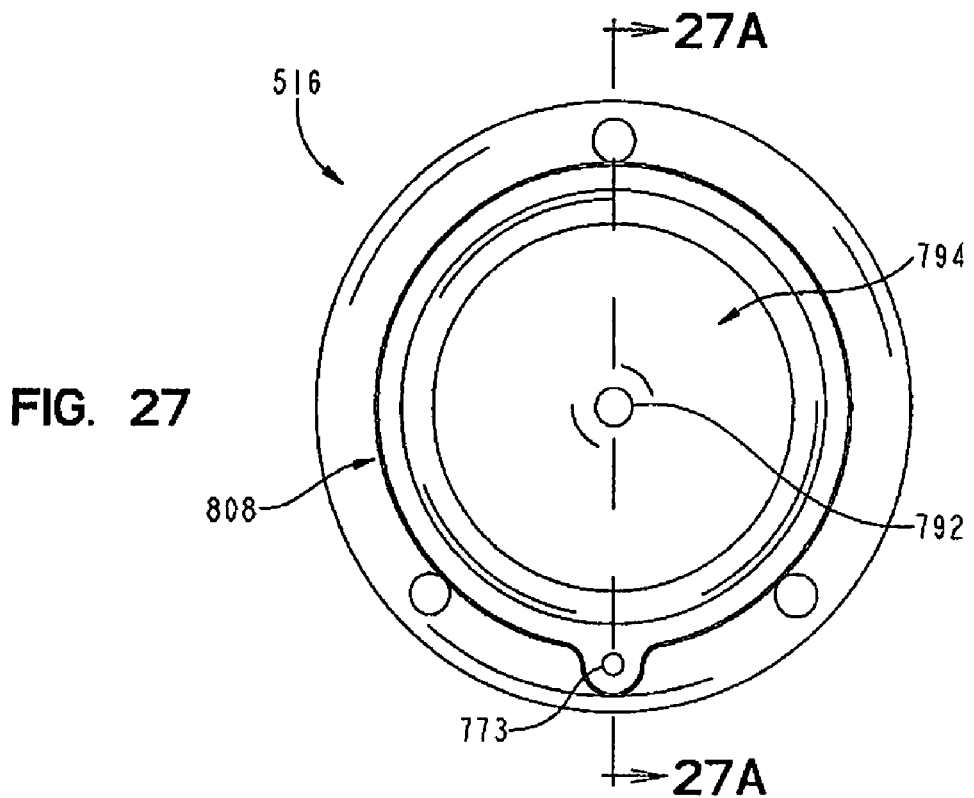
FIG. 27 is a bottom view of the bottom of the third body portion of the fluid conserver application device of FIG. 10 with the diaphragm of FIG. 28 assembled thereto.
Figure 27A:
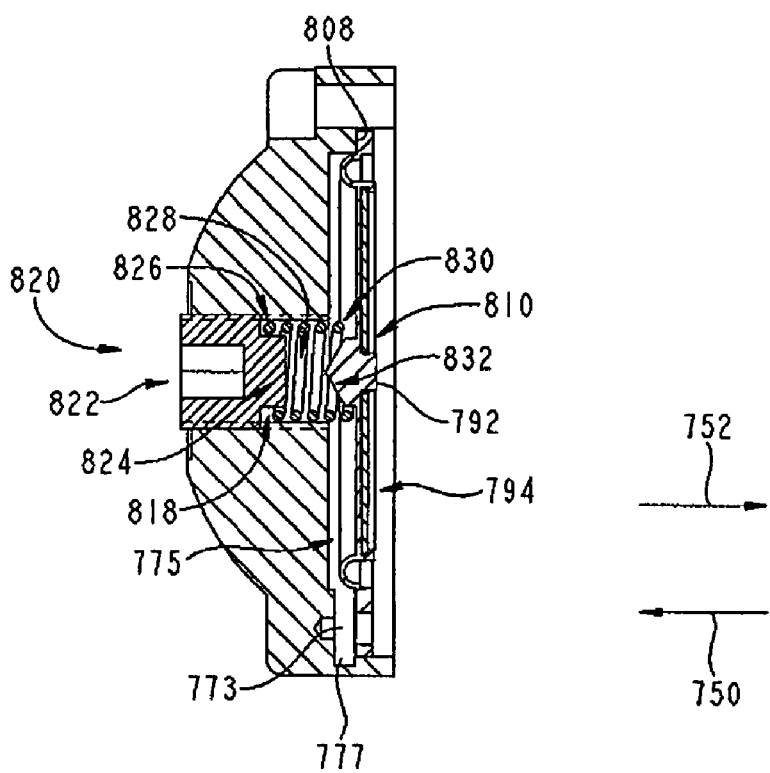
FIG. 27A is a sectional view of the assembly of the third body portion and diaphragm of FIG. 27 taken along lines 27A-27A of FIG. 27.

Referring to FIG. 14, central portion 810 including pad 792 is able to move in directions 750, 752 relative to outer portion 804. Returning to FIG. 56, third body portion 516 includes cavity 775 which permits the movement of diaphragm 794 in direction 750. Referring to FIG. 29, third body portion 516 further includes an aperture 818 which threadably receives an adjuster 820. Referring to FIG. 27A, adjuster 820 includes a tool engagement portion 822 and a tapered portion 824. Tapered portion 824 is configured to receive a first end 826 of a biasing member 828. A second end 830 of biasing member 828 contacts diaphragm 794 generally in central portion 810. As shown, in FIG. 28, in one embodiment, second end 830 of biasing member 828 is received by a bump 832 on diaphragm 794.

Biasing member 828 is used to bias central portion 810 of diaphragm 794 in direction 752 such that pad 792 contacts seat 790 (see FIG. 14). By adjusting how far adjuster 820 is advanced into or out of aperture 818, the amount of force exerted by biasing member 828 on diaphragm 794 may be adjusted. Therefore, the amount of force required to move diaphragm 794 such that pad 792 is spaced apart from seat 790 may be adjusted.

Referring to FIG. 25D, second body portion 514 further includes a fluid channel 771 which connects a front surface 763 of second body portion 514 with back surface 778 of second body portion 514. Referring to FIG. 12C, fluid channel 771 is aligned with recess 688 in first body portion 512 when second body portion 514 is assembled to first body portion 512. As explained in more detail below, fluid channel 771 is further aligned with a fluid channel 773 (see FIG. 27) in third body portion 516 which is in fluid communication with cavity 775 formed between third body portion 516 and diaphragm 794 through fluid passage 777. As such, fluid passage 606 in first body portion 512 is in fluid communication with cavity 775 through recess 688 (first body portion 512), fluid passage 771 (second body portion 514), fluid passage 773 (third body portion 516 and a corresponding fluid passage in diaphragm 794), and fluid passage 777 (third body portion 516). As explained in more detail below this fluid connection permits the inhalation of the patient and/or the exhalation of the patient to serve as a trigger for the operation of conserver portion 504.

Figure 30A:
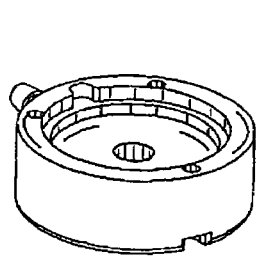
FIG. 30A is a bottom isometric view of a modified third body portion of the fluid conserver application device configured for use with a dual lumen cannula.
Figure 30B:
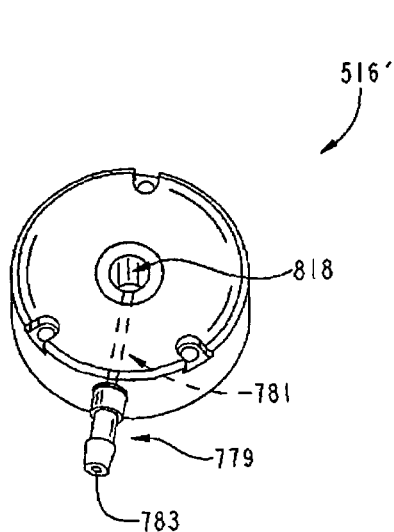
FIG. 30B is a top isometric view of a dual lumen cannula third body portion.

It should be noted that third body portion 516 is for use with the single lumen cannula. Also shown in FIGS. 30A and 30B is a modified third body portion 516' for use with a dual lumen cannula. Dual lumen third body portion 516' is generally similar to third body portion 516. However, dual lumen third body portion 516' does not include fluid passage 773 or fluid passage 777. A second lumen of the dual lumen cannula is instead attached to nipple 779. A fluid passage 783 in nipple 779 is in fluid communication with cavity 775 through fluid passage 781 in third body portion 516'. Fluid passage 781 intersects with aperture 818 below the location of adjuster 820. As such, the inhalation or exhalation of the patient is sensed through the second lumen of the cannula attached to nipple 779 as opposed to through the first lumen and the plurality of fluid passages including fluid passages 773 and 777.

With reference to FIGS. 13, 14, and 14A-D, conserver 500 with the single lumen conserver 502 operates in the following manner. A source of pressurized fluid 522 is coupled to conserver 500 as explained above delivering pressurized fluid ultimately to passages 546, 547, 548 of pressure reduction section 170. Single lumen cannula 503 is coupled to nipple 608. Single lumen cannula 503 is further coupled to a patient. As is well understood in the art, single lumen cannula 503 is configured to provide fluid, such as oxygen, to the patient to aid in breathing.

Fluid from the pressurized source enters fluid passage 528 and passes through fluid passage 546 of pressure reduction section 170. Pressure reduction section 170 provides fluid through fluid passages 547 and 548 at a reduced lower pressure than the pressure of fluid entering pressure reduction section 170 from the source of pressurized fluid 522. As mentioned above fluid passages 547 and 548 communicate fluid to the currently aligned passage 416 of flow selector 400 and passage 221 of axle 220', respectively.

Figure 14A:
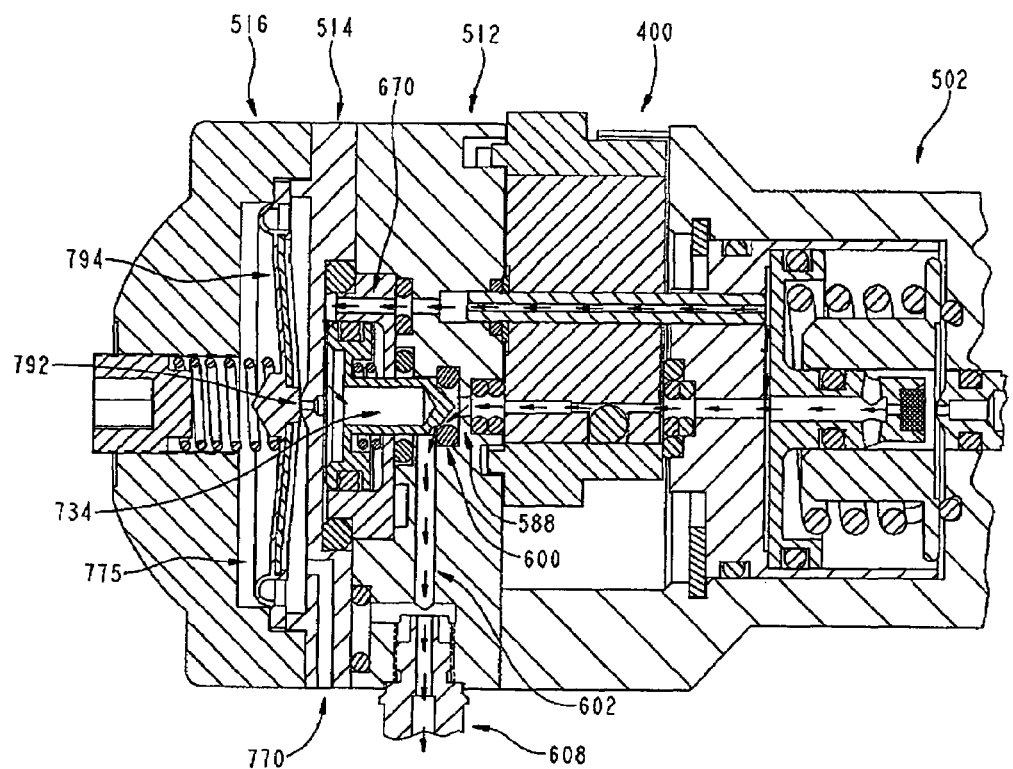
FIG. 14A is a detail view of the sectional view of FIG. 13 illustrates the conserving device of FIG. 14 in a start-up orientation and configured for operation in the intermittent mode of operation.
Figure 14B:
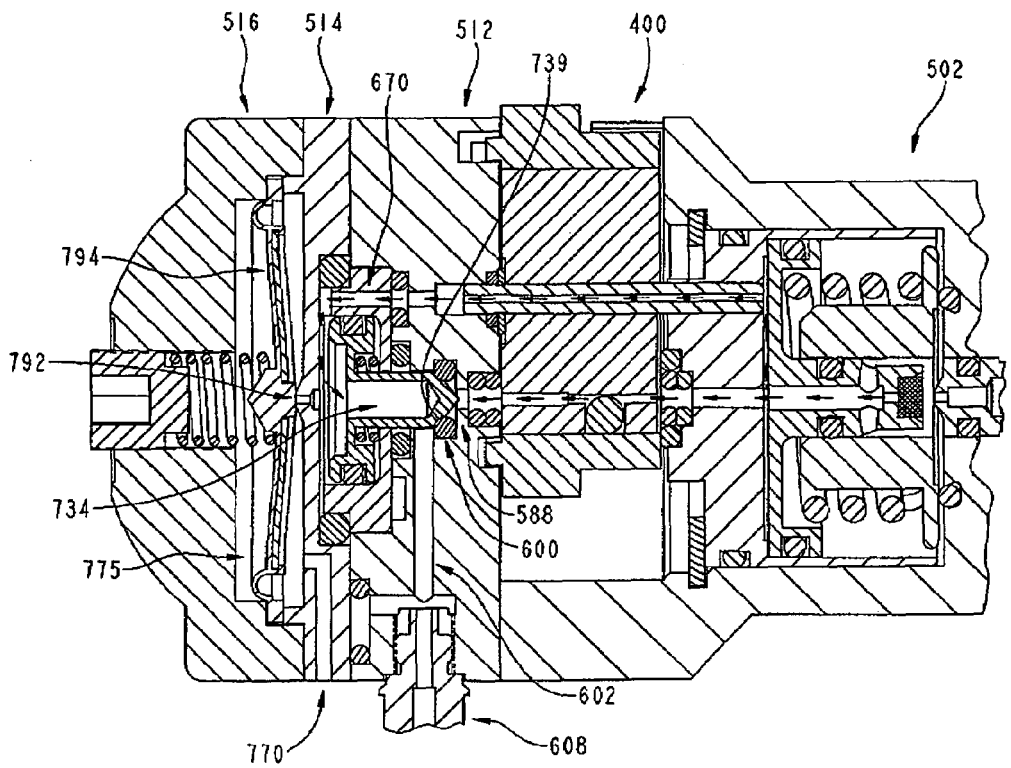
FIG. 14B illustrates the movement of the demand piston in the fluid conserving device to prevent the flow of fluid to the nipple and hence to the cannula due to a build-up of fluid behind the demand piston.
Figure 14C:
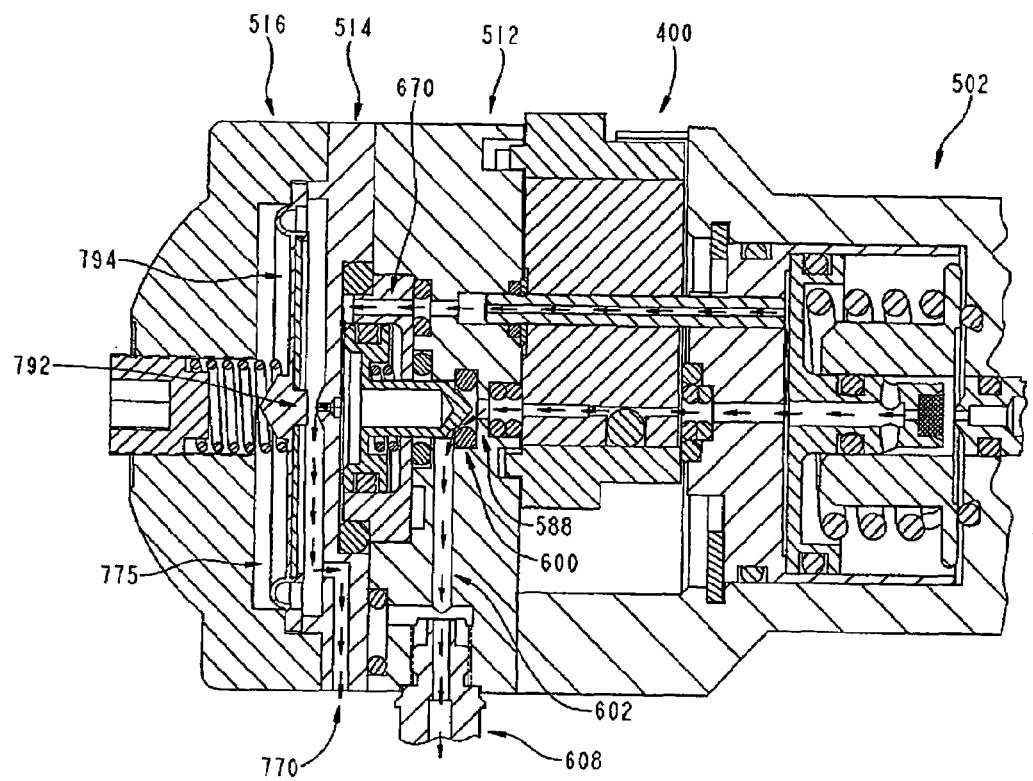
FIG. 14C illustrates the movement of the diaphragm in response to a trigger event, illustratively a patient inhalation, thereby relieving the build-up of fluid behind the demand piston resulting in the subsequent movement of the demand piston to permit the flow of fluid to the nipple and hence to the cannula.
Figure 14D:
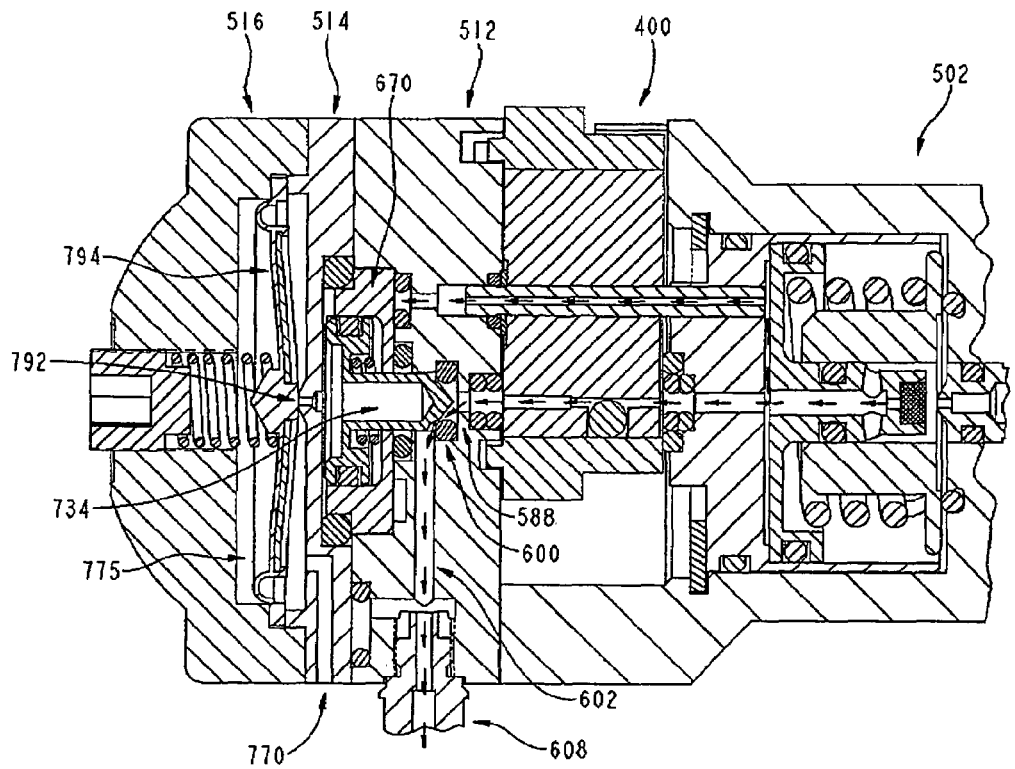
FIG. 14D illustrates the orientation of the components of the fluid conserving device when the fluid conserving device is in the continuous mode of operation.

Conserver portion 504, as shown in FIGS. 14A-C, is operating in the intermittent mode of operation. As such, conserver 504 provides spaced apart pulses of fluid to a patient through cannula 503 which is coupled to nipple 608. The timing of the pulses and the duration of the pulses are controlled by a pneumatic controller comprised generally of demand piston 734. The inputs to the pneumatic controller are discussed below. Conserver portion 504, as shown in FIG. 14D, is operating in a continuous mode of operation wherein a continuous flow of fluid is provided to the patient through cannula 503.

Returning to FIGS. 14A-C, the operation of the pneumatic controller in the intermittent mode of operation is further explained. As discussed herein, the currently aligned passage 416 of flow selector 400 is configured to provide a metered or calibrated restricted flow of fluid, typically in the range of about 0.5 liters per minute to about 5 liters per minute. Fluid exiting passage 416 is passed into passage 588 of first body portion 512. Passage 588 intersects with and is in fluid communication with passage 602 in first body portion 512 unless demand piston 734 blocks the passage of fluid from fluid passage 588 to fluid passage 602. Passage 602 is operably coupled to a nipple 608 which in turn is coupled to single lumen cannula 503 for delivery of fluid to the patient.

FIG. 14A illustrates a startup orientation for conserver portion 504 or the orientation of conserver portion 504 subsequent to the venting of fluid as shown in FIG. 14C. FIG. 14B illustrates the blockage of the flow of fluid from fluid passage 588 to fluid passage 602 by demand piston 734 hence conserving fluid. FIG. 14C illustrates the venting of fluid thereby causing demand piston 734 to be moved such that fluid passes from fluid passage 588 to fluid passage 602.

Returning to FIG. 14A, in the absence of any obstruction, fluid passes from the currently aligned fluid passage 416, to fluid passage 588, to fluid passage 602, and onto the patient through cannula 503. However, reduced portion 740 of demand piston 734 is configured to seal against seal 600 to block the flow of fluid from fluid passage 588 to fluid passage 602 (as shown in FIG. 14B). As explained above, demand piston 734 is biased in direction 750 by biasing member 732 such that reduced portion 740 is spaced apart from seal 600 and fluid passage 588 is in fluid communication with fluid passage 602 (as shown in FIG. 14A). As such, in order to block the flow of fluid from fluid passage 588 to fluid passage 602, demand piston 734 must be moved in direction 752 against the bias of biasing member 732.

The movement of demand position 734 in direction 752 is the result of a build-up of fluid pressure on a back side 735 of demand piston 734 as illustrated in FIG. 14B. Fluid is delivered to back side 735 of demand piston 734 through passage 221 of axle 220'. Passage 221 is in fluid communication with passage 616 of first body portion 512 which in turn is in communication with passage 760 in first mode selector 670. It should be noted that if conserver 504 was operating in a continuous mode of operation as illustrated in FIG. 14D, passage 760 would not be aligned with passage 616 and hence fluid would not be delivered to the back side 735 of demand piston 734. As such, demand piston 734 would be biased in direction 750 by biasing member 732 and fluid passage 602 would be in continuous fluid communication with fluid passage 588.

Returning to the intermittent mode of operation and FIG. 14A, first mode selector 670 and second body portion 514 cooperate to define a cavity 737 proximate to back side 735 of demand piston 734. It should be understood that the pressure of fluid passing through passages 221, 616 and 760 is at a higher pressure than the fluid in passage 588. As such, over time a higher pressure is built up on back side 735 of demand piston 734 and demand piston 734 is moved against the biasing of biasing member 732 in direction 752 resulting in reduced portion 740 sealing against seal 600 such that fluid passage 602 is no longer in fluid communication with fluid passage 588 as illustrated in FIG. 14B.

Reduced portion 740 of demand piston 734 would remain sealed against seal 600 if the higher pressure on back side 735 of demand piston 734 is not relieved. In the illustrated embodiment, the pressure on the back side of 735 is relieved by the permitting of fluid to flow through passage 786 in second body portion 514, through a cavity 787 formed by second body portion 514 and diaphragm 794 and ultimately through vent passage 770 in second body portion 514 to atmosphere as illustrated in FIG. 14C. Once the pressure adjacent back side 735 is relieved, demand piston 734 moves in direction 750 due to the biasing of biasing member 732 resulting in fluid passage 602 again being in fluid communication with fluid passage 588 as illustrated in FIG. 14C.

Central portion 810 of diaphragm 794 is moveable generally in direction 750 from a first position wherein pad 792 is sealed against seat 790 to a second position wherein pad 792 is spaced apart from seat 790 of second body portion 514. When diaphragm 794 is in the first position (see FIGS. 14A and 14B) fluid is prevented or restricted from passing from passage 786 into cavity 787. When diaphragm 794 is in the second position, fluid is permitted to pass from passage 786 into cavity 787 (see FIG. 14C).

Diaphragm 794 is biased in direction 752 (in the first position) by a biasing member 826. As such, diaphragm 794 typically prevents the passage of fluid from passage 786 to cavity 787. However, if the force of biasing member 826 is reduced, then the pressure buildup in fluid passage 786 causes central portion 810 of diaphragm 794 to move in direction 750, thereby permitting fluid to pass from fluid passage 786 into cavity 787 and ultimately to atmosphere.

In one embodiment, the force exerted by biasing member 826 is set such that diaphragm 794 is not moveable in direction 750 solely due to the build-up of pressure on backside 735 of demand piston 734. In this embodiment, conserver 500 requires a trigger to initiate the intermittent flow of fluid to the patient through the single lumen cannula.

In the illustrated embodiment, the trigger is the inhalation of the patient. When the patient inhales, the pressure in cannula 503 is reduced. The reduction in pressure in cannula 503 is communicated to cavity 775 formed by third body portion 516 and diaphragm 794 through the connection of fluid passages 690 (in first body portion 512), 688 (in first body portion 512), 771 (in second body portion 514), 773 (in third body portion 516), and 777 (in third body portion 516) as shown in FIG. 12C. When dual lumen third body portion 516' is used, the reduction in pressure in the cannula is communicated to cavity 775 through the second lumen attached to nipple 779. The reduction in pressure in cavity 775 aids in the ability to move diaphragm 794 in direction 750 because the reduction in pressure effectively reduces or negates at least a portion of the force exerted by biasing member 826. Further, the combination of the reduction in pressure in cavity 775 and the buildup of pressure on the backside 735 of demand piston 734 overcomes the force of biasing member 826 resulting in diaphragm 794 moving in direction 750 (see FIG. 14C).

Therefore, as the patient inhales central portion 810 of diaphragm 794 is moved in direction 750 against the bias of biasing member 826 due to the buildup of pressure on backside 735 of demand piston 734 and the reduction of pressure in cavity 775 due to the patient inhaling as illustrated in FIG. 14C. Once the seal between pad 792 of diaphragm 794 and seat 790 is lost, the fluid at backside 735 of demand piston 734 is communicated to atmosphere. As the pressure in cavity 737 corresponding to back side 735 decreases, demand piston 734 is moved in direction 750 such that reduced portion 740 is spaced apart from seal 600 and pad 792 of diaphragm 794 returns to seal against seat 790 (see FIG. 14A). The pressure again builds up on backside 735 of demand piston 734 until demand piston 734 is again moved in direction 752 (see FIG. 14B). The further building of pressure in cavity 737 along with the continued reduction in pressure in cavity 775 results in diaphragm 794 and demand piston 734 being once again moved in direction 750 providing a second pulse of fluid (see FIG. 14C). The above cycle is repeated again as long as the pressure in cavity 775 is reduced due to the inhalation of the patient.

Once the patient stops or significantly reduces inhaling and/or is exhaling, the pressure reduction in cavity 775 is lost and/or the pressure in cavity 775 is increased and the force of biasing member 826 is able to completely overpower the force of the pressure buildup on backside 735 in cavity 737. As such, the absence or significant reduction of inhalation and/or the presence of exhalation provides a second trigger to cease the intermittent production of pulses of fluid. The number of pulses of fluid and spacing of the pulses is in part dependent on the breath length and breath depth of the patient.

In one example, the controller inputs or variables discussed herein are set such that two pulses are provided during an exemplary inhalation of a patient. In another example, about 6 to about 10 pulses of fluid are provided during an exemplary inhalation of a patient. In a further example, about 2 to about 10 pulses of fluid are provided during an exemplary inhalation of a patient. In still a further example, about 8 to about 9 pulses of fluid are provided during an exemplary inhalation of a patient.

Figure 15:
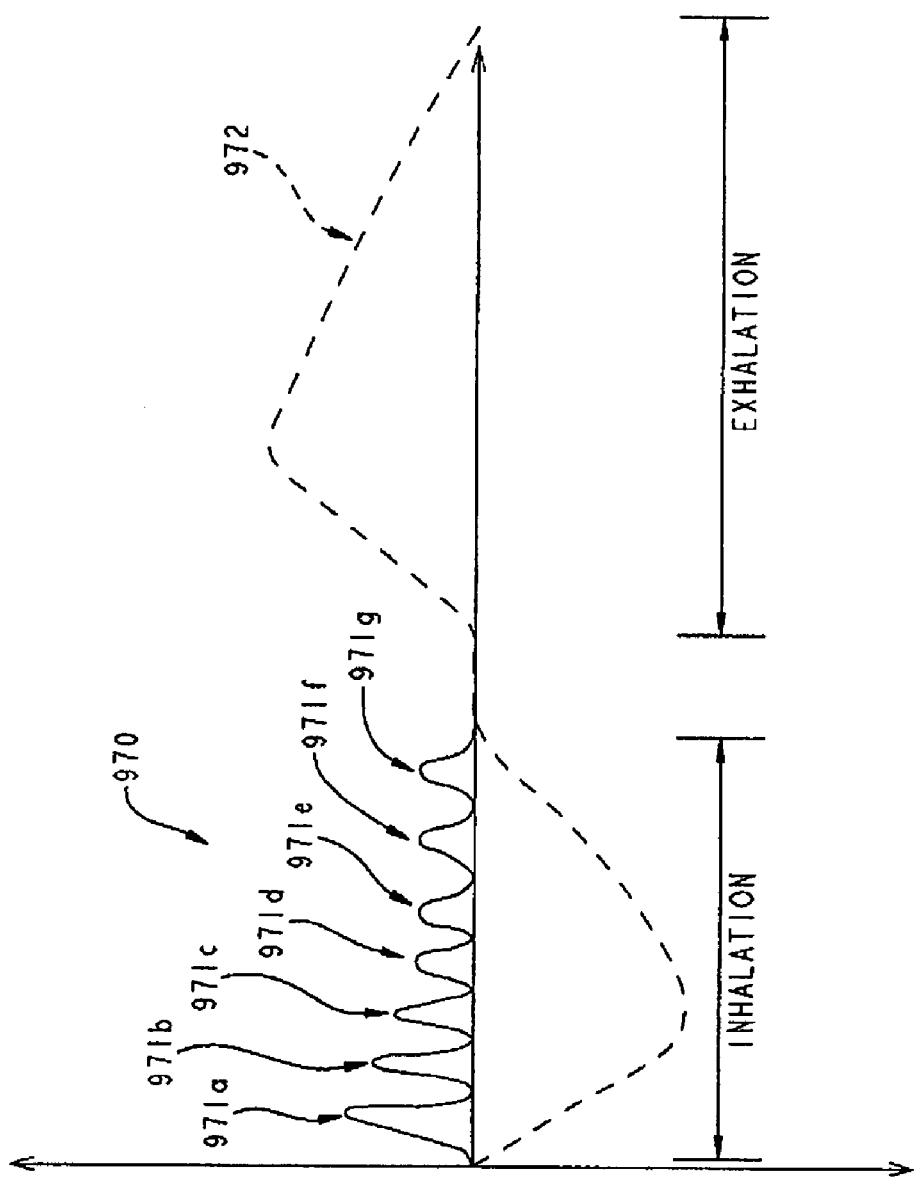
FIG. 15 shows exemplary pulses of fluid being provided by the conserving device of FIG. 10 relative to an exemplary breathing cycle of a patient connected to a single lumen cannula.

Referring to FIG. 15, the flow of fluid from passage 588 to passage 602 is represented by curve 970 and an exemplary curve 792 of the pressure in cavity 775 is shown. Curve 792 is generally shaped like a breath curve for a patient due to the fact that cavity 775 is in fluid communication with fluid passage 602 and cannula 503. The overall shape of curve 970 is generally sinusoidal. Illustratively, curve 970 includes seven pulses of fluid 971A-G as shown in FIG. 15. The earlier pulses 971A and 971B generally provide a larger flow rate of fluid due to the pressure buildup in fluid passage 588. The latter pulses 971E-G exhibit a generally constant flow rate of fluid from pulse to pulse. As such, the fluid flow to cannula 503 is somewhat front loaded to the beginning of an inhalation cycle of the patient. Also, as shown in FIG. 15, the spacing between the latter pulses 971*f* and 971*g* is greater than the spacing between the earlier pulses 971A and 971B due at least in part to the return of the pressure in cavity 775 towards the baseline pressure near the end of the inhalation of the patient.

The amount of fluid communicated to cannula 503 in pulses 971A-G generally corresponds to the metered or calibrated flow of fluid specified by flow setting of conserver 500 assuming that the patient is taking an expected average number of breathes each minute and that each breath has a generally constant length and depth. However, conserver 500 is configured to provide fluid to the patient for every breath and multiple pulses for each breath. As such, a patient which is in a period of activity, such as walking, will likely take more breathes per minute and potentially deeper and/or different length breathes. In such situations, conserver 500 provides a specified amount of fluid to the patient that exceeds the flow setting. Alternatively, if the patient is in a period of inactivity, the patient will likely take fewer breathes per minute and potentially shallower and/or different length breathes. In such situations, conserver 500 provides a specified amount of fluid to the patient that is less than the flow setting. As such, conserver 500 is configured to provide a specified amount of fluid to a patient corresponding to a flow setting for times when the patient is experiencing average breathing characteristics and to adapt to the breathing pattern of the patient for other times, such as activity.

The spacing of the pulses and the widths of the pulses are controlled by varying one or more of the controller inputs discussed herein. In one example, the controller inputs are set such that at least two pulses of fluid are provided for an exemplary inhalation cycle of a patient.

Referring to FIG. 15A, a comparison was performed between conserver 500 as shown herein and embodied as the Flo-Rite™ conserver available from Ameriflo Corporation located at 478 Gradle Drive, Carmel, Ind. 46032, the Easy-Pulse5 conserving regulator available from Precision Medical located at 300 Held Drive, Northampton, Pa. 18067, and the Cypress OXYPneumatic® conserver, Model 511, available from Chad Therapeutics located at 21622 Plummer Street, Chatsworth, Calif. 91311. Each device was connected to a mechanical simulator to simulate patient breathing. Each device was tested with the simulated breath curve 980 including three breaths 982*a*, 982*b*, and 982*c*. The EasyPulse5 device gave a single pulse of fluid 984*a*, 984*b*, and 984*c* at the beginning of the respective breaths 982*a*, 982*b*, and 982*c*. The Cypress OXYPneumatic® device gave a single pulse of fluid 986*a*, 986*b*, and 986*c* for respective breath 982*a*, 982*b*, and 982*c*. Both the EasyPulse5 device and the Cypress OXYPneumatic® device provided a second pulse at the end of breath 982*c*. Such a second single large pulse is very uncomfortable for the patient. In addition the Cypress OXYPneumatic® device gave a large percentage of pulse 986*b* outside of the timeframe of the simulated inhale associated with breath 982*b*.

In contrast to the EasyPulse5 and Cypress OXYPneumatic® devices, the Flo-Rite™ device provides intended multiple pulses 988*a* (five pulses), 988*b* (three pulses), and 988*c* (eleven pulses) during the inhalation associated with each breath 982 and did not provide pulses 988 outside of the respective inhalation of each breath 982. As such, the patient is not subjected to a large pulse while they are trying to exhale. The overall shape of pulses 988 are generally sinusoidal. The multiple pulses of each pulse set 988, in one embodiment, may be considered a high frequency oscillator output.

Further, the multiple pulses 988a, 988b, and 988c of the Flo-Rite™ device are generally loaded towards the beginning of the inhalation cycle of each breath 982 as exemplified by the larger amplitudes of the initial pulses of each pulse set 988a, 988b, and 988c. Further, the Flo-Rite™ device is able to provide additional fluid for longer breathes, such as breath 982c, and to provide less fluid for shorter breathes, such as breath 982b. As such, the Flo-Rite™ device is able to adapt to changes in the fluid needs of the patient, such as when the patient is active.

By giving additional pulses when the patient breath length or depth increases, the Flo-Rite™ device is able to reduce the oxygen saturation recovery times for patients using the Flo-Rite™ device. In one example, the recovery time of a patient with the Flo-Rite™ device was less than about one minute, preferably about one-half of a minute. In another example, the recovery time was about 35 seconds.

Further, the Flo-Rite™ device provides multiple pulses throughout the inhalation cycle of breath 982. The multiple pulses reduces fluid flow reversion and/or reflective losses because the multiple pulses are easier on the body. Also, the multiple pulses reduces the likelihood of lung over-distension and improves patient comfort.

The pneumatic controller of the present invention includes a valve assembly in communication with a fluid passage of the body as discussed above. The pneumatic controller is configured to detect an inhalation of the patient and to provide a series of at least two pulses of the fluid 988a, 988b, and 988c to the output during the inhalation of the patient. The pneumatic controller provides an initial pulse having a fluid amplitude greater than a fluid amplitude of subsequent pulses in the series of at least two pulses without the aid of a fluid reservoir separate from the fluid passage of the body.

The present invention includes a needle control valve 642 in portion 620 of fluid passage 616 which adjusts the flow of fluid from fluid outlet passage 618 to the third portion 622 of fluid passage 616. This permits an oscillation frequency of the sinusoidal fluid pulses to be varied by adjusting the needle valve 642.

In another embodiment, the force on biasing member 826 is set low enough that the pressure build-up on back side 735 of demand piston 734 alone can move diaphragm 794 in direction 750. In this embodiment, conserver 500 is able to provide intermittent pulses of fluid to a patient independent of the breathing force of the patient. Such a configuration may provide extra safety in certain environments, such as pediatric environments or with a patient who is capable of only very shallow breathes which result in minimal pressure reduction in cavity 775.

In still a further embodiment, the force on biasing member 826 is set such that a slight pressure reduction in cavity 775 along with the pressure build-up on back side 735 of demand piston 734 together can move diaphragm 794 in direction 750. As such, conserver 500 still uses a trigger from the breath of the patient, but only requires a minimal amount of pressure reduction for increased safety for certain environments, such as pediatric environments or with a patient who is capable of only very shallow breathes which result in minimal pressure reduction in cavity 775. In one example, the pressure reduction in cavity 775 must be at least about 0.15 cm of water. In another example, the pressure reduction in cavity 775 must be at least about 0.25 cm of water. In yet another example, the pressure reduction in cavity 775 must be at least about 0.35 cm of water.

The pneumatic controller has several inputs or variables each of which has an effect on the timing of the pulses and the duration of the pulses. Primary inputs include the stiffness of biasing member 732, the stiffness of biasing member 826, the stiffness of diaphragm 794, the rate of fluid flow through fluid passages 221 (axle), 616 (first body portion), and 760 (first selector member), the flow rate of fluid through fluid passage 416 (flow selector) and 588 (first body portion), and the size of cavity 737 on the backside of the demand piston.

The values of at least some of these primary inputs are adjustable by a user to calibrate conserver 500, thereby providing variable inputs to the controller. For instance, the effective stiffness of biasing member 826 can be adjusted by further movement of adjuster 820 in one of directions 750 and 752. Further, the flow rate of fluid in fluid passage 616 and hence in fluid passage 760 may be adjusted by adjusting the position of tip 644 of needle control valve 642 in portion 620 of fluid passage 616. Although these inputs may be available to an end user, such as a caregiver, in one embodiment these inputs are not readily available to an end user.

Typically, an end user or caregiver user has two main variable inputs to the pneumatic controller. First, the selection of flow rate to passage 588 by rotating flow selector 400 to select a fluid passage 416 of flow selector 400. By increasing the flow rate by selecting a fluid passage having a higher fluid flow rate, the pneumatic controller will decrease the spacing between pulses (increase the frequency of the pulses) and/or increase the amplitude of each pulse. Conversely, by decreasing the flow rate by selecting a fluid passage having a lower fluid flow rate, the pneumatic controller will increase the spacing between pulses (decrease the frequency of the pulses) and/or decrease the amplitude of each pulse.

Second, the selection of whether to operate in a continuous mode of operation or an intermittent mode of operation by the rotation of second selector member 672. The intermittent mode of operation of conserver 504 is described herein with reference to FIGS. 14A-C and in a dual lumen embodiment, with reference to FIG. 30A. The continuous mode of operation of conserver 504 is described herein with reference to FIG. 14D. When second selector member 672 is moved to select a continuous mode of operation, first selector member 670 is rotated such that passage 760 is no longer in line with passage 616 of first body portion 512. As such, fluid cannot reach the back side 735 of demand piston 734 from fluid passage 616. Thus, biasing member 732 moves demand piston 734 in direction 750 which brings fluid passage 602 into fluid communication with fluid passage 588. Since, demand piston 734 is not moved in direction 752 due to a buildup of pressure on the backside of demand piston 734, the flow of fluid into passage 602 is continuous.

In an alternative embodiment, the pneumatic controller is replaced with an electronic controller which includes a processor with software or firmware configured to control the timing of the pulses and the duration of each pulse. The electronic controller still can use a trigger, such as a detection of the inhalation of the patient to start the intermittent flow of fluid and/or the detection of the absence of inhalation and/or the presence of exhalation of the patient to stop the intermittent flow of fluid.

In the illustrated embodiment shown in FIGS. 10-30, conserver 500 is able to operate in either an intermittent mode of operation or a continuous mode of operation for any of the selected fluid passages 416 of flow selector 400 because the flow selector 400 operates independent of first mode selector 670 and second mode selector 672 of the continuous or intermittent selector. By having the continuous or intermittent selector operate independent of flow selector 400, a low continuous flow, such as a flow corresponding to fluid passage 416a may be implemented without the need to subject a patient to higher flow rates in order to select a continuous flow.

However, in some embodiments it is not desirable to provide a continuous flow of fluid to a patient at certain flow rates, particularly higher flow rates. Referring to FIGS. 31-34, various components of conserver 500 are modified such that the ability to select continuous or intermittent modes of operation with the continuous or intermittent selector and/or flow rates with flow selector 400 is dependent on the current selection of the other of the continuous or intermittent selector and flow selector 400.

The modified conserver 500 includes an interlock 900 which connects flow selector 400 with one of first mode selector 670 and second mode selector 672 of the continuous or intermittent selector. Interlock 900 prevents the selection of a continuous mode of operation with the continuous or intermittent selector 670, 672 for one or more selections of fluid passages 416 of flow selector 400 and further prevents the selection of one or more selections of flow selector 400 while the continuous or intermittent selector 670, 672 is in the continuous mode of operation. It should be appreciated that interlock 900 may also be configured to prevent the selection of one or more flow selections when continuous or intermittent selector 670, 672 is in the intermittent mode of operation and/or the selection of the intermittent mode of operation for one or more flow selections of flow selector 400.

Figure 31:
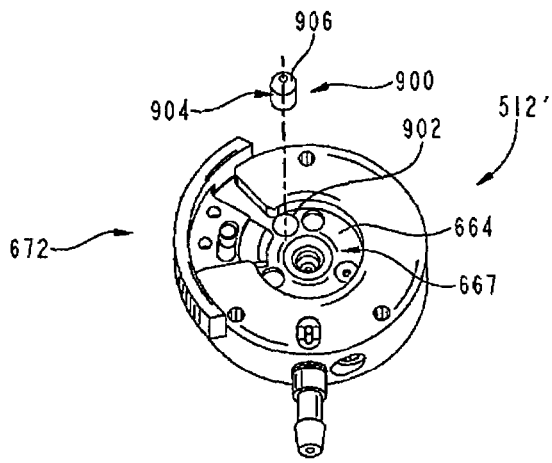
FIG. 31 is an exploded assembly of a modified second body portion of the fluid conserver application device to include an interlock member.

Referring to FIG. 31, a modified second body portion 512' includes a cavity or opening 902 which extends from axial surface 664 of recess 667 through to alignment feature 634 (see FIG. 33) of modified second body portion 512'. A coupler 904 is positioned within cavity 902 and is able to move within cavity 902 such that an engagement surface 906 of coupler 904 is able to protrude out from surface 664 and into alignment feature 634. In one embodiment, coupler 904 is a pin having rounded ends. In another embodiment, coupler 904 is a plurality of spherical balls positioned in cavity 902, such as two spherical balls.

Figure 32:
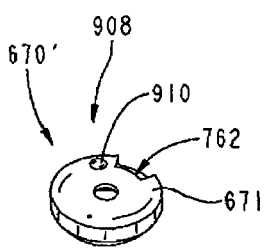
FIG. 32 is a bottom isometric view of the bottom side of a modified second mode selector member of FIG. 23 configured to interact with the interlock member of FIG. 31.
Figure 33:
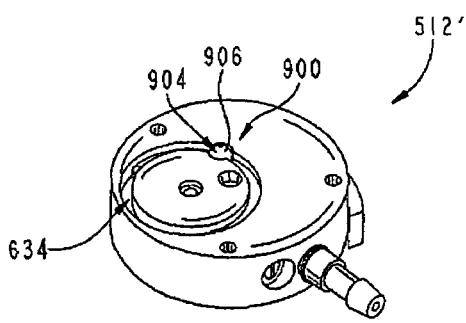
FIG. 33 is a bottom isometric view of the second body portion of FIG. 31 with the interlock member assembled thereto.

Referring to FIG. 32, a modified first mode selector member 670' is shown. First mode selector 670' includes a recess 908 having an engagement surface 910. Recess 908 is sized to receive a portion of coupler 904 such that engagement surface 906 of coupler 904 can engage engagement surface 910 of first selector 670'. When coupler 904 is received by recess 908 and coupler 904 is prevented from egressing from recess 908, first mode selector member 670' is unable to move relative to second body portion 512'. As such, a user is unable to impart a rotation to second mode selector 672 causing the rotation of first mode selector 670'.

In the illustrated embodiment, recess 908 is positioned such that coupler 904 is received by recess 908 when continuous or intermittent selector is in the intermittent mode of operation. When continuous or intermittent selector is in the continuous mode of operation coupler 904 and recess 908 are not aligned and hence coupler 904 cannot advance into recess 908.

Figure 34:
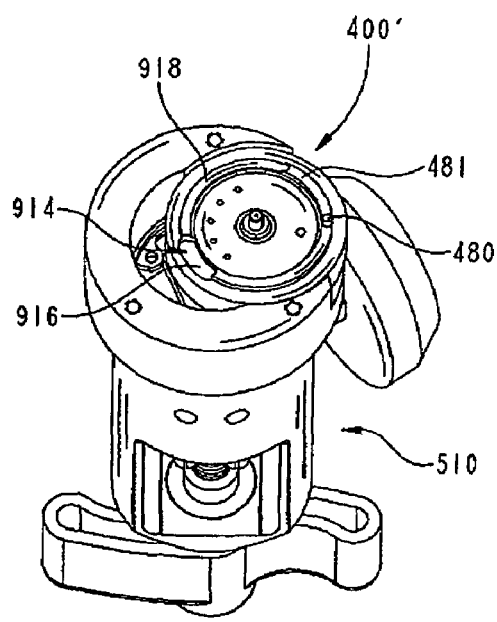
FIG. 34 shows a modified version of the flow selector member of FIG. 5A configured to interact with the interlock member of FIG. 31.

Referring to FIG. 34, a modified flow selector 400' is shown. Flow selector 400' includes a recess 914 having an engagement surface 916. Flow selector 400' further includes a top surface 918 of ridge 481. Recess 914 is sized to receive a portion of coupler 904 such that engagement surface 906 of coupler 904 can engage engagement surface 916 of flow selector 400'. When coupler 904 is received by recess 914 and coupler 904 is prevented from egressing out of recess 914, the movement of flow selector 400' is further limited. Illustratively, flow selector 400' can only be moved to align adjacent fluid passages 416a and 416b with fluid passage 547 when coupler 904 is received by recess 914. As such, a user is unable to impart a rotation to flow selector 400' to select another fluid passage besides, fluid passages 416a and 416b. In one embodiment, recess 914 is sized to only permit the alignment of a single fluid passage 416. In another embodiment, recess 914 is sized to permit the alignment of multiple spaced apart fluid passages 416 while blocking the selection of at least one intervening fluid passage 416.

In the illustrated embodiment, recess 914 is positioned such that coupler 904 is received by recess 914 when flow selector 400' is oriented such that one of fluid passages 416A and 416B are aligned with fluid passage 547. When flow selector 400' is oriented such that one fluid passages 416C-416F are aligned with fluid passage 547 coupler 904 and recess 914 are not aligned and hence coupler 904 cannot advance into recess 914.

The operation of interlock 900 is explained below with the aid of four examples. In a first example, flow selector 400' is oriented such that fluid passage 416b is aligned with fluid passage 547 and first mode selector 670' of continuous or intermittent selector is in the orientation corresponding to the intermittent mode of operation. In this first example, a user desires to change conserver 500' to a continuous flow and to maintain fluid passage 416B in alignment with fluid passage 547 which is a change permitted by interlock 900. As such, a user imparts a rotation to second mode selector 672 which in turn imparts a rotation to first mode selector 670'.

It should be noted that when first selector 670' is oriented in the intermittent mode of operation, recess 908 and coupler 904 are aligned. In order for first selector 670' to be rotated to the orientation corresponding to the continuous mode of operation, coupler 904 must be egressed out of recess 908. However, coupler 904 can only be egressed out of recess 908 when recess 914 of flow selector 400' is aligned with coupler 904. If recess 914 and coupler 904 are not aligned, coupler 904 contacts surface 918 which prevents the egression of coupler 904 from recess 908.

However, in the example given coupler 904 and recess 914 are aligned. As such, the rotation imparted to first mode selector 670' results in coupler 904 being egressed out of recess 908 such that engagement surface 906 of coupler 904 is now in contact with surface 671 of first selector 670' and is advanced into recess 914 of flow selector 400'.

In a second example, flow selector 400' is oriented such that fluid passage 416D is aligned with fluid passage 547 and first mode selector 670' of continuous or intermittent selector is in the orientation corresponding to the intermittent mode of operation. In this second example, a user desires to change conserver 500' to a continuous flow and to maintain fluid passage 416D in alignment with fluid passage 547 which is a change prohibited by interlock 900.

The user attempts to impart a rotation to second mode selector 672 which in turn would result in a rotation of first mode selector 670'. However, since flow selector 400' is oriented such that fluid passage 416d is aligned with fluid passage 547 recess 914 and coupler 904 are not aligned and coupler 904 is prevented from advancing into recess 914, but rather contacts surface 918. Therefore, coupler 904 cannot be egressed out of recess 908 and first selector 670' cannot be rotated relative to second body portion 512'. The end result being that conserver 500' cannot be changed to a continuous mode of operation in this example.

In a third example, flow selector 400' is oriented such that fluid passage 416A is aligned with fluid passage 547 and first selector 670' of continuous or intermittent selector is in the orientation corresponding to the intermittent mode of operation. In this third example, a user desires to change conserver 500' such that it is still in an intermittent mode of operation and to place fluid passage 416D in alignment with fluid passage 547 which is a change permitted by interlock 900.

The user rotates flow selector 400' to orient fluid passage 416D with fluid passage 547. Coupler 904 must egress from recess 914 in order for flow selector 400' to be so oriented. Since conserver 500' is in the intermittent mode of operation, recess 908 in first mode selector 670' is aligned with coupler 904 and coupler 904 can be advanced into recess 908 as it is being egressed from recess 914.

In a fourth example, flow selector 400' is oriented such that fluid passage 416A is aligned with fluid passage 547 and first mode selector 670' of continuous or intermittent selector is in the orientation corresponding to the continuous mode of operation. In this third example, a user desires to change conserver 500' such that it is still in a continuous mode of operation and to place fluid passage 416D in alignment with fluid passage 547 which is a change prohibited by interlock 900.

The user attempts to rotate flow selector 400' to orient fluid passage 416D with fluid passage 547. Coupler 904 must egress from recess 914 in order for flow selector 400' to be so oriented. Since conserver 500' is in the continuous mode of operation, recess 908 in first mode selector 670' is not aligned with coupler 904 and coupler 904 cannot be advanced into recess 908 as it is attempting to be egressed from recess 914. Therefore, the user is unable to rotate flow selector 400' such that fluid passage 416D is aligned with fluid passage 547.

As explained herein, conserver 500 provides multiple pulses of fluid per breath of the patient. Conserver 500 may also be configured to provide a single pulse of fluid to the patient per breath. In one embodiment, the single pulse generally corresponds to the inhalation portion of the patient's breathing cycle. In one example the length of the pulse is about 150-200 mSec. The length of the pulse may be adjusted over a narrow range with the setting of the needle valve. To set conserver 500 to provide multiple pulses of fluid per breath needle valve 642 is positioned within fluid passage 616 to permit about 500 cc/min to about 750 cc/min flow through fluid passage 616. To set conserver 500 to provide a single pulse of fluid per breath needle valve 642 is positioned within fluid passage 616 to permit about 30 cc/min to about 50 cc/min, to about 100 cc/min, to about 150 cc/min, to about 250 cc/min.

Referring to FIGS. 35-51, a conserver 1000 is illustrated. Conserver 1000 is generally similar to conserver 500 and like conserver 500 may be configured to operate in a continuous mode of operation or an intermittent mode of operation. During the intermittent mode of operation conserver 1000 may provide a single pulse of fluid to a patient during the inhalation phase of the patient or may provide multiple pulses of fluid to a patient during the inhalation phase of the patient. The above discussion related to conserver 500 is equally applicable to the discussion of conserver 1000 including the portions related to the sensing of the inhalation and/or exhalation of the patient.

Figure 35:
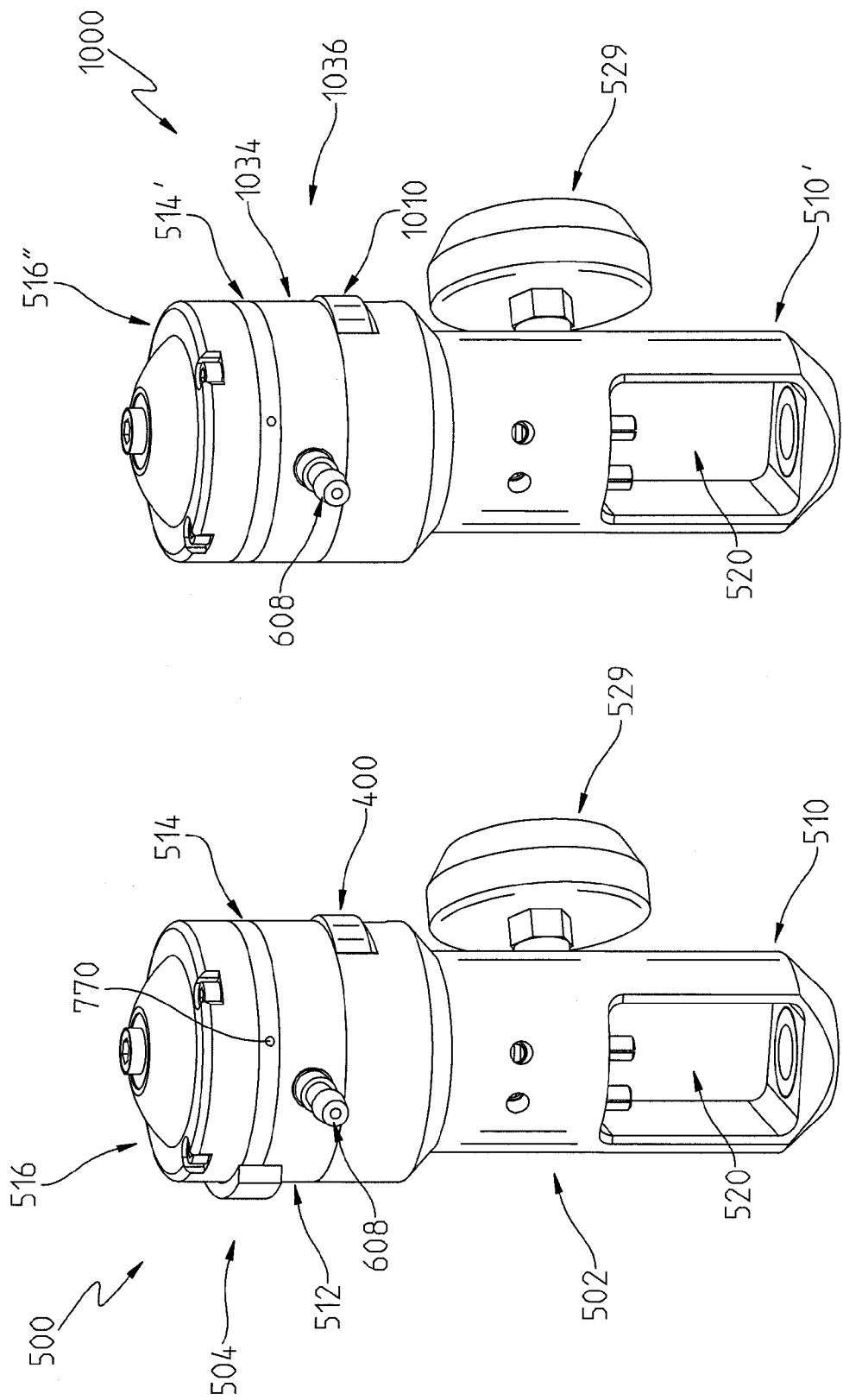
FIG. 35 provides a side-by-side comparison of the conserver of FIG. 10 and a further exemplary conserver.

Referring to FIG. 35, conserver 1000 includes a first body portion 510' which is generally identical to first body portion 510 of conserver 500. First body portion 510' includes an identical fluid inlet 531 and pressure reduction section 170. Further, body portion 510' of conserver 1000 includes a yoke 520 which cooperates with a retainer 527 to couple body portion 510' to a source of pressurized fluid.

Figure 37:
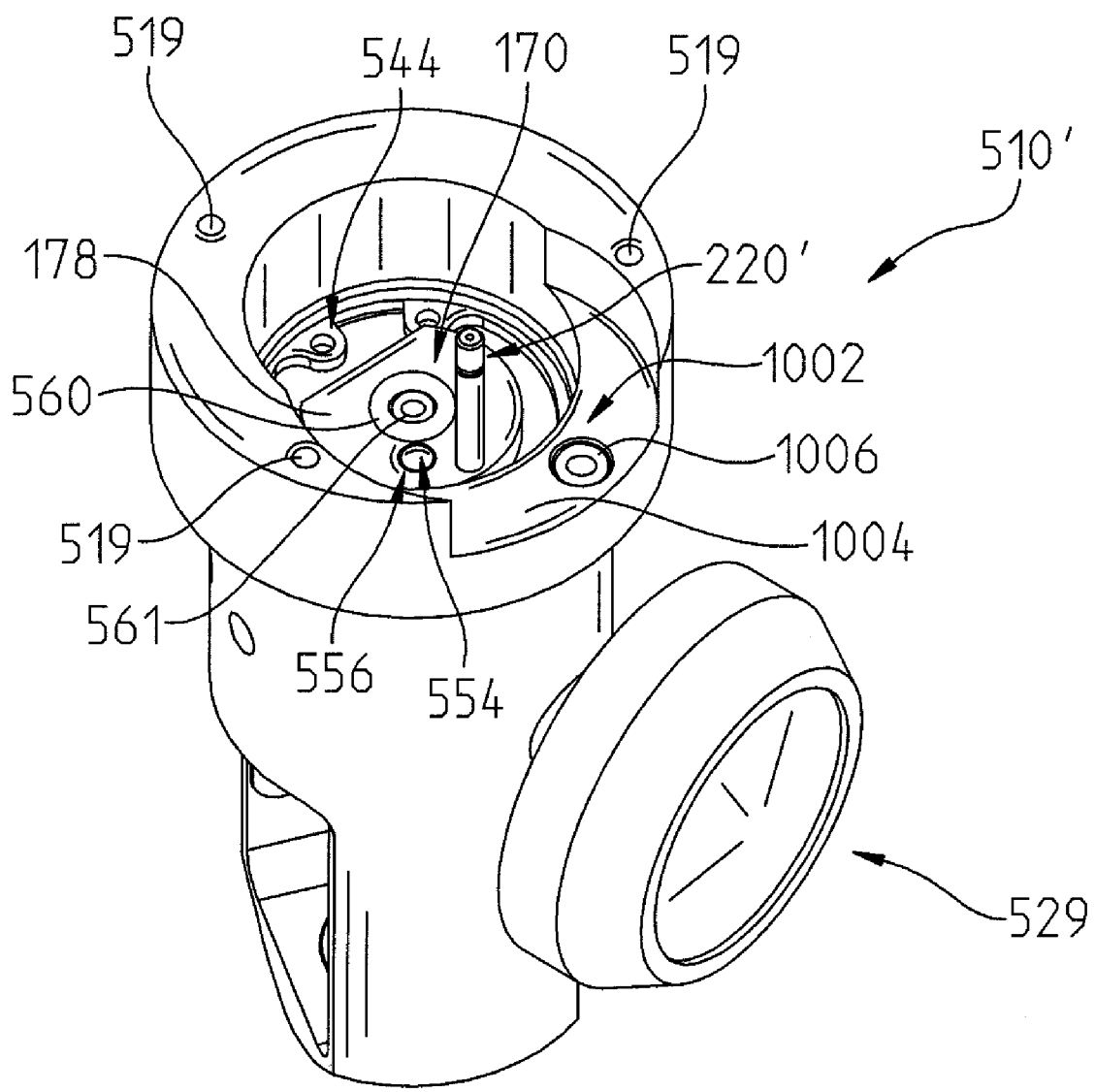
FIG. 37 is an isometric view of a first body portion of the exemplary conserver of FIG. 35 with a pressure reduction section assembled thereto.

Referring to FIG. 37, pressure reduction section 170 is secured to body portion 510' with a retainer 544. Axle 220' is coupled to housing 178 of pressure reduction section 170. As explained below, the fluid passage through axle 220' provides fluid to a backside of demand piston 734 in a similar manner as in conserver 500. This pressure, as in conserver 500, as long as not vented is used to move demand piston 734 towards seal 600 to shut off the flow of fluid to cannula 503.

As explained above in connection with conserver 500, fluid passage 547 communicates fluid to the fluid passage 416 of flow selector 400 aligned with fluid passage 547. As explained above in connection in with FIG. 14, seal 560 and two additional seals 560, 561 assist to prevent or minimize the escape of fluid as fluid passes from fluid passage 547 in pressure reduction section 170 into fluid passage 416 of flow selector 400.

Figure 38:
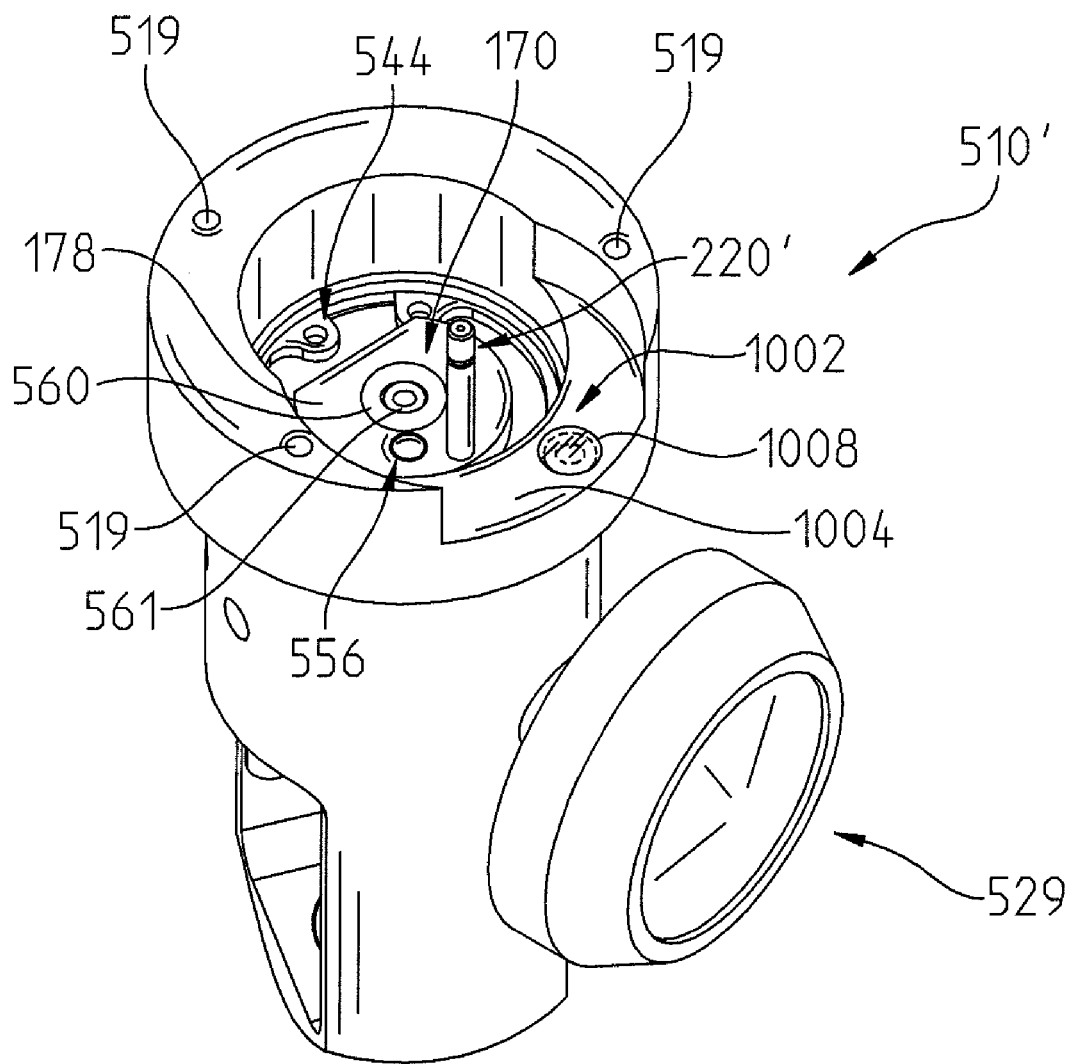
FIG. 38 is the isometric view of FIG. 37 illustrating a support provided for a flow selector.
Figure 51:
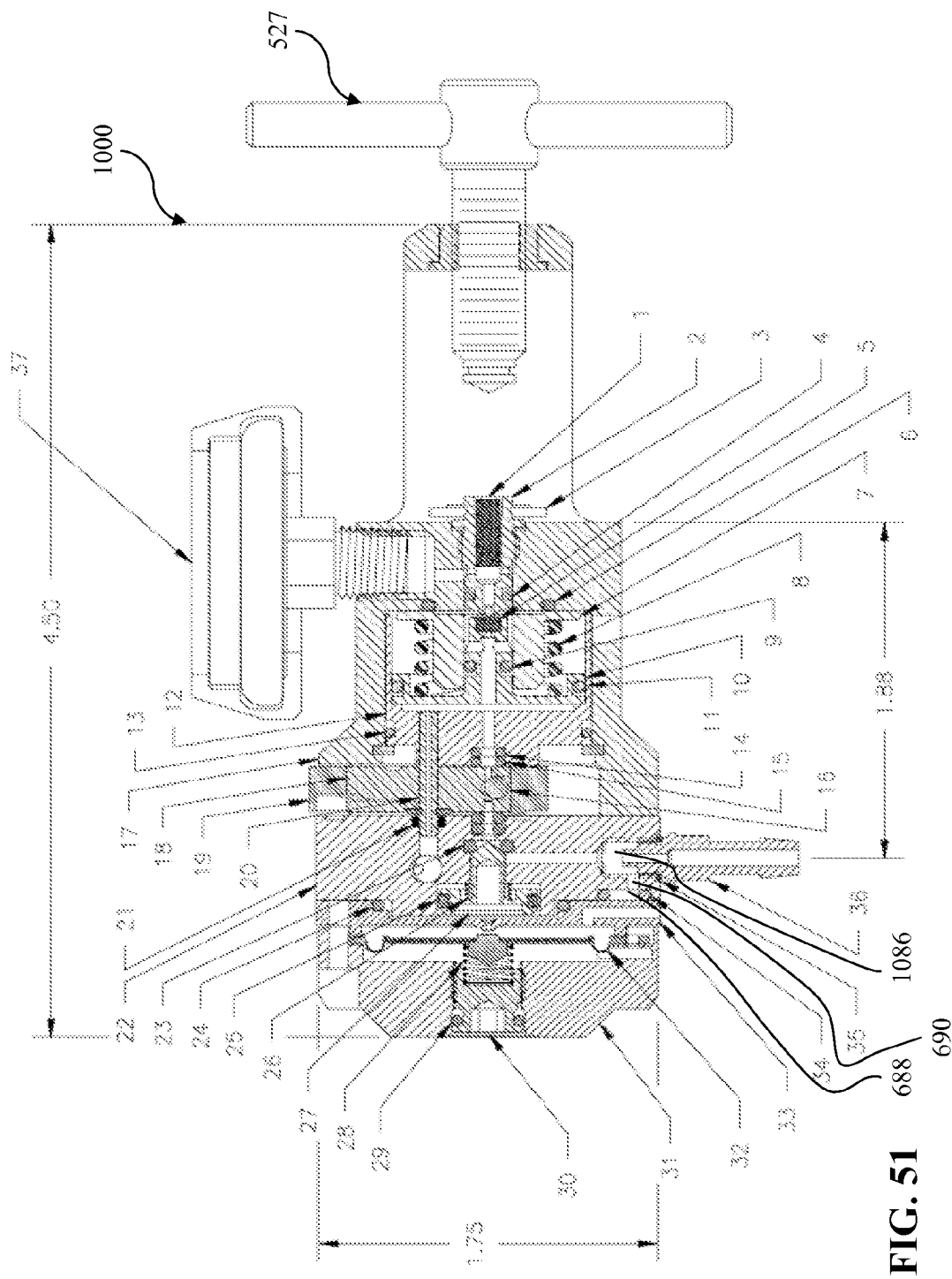
FIG. 51 is a sectional representation of the exemplary conserver of FIG. 35.

Referring FIGS. 37 and 38, body member 510' includes a recess 1002 in an axial surface 1004 of body member 510'. A seal 1006 is placed in recess 1002. Further, as shown in FIG. 38 a support 1008 is positioned on top of seal 1006. In one embodiment, support 1008 is a disc spacer piece made of a polymeric material, such as Teflon or Kel-F. Support 1008 and seals 560 and 561 each contact a rear surface 441 of flow selector 400 when flow selector 400 is assembled to axle 220' as generally shown in FIG. 51. Support 1008 assists in balancing flow selector 400 and keeping seals 560, 561 in constant contact with rear surface 441 of flow selector 400.

Figure 39:
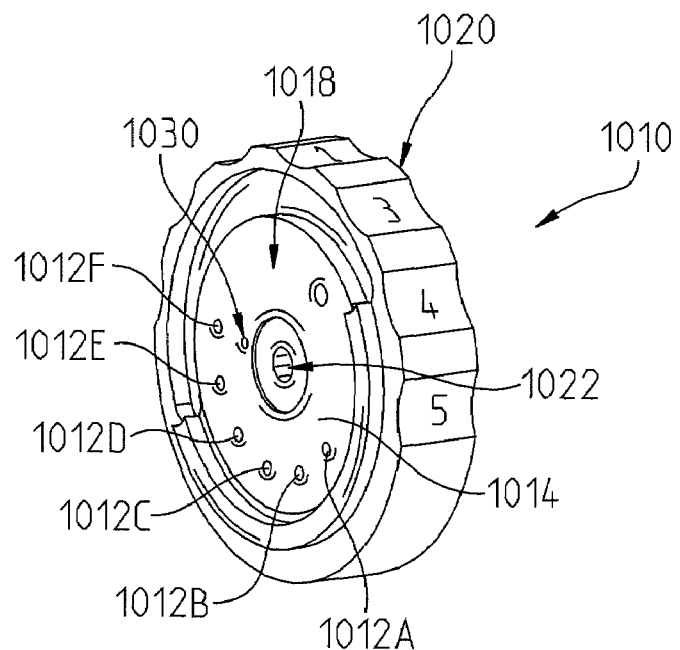
FIG. 39 is an isometric view of an exemplary flow selector.
Figure 40:
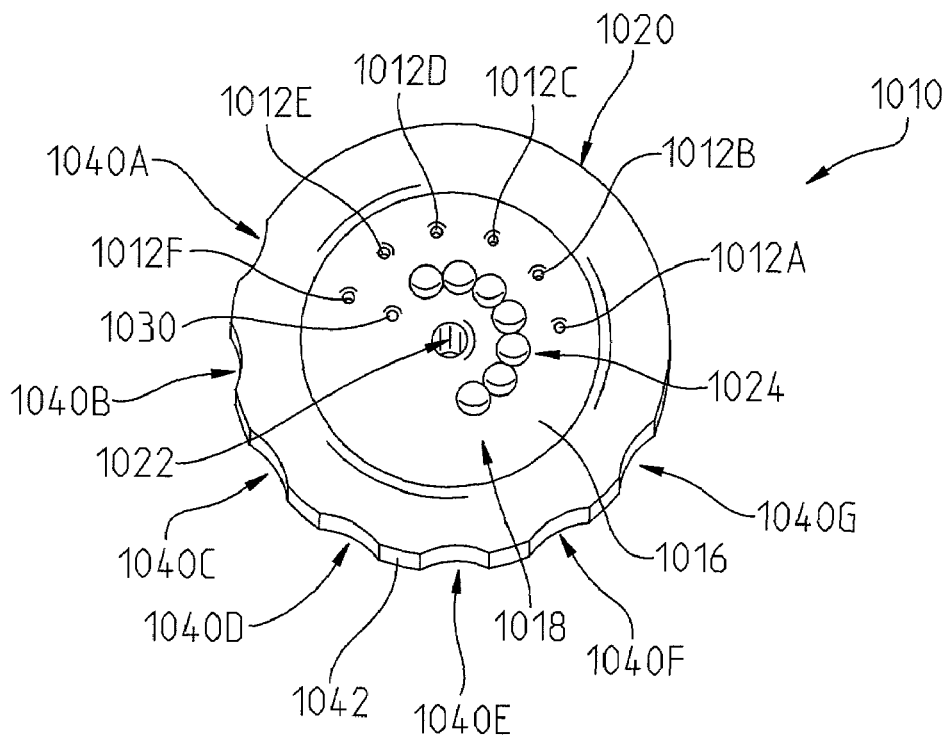
FIG. 40 is a bottom view of the flow selector of FIG. 39.
Figure 41:
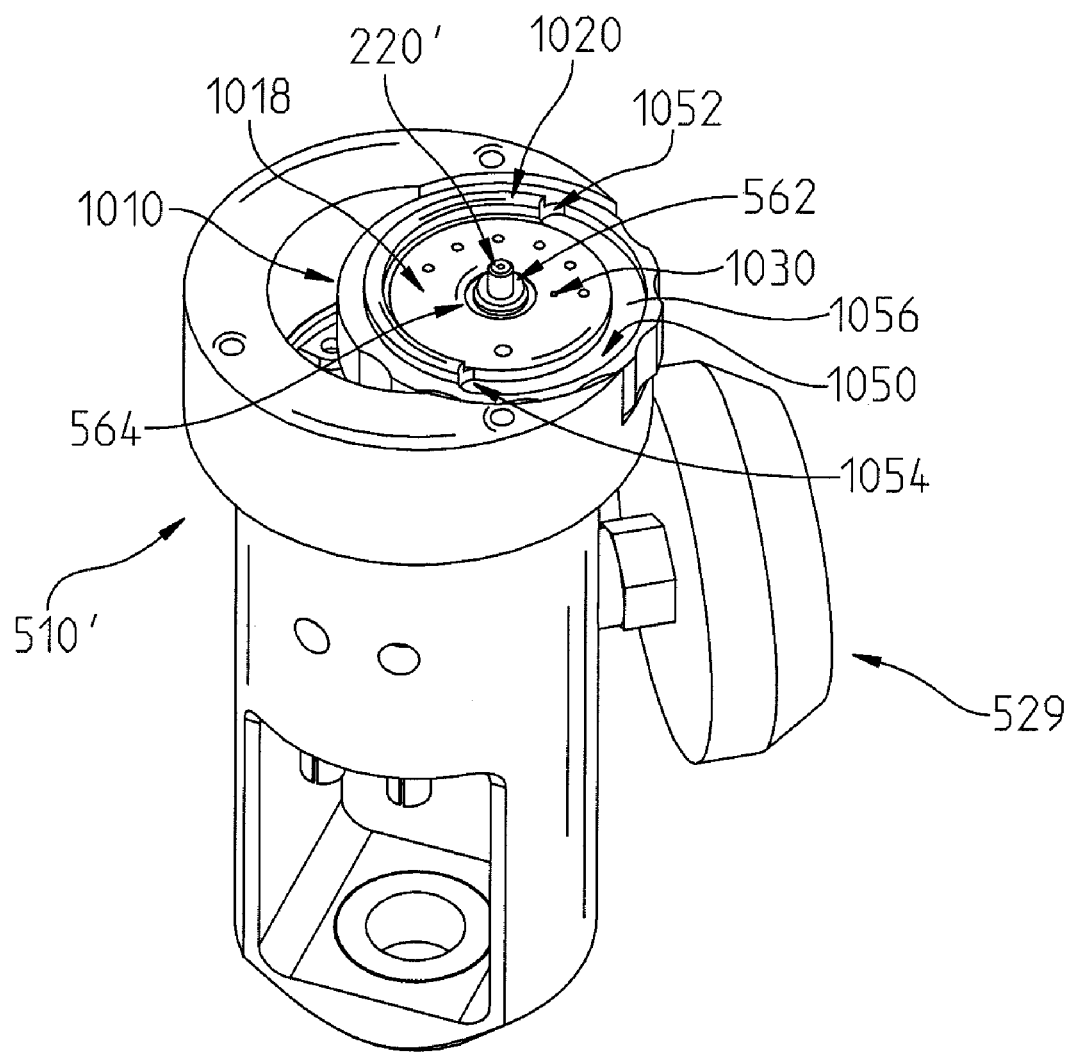
FIG. 41 is the isometric view of FIG. 37 with the flow selector of FIG. 39 assembled thereto.

Referring to FIGS. 39-41, a flow selector 1010 is shown. Flow selector 1010 is generally similar to flow selector 400. Flow selector 1010 includes a plurality of fluid passages 1012A-F each extending from a first side 1014 of flow selector 1010 to a second side 1016 of flow selector 1010. Fluid passages 1012A-F each are configured to pass a predetermined flow rate of fluid. Several methods of configuring fluid passages to pass predetermined flow rate of fluid are described herein and may be used with flow selector 1010. In one embodiment, fluid passages 1012A-F each include an flow calibrator, such as an occluder (not shown), which is introduced from a radial surface (not shown) of an inner component 1018 similar to flow selector 400. Flow selector 1010, like flow selector 400, includes both an inner component 1018 and an outer component or knob 1020.

Flow selector 1010 further includes a central passage 1022 which receives axle 220'. Referring to FIG. 40, second side 1016 of flow selector 1010 includes a plurality of recesses 1024 sized to receive a detent 554 (see FIGS. 19 and 37). Recesses 1024 cooperate with detent 554 to align respective flow passages 1012 in flow selector 1010 with flow passage 547 in pressure reduction section 170 and to provide a positive indication to the user of such alignment. Referring to FIG. 19, detent 554 is a spherical ball which is at least partially received in a recess 556 of housing 178 of pressure reduction section 170. Detent 554 is sized to cooperate with recesses 1024 in flow selection 1010.

Flow selector 1010 further includes a fluid passage 1030 which as explained below is a vent passage which is aligned with a passage 1032 in first body portion 1034 of conserver portion 1036. Referring to FIG. 35, conserver portion 1036 including a first body portion 1034, a second body portion 514' which is generally identical to second body portion 514 of conserver 500, and a third body portion 516" which is generally identical to third body portion 516 of conserver 500. Third body portion 516" differs in the external profile of body portion 516'.

Figure 36:
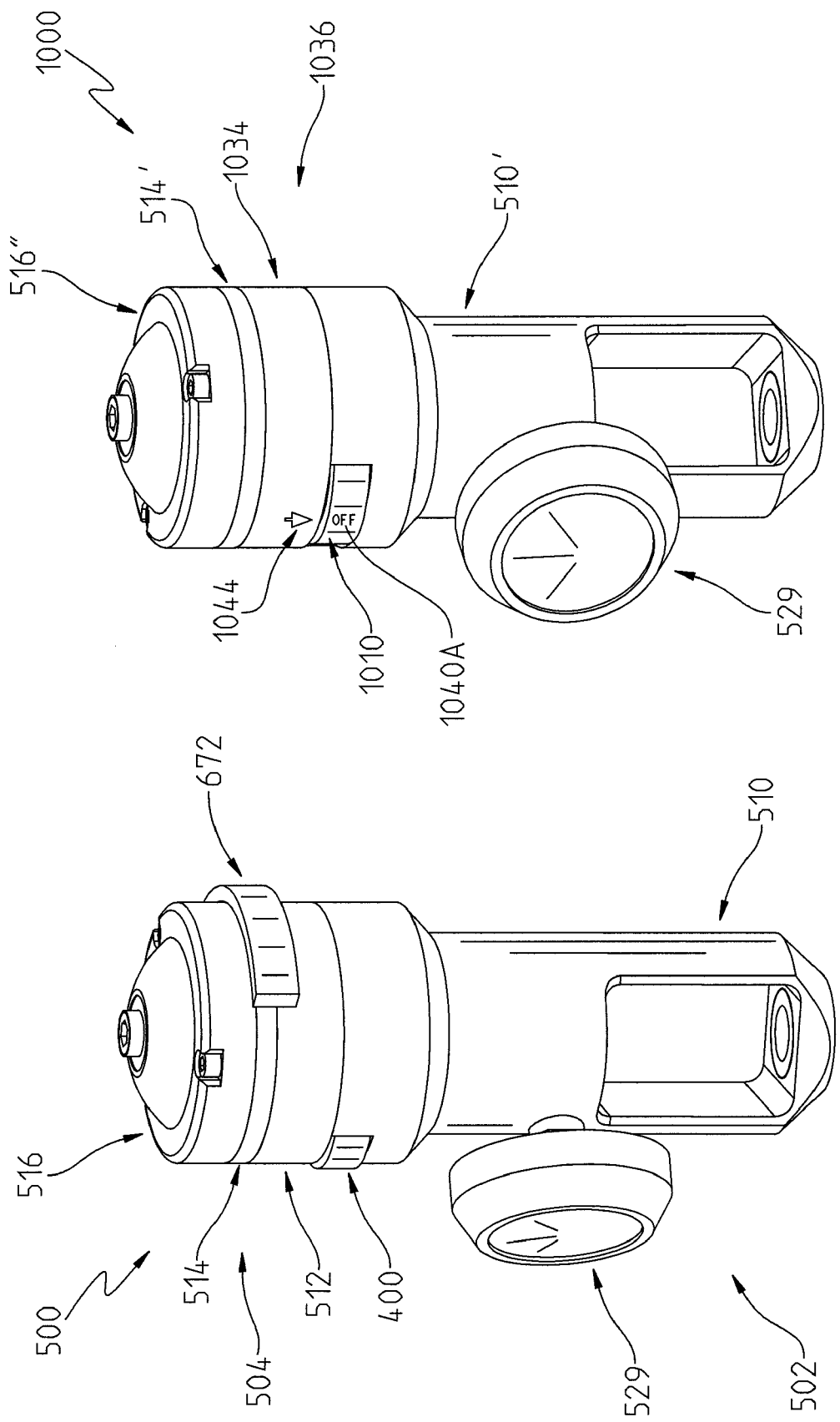
FIG. 36 provides another view of the side-by-side comparison of the conserver of FIG. 10 and a further exemplary conserver.

Returning to FIGS. 39 and 40, outer component 1020 of flow selector 1010 includes a plurality of indicia portions 1040A-G and a knurled outer surface 1042. Knurled outer surface 1042 assists a user in gripping flow selector 1010 to impart a rotation to flow selector 1010. Indicia portions 1040A-G provide a visual indication to the user of which fluid passage 1012 is aligned with fluid passage 547 in pressure reduction section 170 or in the case of indicia portion 1040A (as shown in FIG. 36) that none of fluid passages 1012 are aligned with fluid passage 547 in pressure reduction section 170. Knob 1020 is generally about fifty percent as thick as the knob of flow selector 400.

In the illustrated embodiment, indicia portion 1040A corresponds to an off setting, indicia portion 1040B corresponds to a continuous setting whereby as explained herein fluid is provided to the cannula 503 on a continuous basis, and indicia portions 1040C-G correspond to a plurality of intermittent settings wherein each one provides a predetermined amount of fluid to cannula 503 during an inhalation of the patient.

Referring to FIG. 41, flow selector 1010 is coupled to body portion 510' with retainer 564 coupled to axle 220'. Seal 562 is placed over retainer 564 and axle 220'. Outer component 1020 of flow selector 1010 includes a recess 1050 having a first end 1052 and a second end 1054. Recess 1050 further includes a cam surface 1056 which as explained below positions a valve 1070 which controls the operation of conserver 1000 in either a continuous mode of operation or an intermittent mode of operation.

Figure 42:
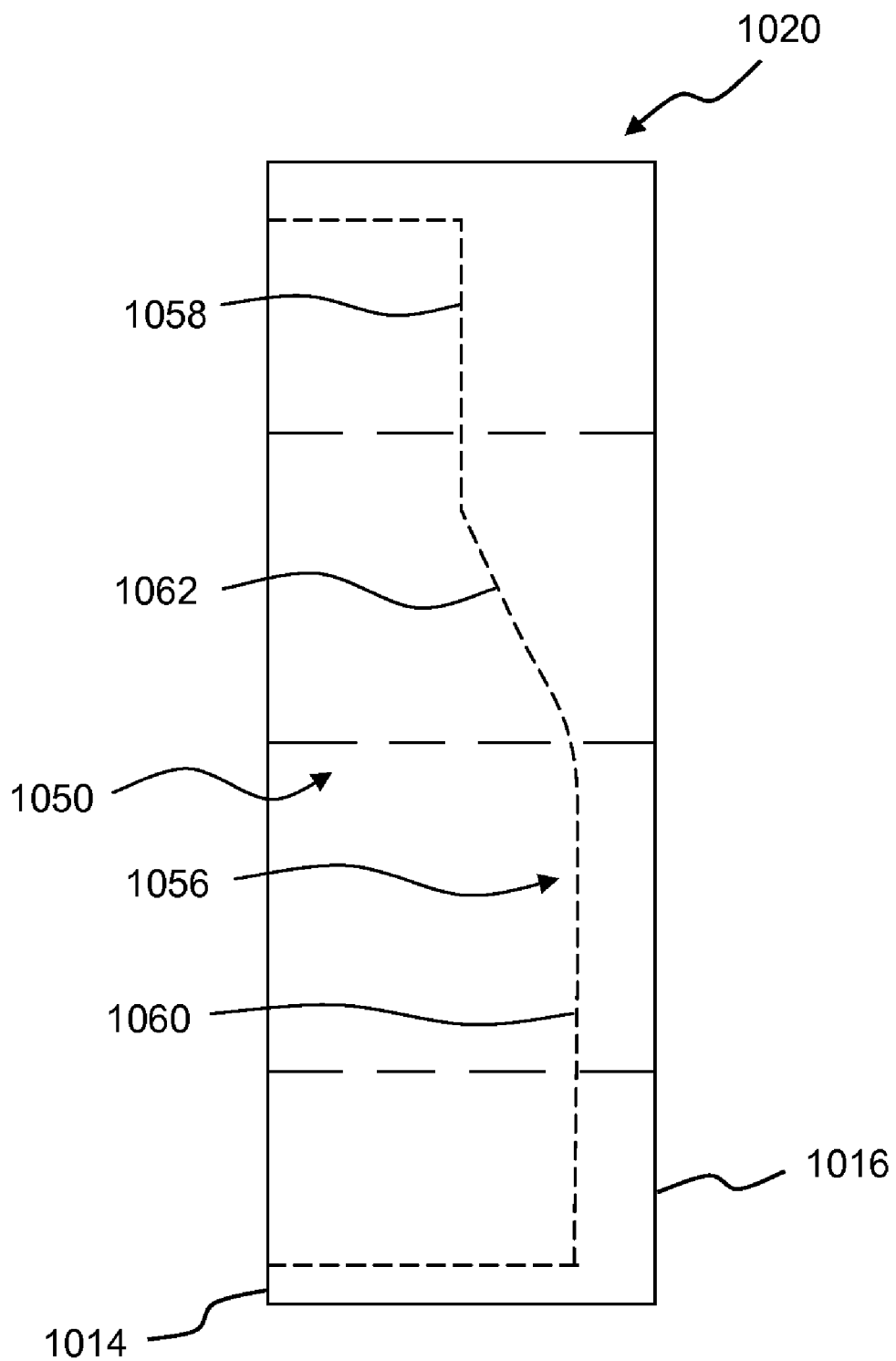
FIG. 42. is a representative view of a cam surface of the flow selector of FIG. 39.

Referring to FIG. 42, cam surface 1056 includes a first elevation 1058 which generally corresponds to a continuous mode of operation a second elevation 1060 which generally corresponds to an intermittent mode of operation and a transitional surface 1062 connecting first elevation 1058 and second elevation 1060. A head portion 1072 (see FIG. 48) of valve 1070 is generally received in recess 1050, rides along cam surface 1056, and interacts with first end 1052 and second end 1054 to limit the rotation of flow selector 1010.

Figure 43A:
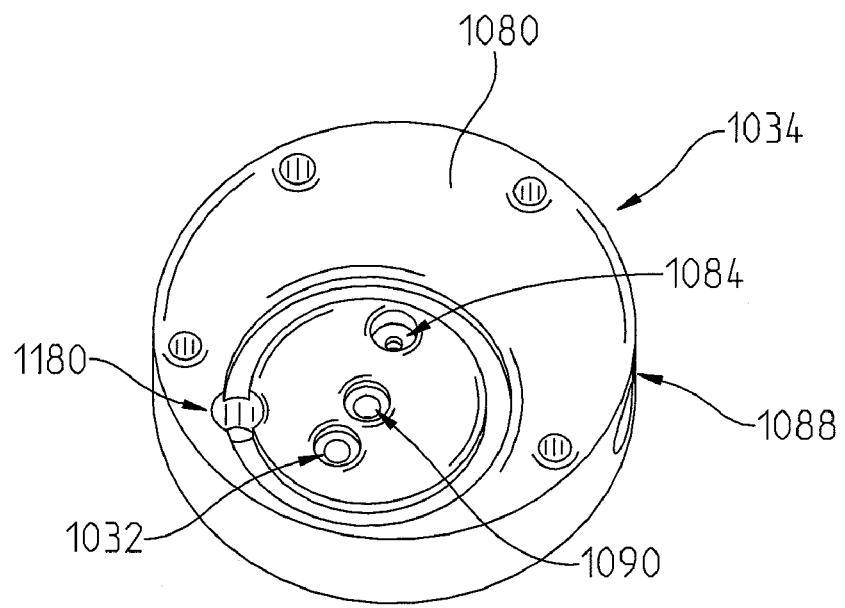
FIG. 43A is an isometric bottom view of a first body portion of the exemplary conserver of FIG. 35.
Figure 43B:
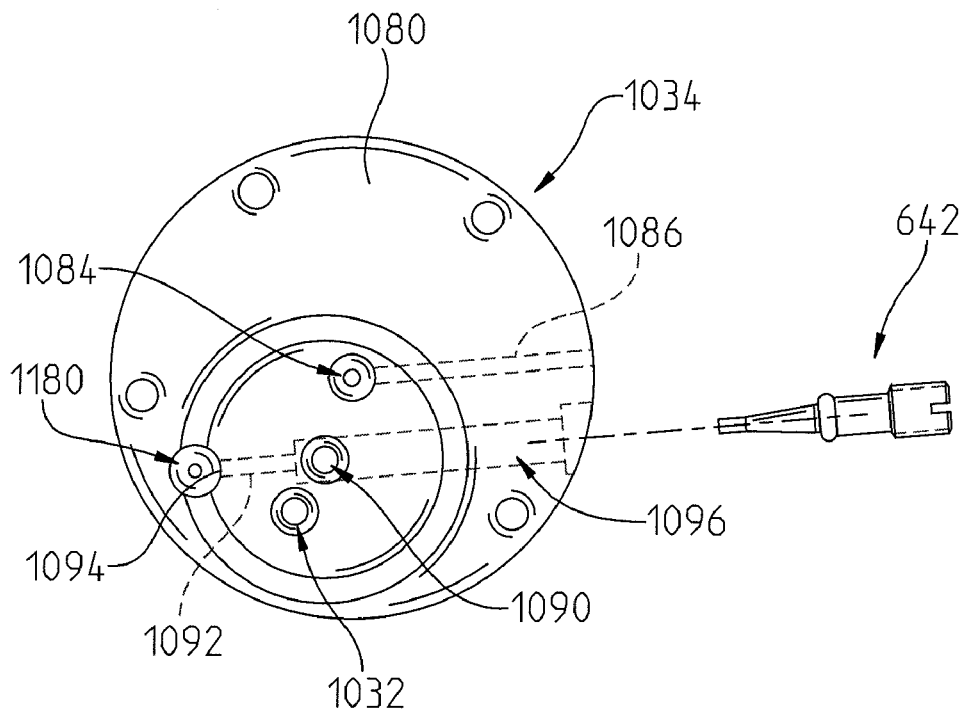
FIG. 43B is a bottom view of the first body portion of FIG. 43A.
Figure 44A:
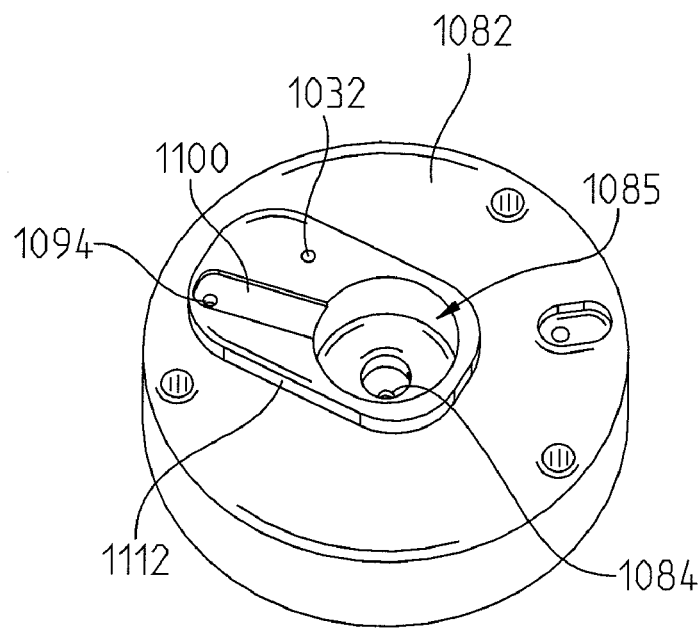
FIG. 44A is an isometric top view of a first body portion of the exemplary conserver of FIG. 35.
Figure 44B:
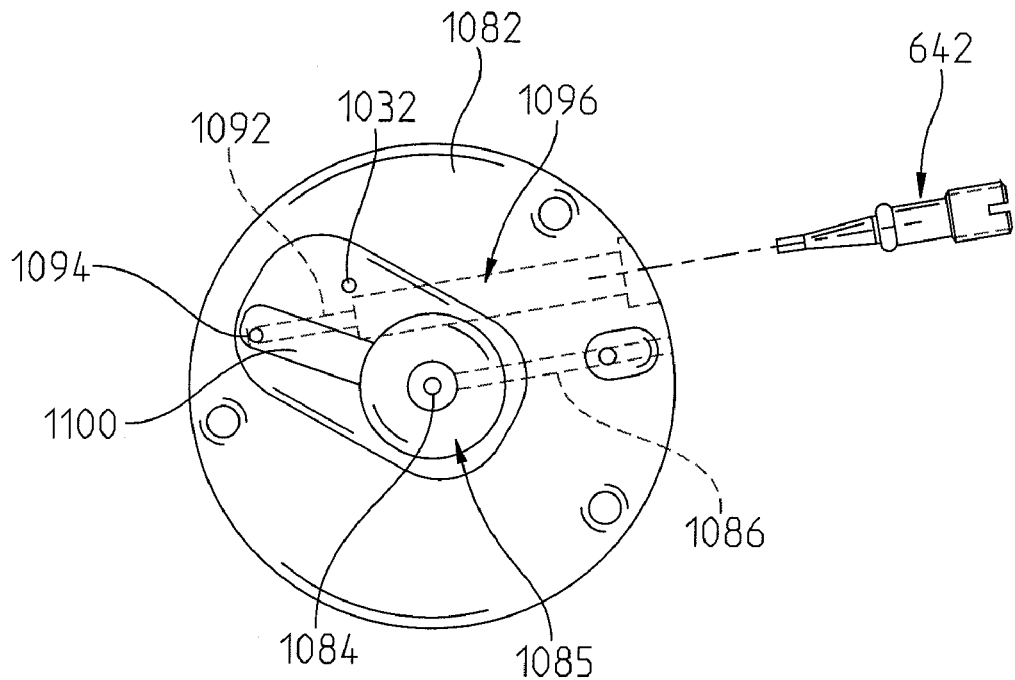
FIG. 44B is a top view of the first body portion of FIG. 44A.

Referring to FIGS. 43A and 43B, a first side 1080 of body portion 1034 is shown. Referring to FIGS. 44A and 44B, a second side 1082 of body portion 1034 is shown. Referring to FIGS. 43A and 43B, first side 1080 includes a fluid passage 1084 which is aligned to be in fluid communication with the selected fluid passage 1012 of flow selector 1010 and with demand piston 734 which is received in a recess 1085 on second side 1082 of body portion 1034 (see FIG. 44A). Similar to fluid passage 588 of conserver 500 which is in fluid communication with fluid passage 602 when demand piston 734 is spaced apart from seal 600 (see FIG. 14A), fluid passage 1084 is in fluid communication with fluid passage 1086 (see FIG. 51) when demand piston 734 is spaced apart from seal 600 (see FIG. 51). Fluid passage 1086 is in fluid communication with cannula 503 through nipple 608.

Body portion 1034 further includes a fluid passage 1090 which is in fluid communication with the fluid passage 221 of axle 220' when body portion 1034 is assembled to body portion 510'. Fluid passage 1090 is in fluid communication with an internal fluid passage 1092 which is in fluid communication with another fluid passage 1094. The rate at which fluid flows from fluid passage 1090 through fluid passage 1092 to fluid passage 1094 is controlled by a position of needle valve 642 which is threadably received in a recess 1096 in body portion 1034. As explained above, by adjusting how far a tip portion 644 of needle valve 642 is advanced into fluid passage 1092 for conserver 1000 or fluid passage 616 of conserver 500, the cross-sectional area of the respective fluid passage 1092 and fluid passage 616 may be adjusted. As such, needle valve 642 may be used to adjust the rate at which fluid passes from fluid passage 1090 to fluid passage 1094.

As explained herein, the cross-sectional area of fluid passage 1092 for conserver 1000 and fluid passage 616 for conserver 500 effects the sensitivity of the respective conserver 1000 and conserver 500. For instance, needle valve 642 may be positioned within fluid passage 616 or fluid passage 1092 to permit about 500 cc/min to about 750 cc/min flow of fluid through fluid passage 616 or fluid passage 1092. At this setting conserver 500 or conserver 1000 will provide multiple pulses of fluid per inhalation by the patient. Conserver 500 or conserver 1000 may be set to provide a single pulse of fluid per breath by positioning needle valve 642 within fluid passage 616 or fluid passage 1092 to permit about 30 cc/min to about 50 cc/min, to about 100 cc/min, to about 150 cc/min, to about 250 cc/min.

As mentioned above in connection with conserver 500, the fluid passing by needle valve 642 accumulates in a cavity 737 on the backside of piston 734. The accumulation of fluid on the backside of piston 734 causes piston 734 to move towards seal 600 against the bias of biasing member 732 resulting eventually in fluid passage 588 no longer being in fluid communication with fluid passage 602. The same effect is created by body portion 1034 and body portion 514'.

Figure 45:
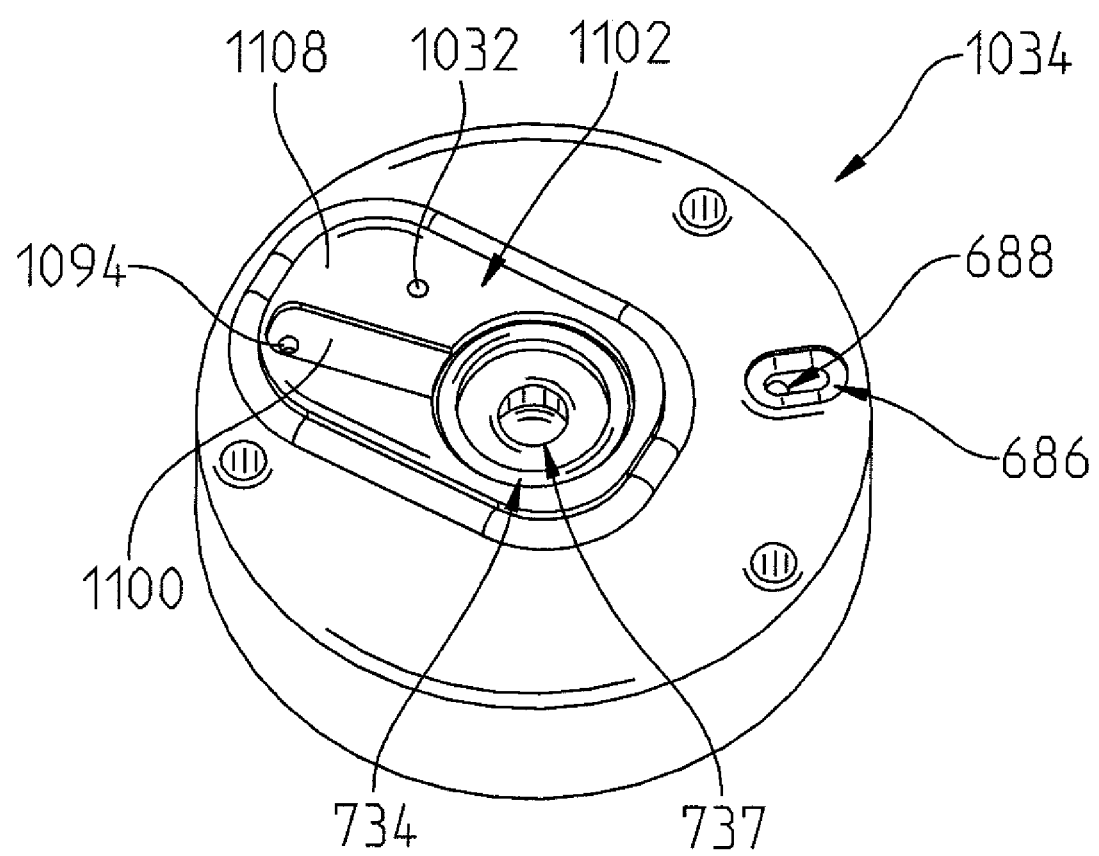
FIG. 45 is an isometric view of the first body portion of FIG. 44A with a demand piston assembled thereto.
Figure 46A:
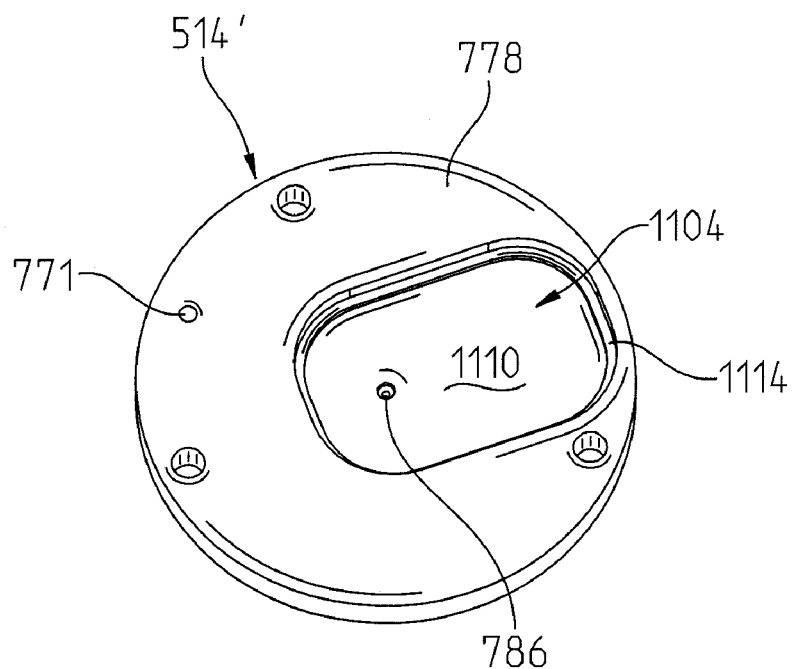
FIG. 46A is an isometric bottom view of a second body portion of the exemplary conserver of FIG. 35.
Figure 46B:
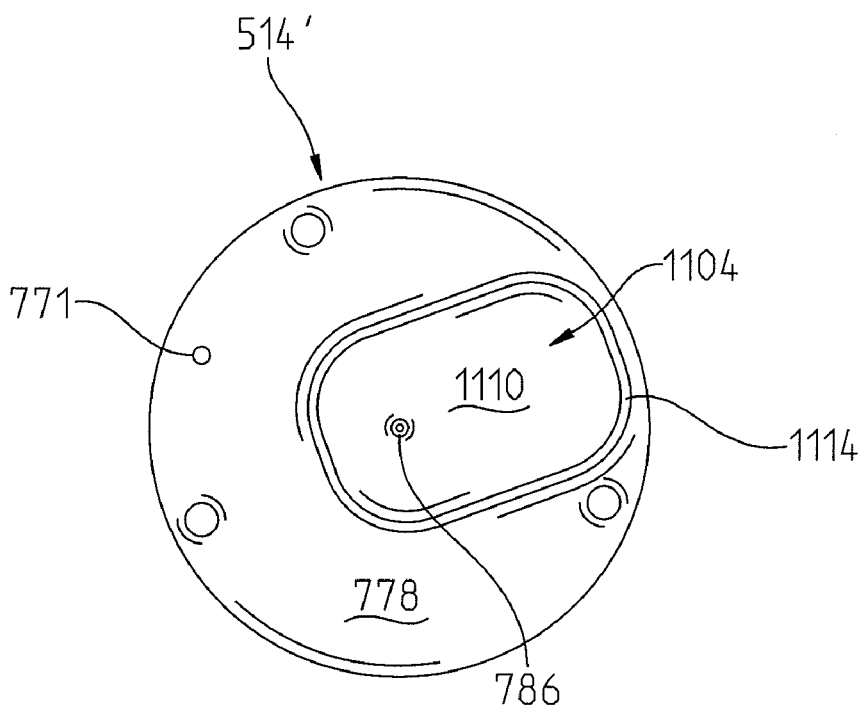
FIG. 46B is a bottom view of the second body portion of FIG. 46A.
Figure 47A:
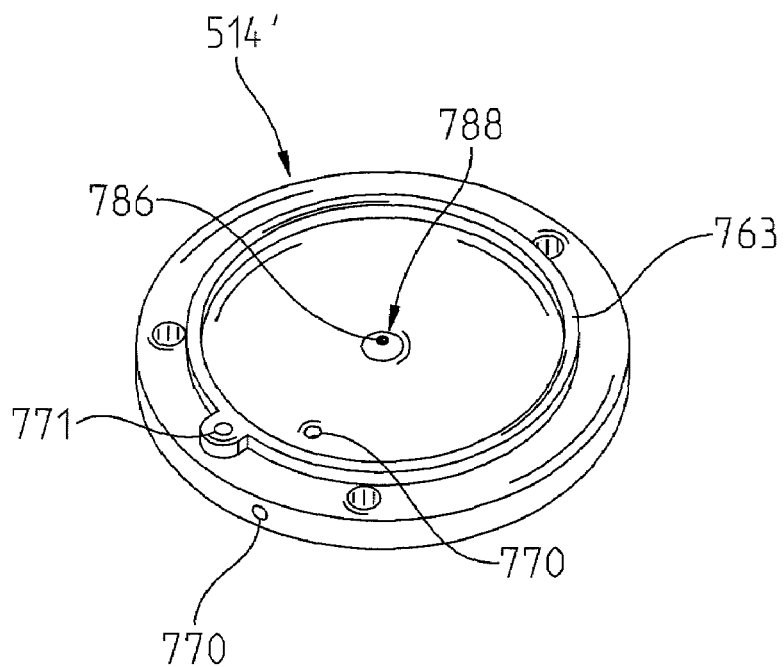
FIG. 47A is an isometric top view of a second body portion of the exemplary conserver of FIG. 35.
Figure 47B:
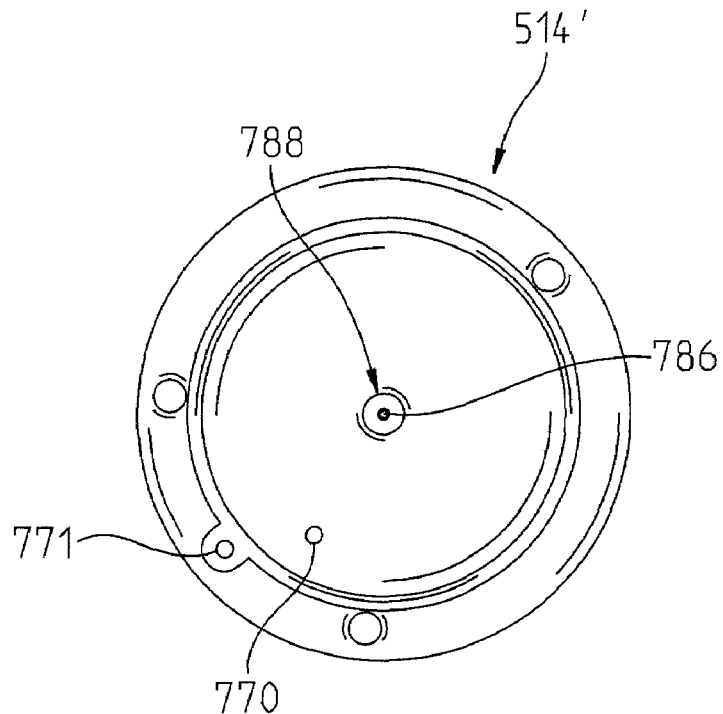
FIG. 47B is a top view of the second body portion of FIG. 43A.
Figure 48:
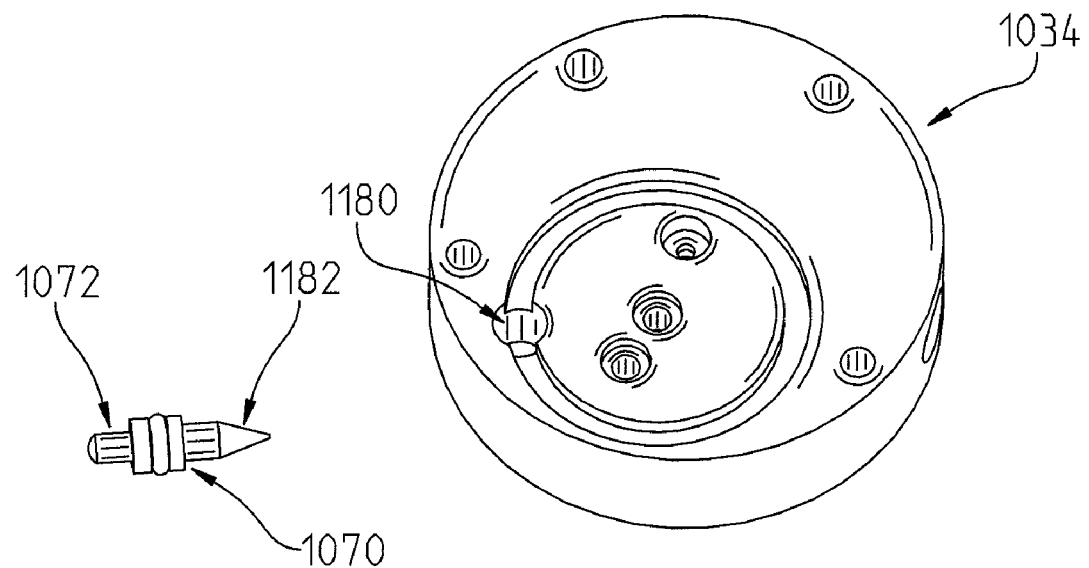
FIG. 48 is an isometric view of the first body portion of FIG. 43A and a valve spaced apart.

Referring to FIG. 45, fluid passage 1094 intersects with a fluid passage or channel 1100 in a protruding portion 1102 of body portion 1034. Protruding portion 1102 is shown as being generally rectangular with rounded corners. However, protruding portion 1102 may be any suitable shape such as circular or oval. Fluid passage 1100 permits fluid to pass from fluid passage 1094 to cavity 737 of piston 734. Protruding portion 1102 of body portion 1034 is received in a recess 1104 of body portion 514' (see FIG. 46A). The only difference between body portion 514 and 514' is the configuration of the recess on the bottom of the body member, recess 780 for body portion 514 and recess 1104 of body portion 514'.

A seal 1106 seals the region between a top surface 1108 of protruding portion 1102 of body portion 1034 and a lower surface 1110 of recess 1104 of body portion 514'. Seal 1106 seals against a side surface 1112 (see FIG. 44A) of protruding portion 1102 and a step surface 1114 of recess 1104. Since the region between a top surface 1108 of protruding portion 1102 and a lower surface 1110 of recess 1104 is sealed any fluid exiting fluid passage 1094 accumulates in cavity 737 of piston 734 and moves piston 734 against the bias of biasing member 732.

As explained above in connection with conserver 500, fluid pressure from the backside of piston 734 may be vented to atmosphere through fluid passage 771 when an inhalation is detected by conserver 500. Conserver 1000 detects an inhalation and vents the backside of piston 734 in the same manner as conserver 500. When the patient inhales, the pressure in cannula 503 is reduced. The reduction in pressure in cannula 503 is communicated to a cavity 775 formed by third body portion 516" and diaphragm 794 through the connection of fluid passages 690 (in first body portion 1034, see FIG. 51), 688 (in first body portion 1034, see FIG. 51), 771 (in second body portion 514'), 773 (in third body portion 516"), and 777 (in third body portion 516") as shown in FIG. 12C.

Similar to conserver 500, conserver 1000 may be used with a dual lumen cannula by replacing third body portion 516" with third body portion 516'. In the dual lumen configuration the reduction in pressure in the cannula is communicated to cavity 775 through the second lumen attached to nipple 779.

As explained above in connection with conserver 500, when conserver 500 is to be operated in a continuous mode of operation it is not desired to provide fluid to backside 735 of piston 734 in order that piston 734 remains spaced apart from seal 600. In conserver 500 this is accomplished by rotating selector 672 which rotates selector 670 such that fluid is no longer communicated to backside 735 of piston 734 through fluid passage 760 in selector 670. In conserver 1000, when a continuous flow setting is selected with flow selector 1010, valve head 1072 rides up cam surface 1056 to elevation 1058 thereby advancing valve 1070 further into a recess 1180 in body portion 1034 in direction 1186.

Figure 50:
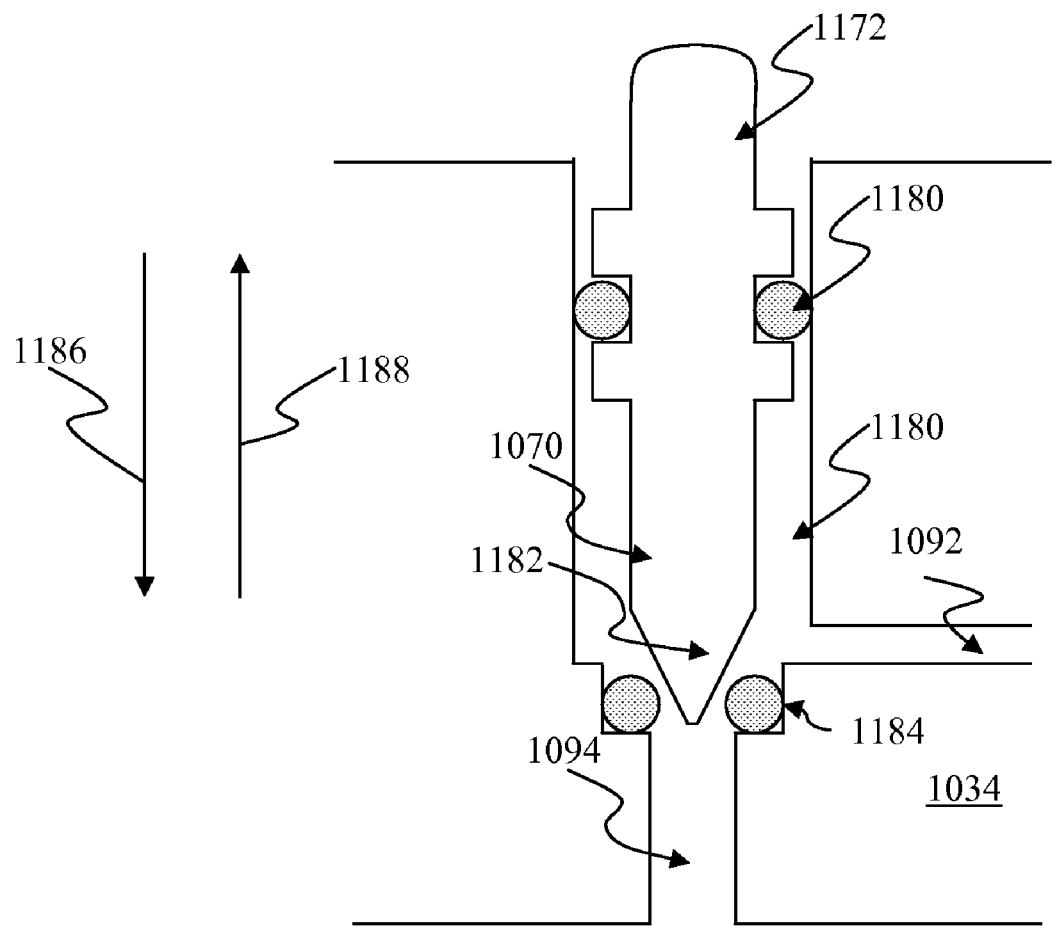
FIG. 50 is a representative cross-section of the assembly of the first body portion and valve of FIG. 49

Referring to FIG. 50, recess 1180 intersects with fluid passage 1092 and fluid passage 1094. When fully seated in recess 1180, a tip portion 1182 of valve 1070 seals against a seal 1184 which prevents fluid from passing from fluid passage 1092 to fluid passage 1094. Valve 1070 is fully seated when valve head 1072 is at elevation 1058 of cam surface 1056.

When flow selector 1034 rotates to an intermittent mode of operation valve head 1072 may move in direction 1188 to elevation 1060 of cam surface 1056. In one embodiment, valve 1070 is biased in direction 1188 with a spring. In the illustrated embodiment, valve 1070 is biased in direction 1188 due to the fluid pressure in fluid passage 1092. As such, the fluid pressure of the fluid in fluid passage 1092 moves valve 1070 in direction 1188 and converts conserver 1000 from a continuous mode of operation to an intermittent mode of operation because fluid will pass through fluid passage 1094 to backside 735 of piston 734.

Body portion 1034 includes a vent passage 1032 which assists in converting conserver 1000 from an intermittent mode of operation to a continuous mode of operation. In the intermittent mode of operation, conserver 1000 provides fluid to cannula 503 in response to the detection of an inhalation of the patient. As such, when the patient is not inhaling conserver 1000 is not providing fluid to the patient through cannula 503. In such a situation, piston 734 is in contact with seal 600 preventing the flow of fluid to cannula 503.

Assuming the user switches to a continuous mode of operation, valve 1070 moves in direction 1186 into contact with seal 1184 and additional fluid is prevented from reaching backside 735 of piston 734. However, backside 735 of piston 734 already includes enough fluid to cause piston 734 to be in contact with seal 600. As such, the continuous flow of fluid would not start until the next inhalation of the patient which as described above with reference to conserver 500 will move diaphragm 794 thereby venting the fluid from backside 735 of piston 734 to atmosphere through fluid passage 770. This delay may be uncomfortable for the patient. As such, when flow selector 1010 is rotated to a continuous flow setting, vent passage 1032 is aligned with fluid passage 1030 in flow selector 1010. This alignment permits fluid to be communicated from the backside 735 of piston 734 (generally between surface 1108 of body portion 1034 and surface 1110 if body portion 514') through flow selector 1010 to an unsealed region adjacent first side 1014 of flow selector 1010, thereby venting the fluid from backside 735 of piston 734.

Figure 49:
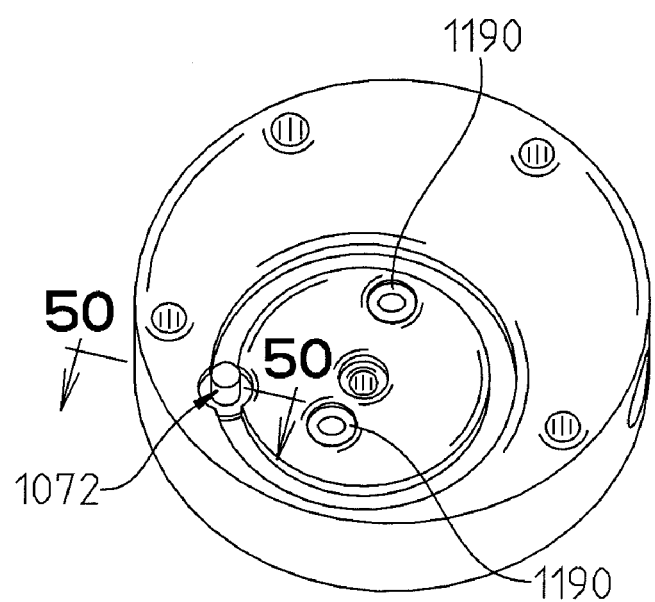
FIG. 49 is an isometric view of the first body portion of FIG. 43A with the valve of FIG. 48 assembled thereto.

As shown in FIG. 49, a seal 1190 prevents fluid from vent passage 1032 from being vented unless vent passage 1032 is aligned with passage 1030 in flow selector 1010.

Referring to FIG. 51, an exemplary cross sectional view of conserver 1000 is shown. It should be noted that FIG. 51 is provided to better illustrate the operation of conserver 1000 and that FIG. 51 is not intended to be a single cross-section through conserver 1000 but rather to illustrate various features of the various components of conserver 1000. Thirty-seven components are call out in FIG. 51 and are listed in the table below.

| Number on FIG. 51 | Component |
|---|---|
| 1 | Filters 362 |
| 2 | Filter inlet retainer 364 |
| 3 | Seal ring 366 |
| 4 | Seal 396 |
| 5 | Seal 263 |
| 6 | Seal 542 |
| 7 | Vent mechanism 172 |
| 8 | Biasing member 174 |
| 9 | Seal 265 |
| 10 | Piston 176 |
| 11 | Seal 198 |
| 12 | Housing 178 |
| 13 | Seal 259 |
| 14 | Seal 563 |
| 15 | Seal 561 (Seal 560 not illustrated) |
| 16 | Occluder 448 |
| 17 | Body portion 510' |
| 18 | Inner component 1018 of flow selector 1010 |
| 19 | Outer component 1020 of flow selector 1010 |
| 20 | Axle 220' |
| 21 | Seal 562 |
| 22 | Body portion 1034 |
| 23 | Seal 600 |
| 24 | Seal 1106 |
| 25 | Seal on demand piston 734 |
| 26 | Biasing member 732 |
| 27 | Demand piston 734 |
| 28 | Biasing member 828 |
| 29 | Seal between adjuster 820 and body portion 516" |
| 30 | Adjuster 820 |
| 31 | Body portion 516" |
| 32 | Diaphragm 794 |
| 33 | Body portion 514' |
| 34 | Seal 686 |
| 35 | Seal between body portion 1034 and nipple 608 |
| 36 | Nipple 608 |
| 37 | Fluid pressure gauge 529 |

Figure 52:
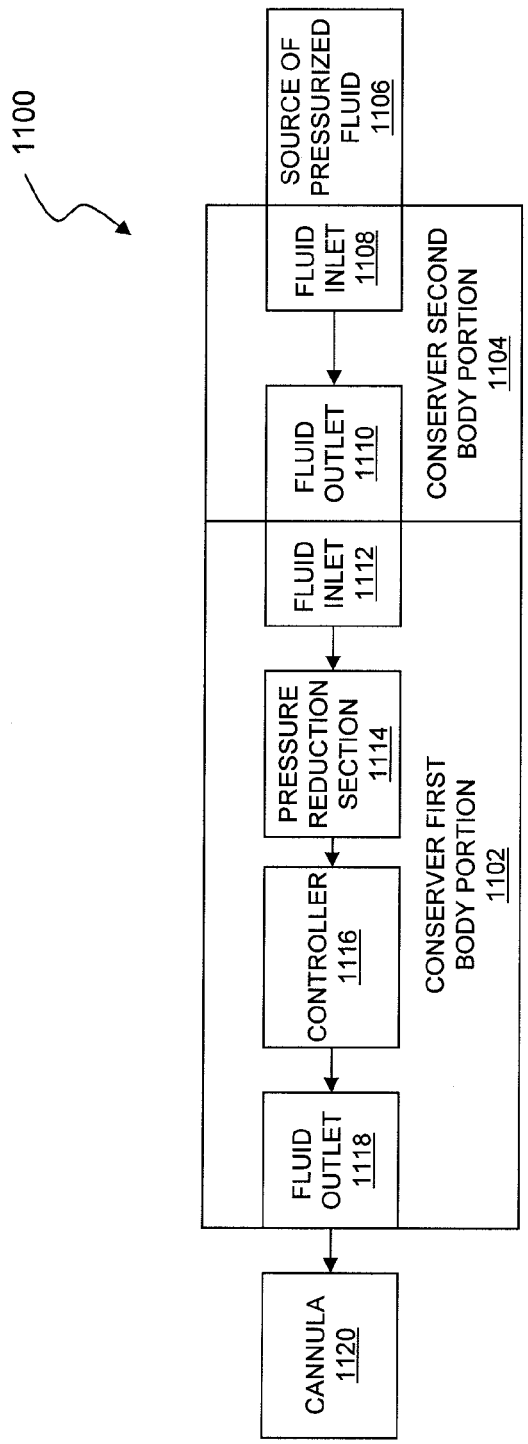
FIG. 52 is diagrammatic representation of yet a further exemplary conserver.

Referring to FIG. 52, a diagrammatic representation of a conserver 1100 is shown. Conserver 1100 includes a first conserver body portion 1102 and a second conserver body portion 1104. Second conserver body portion is coupled to first conserver body portion 1102 and to a source of pressurized fluid 1106. An exemplary source of pressurized fluid is a portable oxygen storage tank.

Fluid flows from the source of pressurized fluid 1106 into a fluid inlet 1108 of second conserver body portion 1104 to a fluid outlet 1110 of second conserver body portion 1104. The fluid then enters a fluid inlet 1112 of first conserver body portion 1102 where it is passed through a pressure reduction section 1114. The fluid then passes onto a controller 1116 which controls the provision of the fluid to a fluid outlet 1118 to which a cannula 1120 is attached. In one embodiment, controller 1116 is a pneumatic controller. Exemplary pneumatic controllers are described herein. In one embodiment, controller 1116 is an electronic controller. Exemplary electronic controllers are provided in U.S. Provisional Patent Application Ser. No. 60/783,243, filed Mar. 17, 2006, titled "ELECTRONIC CONSERVER."

First conserver body portion 1102 and second conserver body portion 1104 are made of dissimilar materials. First conserver body portion 1102 is made from a first material which is receptive to being etched and anodized. Exemplary first materials include aluminum (including aluminum alloys), composite, and polymeric materials, such as plastics. First conserver body portion 1102 may be a multi-piece assembly, such conserver 1000 described herein.

Second conserver body portion is made from a second material. Exemplary second materials include brass (including brass alloys), copper (including copper alloys), and titanium (including titanium alloys).

As shown in FIG. 51, first conserver body portion 1102 houses pressure reduction section 1114 and controller 1116. Exemplary pressure reduction sections are disclosed herein.

Figure 53:
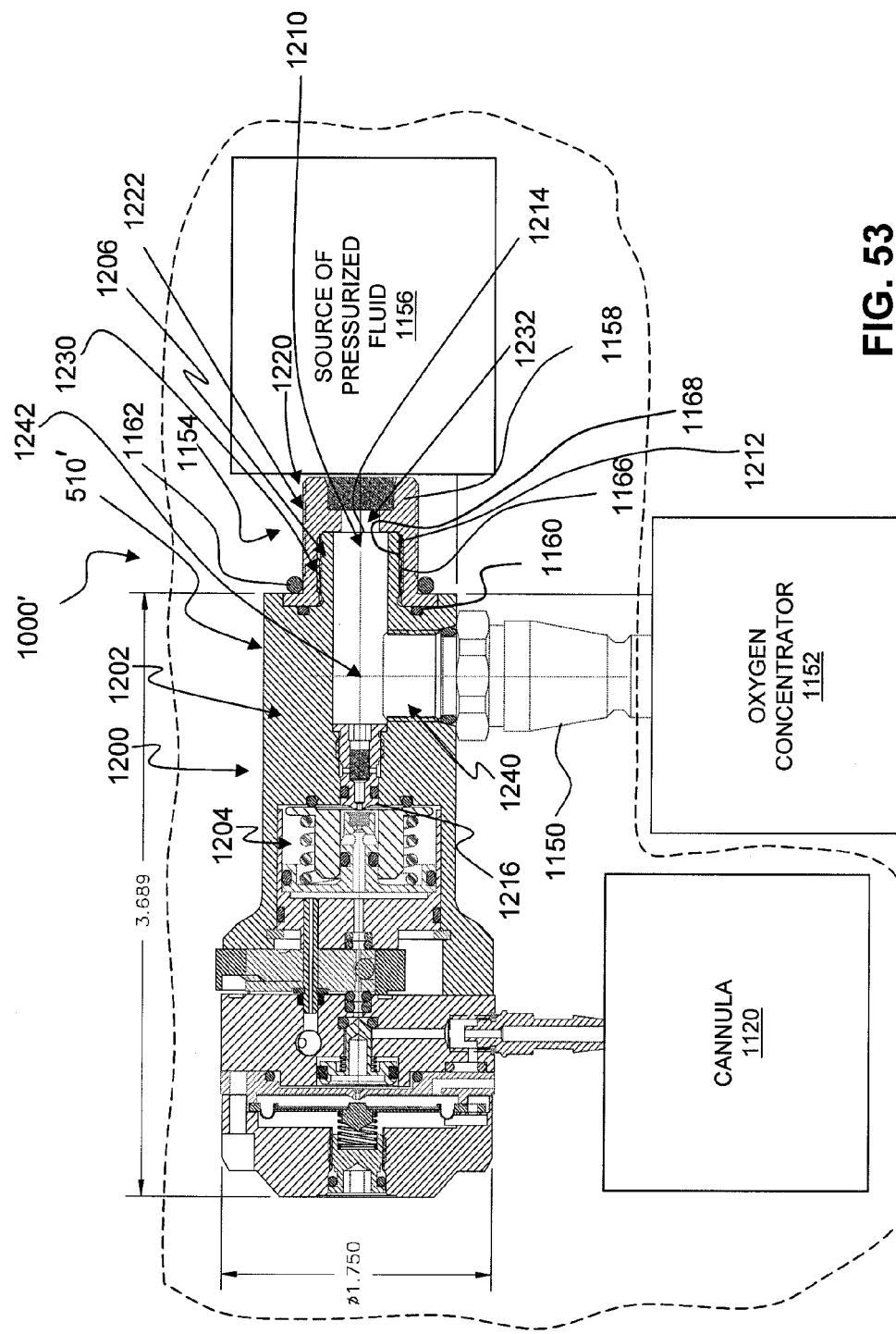
FIG. 53 is a sectional representation of the conserver of FIG. 35 modified in accordance with the exemplary conserver of FIG. 52.
Figure 55:
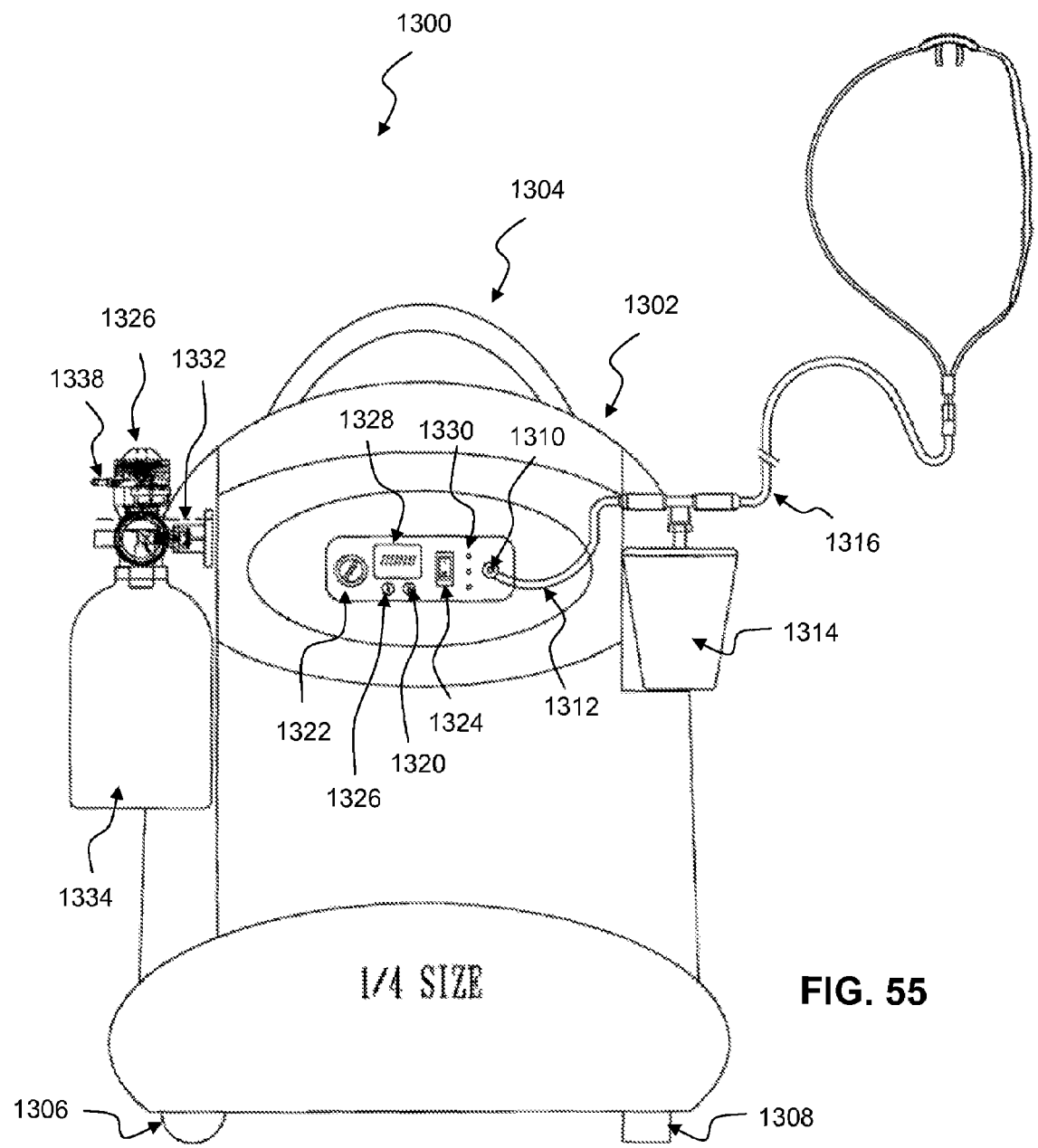
FIG. 55 is a front view of an exemplary home fill system.

Referring to FIG. 53, converser 1000' is shown modified to including a quick connect fitting 1150 for attaching conserver 1000' to an oxygen concentrator 1152 and yoke 520 is replaced by a coupler 1154 which is coupled to the remainder of body 510' and to a source of pressurized fluid 1156.

In one embodiment, body 510' corresponds to first conserver body portion 1102 of conserver 1100 and coupler 1154 corresponds to second conserver body portion 1104. In one embodiment, body portion 510' is made from a first material which is receptive to being etched and anodized. Exemplary first materials include aluminum (including aluminum alloys), composite, and polymeric materials, such as plastics. Exemplary locations for etching are provided in FIGS. 17A-D. Coupler 1154 is made from a second material. Exemplary second materials include brass (including brass alloys), copper (including copper alloys), and titanium (including titanium alloys).

A first seal 1160 is interposed between body portion 510' and coupler 1154 to prevent fluid from leaking between the two. A second seal 1162 is placed over an outside surface of coupler 1154. Second seal 1162 compresses against a seat surface of the source of pressurized fluid 1156 to prevent fluid from leaking between the source of pressurized fluid 1156 and the coupler 1154. An external surface 1158 of coupler 1154 is threaded. This threaded surface 1158 mates with a threaded surface on the source pressurized fluid 1156 to coupled coupler 1154 to the source of pressurized fluid 1156. Likewise an internal surface 1166 of coupler 1154 is threaded. This threaded surface 1166 mates with a threaded surface 1168 of body 510' to couple coupler 1154 to body 510'. In one embodiment, the body portion 510' is an apparatus for housing a pressure reduction section and for placing the pressure reduction section in fluid communication with a first source of pressurized fluid and a second source of pressurized fluid. Referring to FIG. 53, the apparatus comprising a unitary body member 1200 having a first portion 1202 with a first recess 1204 sized to receive the pressure reduction section and a second portion 1206 extending from the first portion 1202. The second portion 1206 including first threaded surface 1168. The unitary body member 1200 having a first fluid conduit 1210 which is in fluid communication with an exterior 1212 of the second portion 1206 of the unitary body member 1200 at a fluid inlet 1214 and with the first recess 1204 in the first portion 1202 of the unitary body member 1200 at a fluid outlet 1216. The apparatus further comprising a first coupler 1154 having a cylindrical body 1220 with a second threaded surface 1158 on an exterior 1222 of the cylindrical body 1220 of the first coupler 1154 and a third threaded surface 1166 provided in a second recess 1230 of the first coupler. The third threaded surface 1166 cooperating with the first threaded surface 1168 of the second portion 1206 of the unitary body member 1200 to couple the first coupler 1154 to the unitary body member 1200. The first coupler having a second fluid conduit 1232 which is in fluid communication with the first fluid conduit 1210 of the second portion 1206 of the unitary body member 1200 when the first coupler 1154 is coupled to the unitary body member 1200. The first source of pressurized fluid 1156 is coupled to the first coupler through the second threaded surface 1158 on the exterior 1222 of the cylindrical body 1220. The apparatus further comprising a second coupler 1150 coupled to the first portion 1202 of the unitary body member 1200 and in fluid communication with a third fluid conduit 1240 of the unitary body member 1200. The third fluid conduit 1240 of the unitary body member 1200 being in fluid communication with the first fluid conduit 1210 of the unitary body member 1200 at a first location 1242 which is prior to fluid outlet 1216 of the first fluid conduit 1210. The second source of pressurized fluid is coupled to the second coupler 1150.

As stated above conserver 1100' is in fluid communication with an oxygen concentrator 1152 through a quick connect fitting 1150. Conserver 1000' may be decoupled from the oxygen concentrator 1152 and carried off as a portable unit 1170 along with the source of pressurized fluid 1156 and cannula 1120. Although, not discussed above, cannula 1120 may be a dual lumen cannula, such as to interface with conservers disclosed herein for use with a dual lumen cannula.

In operation, fluid flows from oxygen concentrator 1152 through quick connect fitting 1150 and into conserver body 510' of conserver 1000'. In one embodiment, a portion of the fluid is made available to the patient through the operation of conserver 1000' at the selected setting and the remainder of the fluid passes through coupler 1154 and into the source for pressurized fluid 1156. In one embodiment, the conserver is turned to an "off" setting such that fluid is not provided to the cannula, but rather all fluid is provided to the source for pressurized fluid.

Figure 18:
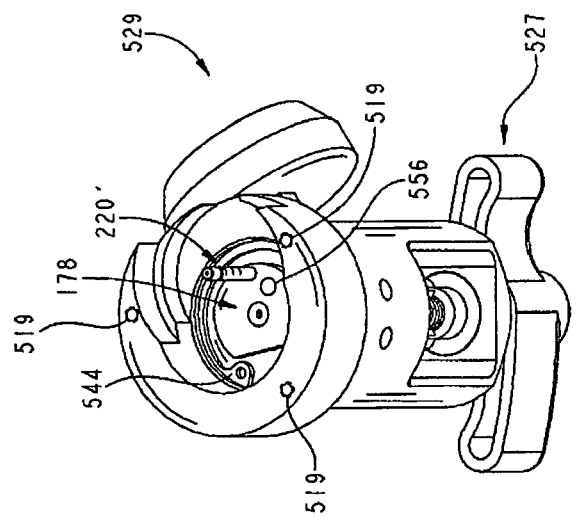
FIG. 18 is an isometric view of the pressure reduction section of FIG. 16 assembled to the body portion of the flow regulator.
Figure 54:
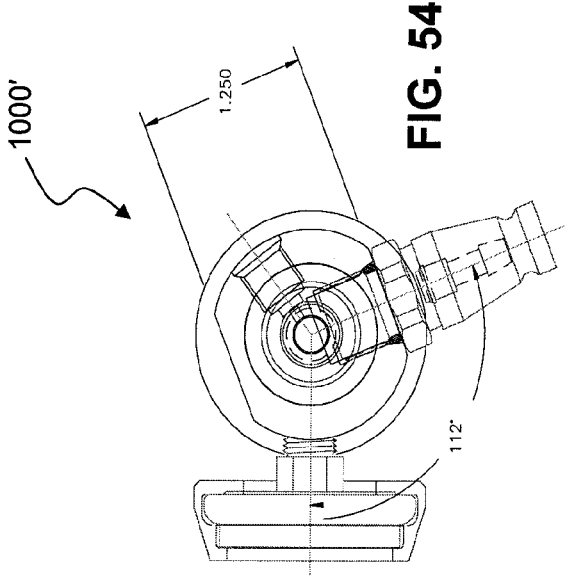
FIG. 54 is a top view of the conserver of FIG. 53.

Referring to FIG. 54, an exemplary embodiment of an oxygen concentrator and storage system 1300 is provided in FIG. 18. System 1300 includes a housing 1302 which houses an oxygen concentrator, a low pressure compressor, a motor, a clutch, and a multi-stage compressor. Housing 1302 includes a handle 1304 which may be gripped by a user to aid in transporting system 1300. Casters 1306 are provided on at least a first end of housing 1300 to aid in rolling system 1300. Also, provided are supports 1308 on a second end to further support housing 1302. Additional details regarding system 1300 are provided in U.S. Provisional Patent Application Ser. No. 60/784,216, filed Mar. 20, 2006, titled "MULTI-STAGE COMPRESSOR AND OXYGEN CONCENTRATOR."

A fluid outlet 1310 from oxygen concentrator is in fluid communication with a first fluid conduit 1312. First fluid conduit 1312 is in fluid communication with a humidifier device 1314. Humidifier device 1314 is in fluid communication with a nasal cannula 1316 which is worn by the patient.

An interface 1320 is shown including a plurality of user inputs. A first user input 1322 is a flow selector which adjusts the fluid flow rate of fluid to the patient through cannula 1316. In one embodiment, flow selector 1322 is coupled to a mechanical flow selector having a plurality of fluid passages each sized to pass a specified fluid flow rate. An exemplary mechanical flow selector is provided in U.S. patent application Ser. No. 11/069,084, filed Feb. 28, 2005, and published as U.S. Published Patent Application 2005/0192538A1, the disclosure of which is expressly incorporated by reference herein. In another embodiment, flow selector 1322 is coupled to a controller (not shown) which electronically actuates a flow selector to adjust the fluid flow to the patient. In one embodiment, the patient may select a flow setting of up to about 5 L/min.

A second exemplary user input 1324 is a power switch which may be actuated to provide power to initiate system 1300 in one of the three discussed modes of operation or to cease operation of system 1300 in one of the three discussed modes of operation. A third exemplary user input 1326 is shown as an up-arrow and a down-arrow. User input 1326 may be used to adjust a value of a parameter displayed on display 1328 and/or may be used to select one or more menu options on display 1328.

Interface 1320 includes a plurality of indicator lights 1330, such as light-emitting diodes, which provide various indications to the user, such as proper operation.

System 1300 further includes a second fluid outlet 1332 which is in fluid communication with a storage tank 1334. In one embodiment, storage tank 1334 is a removable storage tank. In another embodiment, storage tank 1334 is a non-removable storage tank. Storage tank 1334 is shown having a conserver 1336 coupled to a fluid conduit of storage tank 1334. Conserver 1336 includes a flow selector and provides fluid to the user through a cannula coupled to an output 1338 in either a continuous mode of operation or an intermittent mode of operation.

In one embodiment, conserver 1336 couples fluid outlet 3132 to storage tank 1334. In another embodiment, storage tank 1334 includes two fluid connections, one coupled to conserver 1336 and one coupled to fluid outlet 1332.

Conservers 1100 and 1000' are types of exemplary conservers 1336. Another exemplary conserver is provided in U.S. patent application Ser. No. 60/783,243, filed Mar. 17, 2005, titled "ELECTRONIC CONSERVER", the disclosure of which is expressly incorporated by reference herein.

In one embodiment, system 1300 includes a pressure sensor to monitor the pressure of the fluid in storage tank 1334. This information may be communicated to the user through display 1328. In one embodiment, system 1300 includes a calculator, such as in software executed by the controller, which based on the fluid pressure in tank 1334, the size of tank 1334, and the flow setting selected with conserver 1336 calculates one of the distance a user may travel with portable storage tank 1334 or the time period that the user may use storage tank 1334 until the fluid is exhausted. Further, display 1328 may show a percentage indication of the tank 1334 fill process. In one embodiment, a bar graph illustrates the filling progress.

In one embodiment, display 1328 displays a pressure value of storage tank 1334 when filling storage tank 1334 and flow rate or flow setting when not filling storage tank 1334. In one embodiment, system 1300 includes a click style flow control with an electronic interface 1320.

Although the invention has been described in detail with reference to certain preferred embodiments, variations and modifications exist within the spirit and scope of the invention as described and defined in the following claims.

The invention claimed is:

1. A conserver which receives a fluid from a source of pressurized fluid and provides fluid to a patient through a single lumen cannula, the conserver comprising:

a body including at least three body members stacked along a first direction, the body having a fluid input in a first body member, a fluid output in a side of a second body member providing a single fluid connection between the body and the single lumen cannula, wherein the single fluid connection is the only fluid connection between the body and the single lumen cannula, and a fluid passage configured to connect the fluid input to the fluid output;

a pressure reduction section disposed within the first body member of the body and in fluid communication with the fluid passage, the pressure reduction section receiving fluid from the fluid inlet of the body at a first pressure and providing fluid to a portion of the fluid passage positioned downstream of the pressure reduction section;

at least one user input supported by the body;

a pneumatic controller positioned downstream of the pressure reduction section in at least one of the at least three body members other than the first body member, the pneumatic controller having a first configuration to provide a continuous flow of fluid to the fluid outlet of the body in a continuous mode and a second configuration to provide an intermittent flow of fluid to the fluid outlet of the body in an intermittent mode, the intermittent mode and the continuous mode being selectable by the at least one user input, the pneumatic controller includes a sense diaphragm which in the intermittent mode moves along the first direction relative to a diaphragm seat between a closed position and an open position to control the provision of fluid to the single lumen cannula; and a coupler coupled to the first body member of the body, the coupler having a fluid conduit in fluid communication with the fluid inlet of the body, the coupler being adapted to couple to a source of pressurized fluid, wherein the coupler is made from a first material selected from the group of a brass based material, a copper based material, and a titanium based material and the body is made from a second material selected from the group of an aluminum based material, a composite based material, and a polymeric based material.

2. The conserver of claim 1, wherein the at least one user input includes a flow selector having at least a first fluid passage and a second fluid passage, each of the first fluid passage and the second fluid passage being selectably positionable in the fluid passage of the body between the input and the output and configured to communicate fluid to the output when positioned in the fluid passage of the body, wherein the pneumatic controller is in the continuous mode of operation based on the first fluid passage of the flow selector being positioned in the fluid passage of the body and the pneumatic controller is in the intermittent mode of operation based on the second fluid passage of the flow selector being positioned in the fluid passage of the body.

3. The conserver of claim 2, wherein the body includes a vent passage and the flow selector includes a third fluid passage, the third fluid passage being in fluid communication with the vent passage of the body when only one of the first fluid passage of the flow selector and the second fluid passage of the flow selector is positioned in the fluid passage of the body, the one being the first fluid passage of the flow selector.

4. The conserver of claim 2, wherein the flow selector is rotatably coupled to the body and the first fluid passage and the second fluid passage are positionable in the fluid passage of the body through the rotation of the flow selector relative to the body.

5. The conserver of claim 1, wherein a first cavity of one of the body members is in fluid communication with the sense diaphragm and the fluid outlet coupled to the single lumen cannula such that a drop in pressure in the single lumen cannula results in the sense diaphragm moving along the first direction to the open position.

6. The conserver of claim 5, wherein the pneumatic controller includes a demand piston moveable between a first position wherein fluid is not communicated from the fluid inlet to the fluid outlet and a second position wherein fluid is communicated from the fluid inlet to the fluid outlet, the demand piston moving between the first position and the second position along the first direction.

7. The conserver of claim 6, wherein the sense diaphragm moves towards the fluid inlet along the first direction when moving from the open position to the closed position.

8. The conserver of claim 7, wherein the piston moves towards the fluid inlet along the first direction when moving from the second position to the first position.

9. A conserver which receives a fluid from a source of pressurized fluid and provides fluid to a patient through a single lumen cannula, the conserver comprising:

a body having a fluid input, a fluid output providing a single fluid connection between the body and the single lumen cannula, wherein the single fluid connection is the only fluid connection between the body and the single lumen cannula, and a fluid passage configured to connect the fluid input to the fluid output;

a pressure reduction section disposed within the body and in fluid communication with the fluid passage, the pressure reduction section receiving fluid from the fluid inlet of the body at a first pressure and providing fluid to a portion of the fluid passage positioned downstream of the pressure reduction section;

at least one user input supported by the body;

a controller positioned downstream of the pressure reduction section, the controller having a first configuration to provide a continuous flow of fluid to the fluid outlet of the body in a continuous mode and a second configuration to provide an intermittent flow of fluid to the fluid outlet of the body in an intermittent mode wherein an inhalation of the patient is sensed through the fluid outlet coupled to the single lumen cannula by a sensing portion of the controller, the intermittent mode and the continuous mode being selectable by the at least one user input;

a coupler coupled to the body, the coupler having a fluid conduit in fluid communication with the fluid inlet of the body, the coupler being adapted to couple to a portable source of pressurized fluid, wherein the coupler is made from a first material selected from the group of a brass based material, a copper based material, and a titanium based material and the body is made from a second material selected from the group of an aluminum based material, a composite based material, and a polymeric based material; and a quick connect fitting coupled to the body, the quick connect fitting including a fluid conduit in fluid communication with the fluid inlet of the body and being adapted to be coupled to a second source of pressurized fluid, the quick connect fitting being spaced apart from the coupler such that both the portable source of pressurized fluid and the second source of pressurized fluid are coupled to the conserver at the same time.

10. The conserver of claim 9, wherein the second source of pressurized fluid is an oxygen concentrator.

11. The conserver of claim 9, wherein the quick connect fitting is coupled to a side of the body and the coupler is coupled to an end of the body.

12. A conserver which receives a fluid from a source of pressurized fluid and provides fluid to a patient through a single lumen cannula, the conserver comprising:

a body having a fluid input, a fluid output adapted to be coupled to a cannula providing a single fluid connection between the body and the single lumen cannula, wherein the single fluid connection is the only fluid connection between the body and the single lumen cannula, and a fluid passage configured to connect the fluid input to the fluid output;

a pressure reduction section disposed within the body and in fluid communication with the fluid passage, the pressure reduction section receiving fluid from the fluid inlet of the body at a first pressure and providing fluid to a portion of the fluid passage positioned downstream of the pressure reduction section;

a pneumatic controller positioned downstream of the pressure reduction section, the pneumatic controller having a first configuration to provide a continuous flow of fluid to the fluid outlet of the body in a continuous mode and to provide an intermittent flow of fluid to the fluid outlet of the body in an intermittent mode, the pneumatic controller including a demand piston which is spaced apart from a seat when fluid is being provided from the fluid inlet to the fluid outlet;

a flow selector having a plurality of fluid passages, each having a corresponding flow rate, the flow selector being positioned to receive fluid from the pressure reduction and to provide fluid to the pneumatic controller, the flow selector being rotatable relative to the body and including a first surface actuatable to rotate the flow selector, the first surface being actuatable from an exterior of the body and at least a portion of the first surface being moved from the exterior of the body to an interior of the body as the flow selector is rotated; and a coupler coupled to the body, the coupler having a fluid conduit in fluid communication with the fluid inlet of the body, the coupler being adapted to couple to a portable source of pressurized fluid, wherein the coupler is made from a first material selected from the group of a brass based material, a copper based material, and a titanium based material and the body is made from a second material selected from the group of an aluminum based material, a composite based material, and a polymeric based material.

13. The conserver of claim 12, wherein the flow selector is positioned between the fluid inlet in the body and the fluid outlet in the body.

14. The conserver of claim 12, wherein the flow selector is positioned between the pressure reduction section and the controller.

15. A conserver which receives a fluid from a source of pressurized fluid and provides fluid to a patient through a single lumen cannula, the conserver comprising:

a body having a fluid input, a fluid output adapted to be coupled to a cannula, and a fluid passage configured to connect the fluid input to the fluid output;

a pressure reduction section disposed within the body and in fluid communication with the fluid passage, the pressure reduction section receiving fluid from the fluid inlet of the body at a first pressure and providing fluid to a portion of the fluid passage positioned downstream of the pressure reduction section;

a pneumatic controller positioned downstream of the pressure reduction section, the pneumatic controller having a first configuration to provide a continuous flow of fluid to the fluid outlet of the body in a continuous mode and to provide an intermittent flow of fluid to the fluid outlet of the body in an intermittent mode;

a flow selector having a plurality of fluid passages, each having a corresponding flow rate, the flow selector being positioned to receive fluid from the pressure reduction and to provide fluid to the pneumatic controller; and a coupler coupled to the body, the coupler having a fluid conduit in fluid communication with the fluid inlet of the body, the coupler being adapted to couple to a portable source of pressurized fluid, wherein the coupler is made from a first material selected from the group of a brass based material, a copper based material, and a titanium based material and the body is made from a second material selected from the group of an aluminum based material, a composite based material, and a polymeric based material, wherein a position of the flow selector controls the placement of a valve which controls the pneumatic controller to place the pneumatic controller in one of the continuous mode and the intermediate mode.

16. The conserver of claim 15, wherein the flow selector includes a cam surface with which the valve interacts.

* * * * *